United States Patent
Alataris et al.

(10) Patent No.: US 10,493,275 B2
(45) Date of Patent: Dec. 3, 2019

(54) SPINAL CORD MODULATION FOR INDUCING PARESTHETIC AND ANESTHETIC EFFECTS, AND ASSOCIATED SYSTEMS AND METHODS

(71) Applicant: Nevro Corp., Redwood City, CA (US)

(72) Inventors: Konstantinos Alataris, Belmont, CA (US); Andre B. Walker, Monte Sereno, CA (US); Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 14/292,671

(22) Filed: May 30, 2014

(65) Prior Publication Data

US 2014/0296936 A1    Oct. 2, 2014

Related U.S. Application Data

(63) Continuation of application No. 12/765,685, filed on Apr. 22, 2010, now abandoned.
(Continued)

(51) Int. Cl.
*A61N 1/00* (2006.01)
*A61N 1/36* (2006.01)
*A61N 1/06* (2006.01)

(52) U.S. Cl.
CPC ....... *A61N 1/36071* (2013.01); *A61N 1/3615* (2013.01); *A61N 1/36021* (2013.01);
(Continued)

(58) Field of Classification Search
CPC ... A61N 1/00; A61N 1/02; A61N 1/05; A61N 1/06; A61N 1/08; A61N 1/18; A61N 1/20;
(Continued)

(56) References Cited

U.S. PATENT DOCUMENTS

| 1,597,061 A | 8/1926 | Cultra |
| 2,622,601 A | 12/1952 | Nemec |

(Continued)

FOREIGN PATENT DOCUMENTS

| DE | 10318071 A1 | 11/2004 |
| EP | 1181947 A2 | 2/2002 |

(Continued)

OTHER PUBLICATIONS

U.S. Appl. No. 12/765,773, filed Apr. 22, 2010 and entitled *Selective High Frequency Spinal Cord Modulation for Inhibiting Pain with Reduced Side Effects, and Associated Systems and Methods, Including Practitioner Processes.*

(Continued)

*Primary Examiner* — Christopher Koharski
*Assistant Examiner* — Elizabeth K So
(74) *Attorney, Agent, or Firm* — Perkins Coie LLP

(57) ABSTRACT

Spinal cord modulation for inducing paresthetic and anesthetic effects, and associated systems and methods are disclosed. A representative method in accordance with an embodiment of the disclosure includes creating a therapeutic effect and a sensation in a patient by delivering to the patient first pulses having a first set of first signal delivery parameters and second pulses having a second set of second signal delivery parameters, wherein a first value of at least one first parameter of the first set is different than a second value of a corresponding second parameter of the second set, and wherein the first pulses, the second pulses or both the first and second pulses are delivered to the patient's spinal cord.

29 Claims, 10 Drawing Sheets

Related U.S. Application Data

(60) Provisional application No. 61/171,790, filed on Apr. 22, 2009.

(52) U.S. Cl.
CPC ..... *A61N 1/36132* (2013.01); *A61N 1/36171* (2013.01); *A61N 1/36178* (2013.01); *A61N 1/06* (2013.01)

(58) Field of Classification Search
CPC .......... A61N 1/32; A61N 1/36; A61N 1/3605; A61N 1/3606; A61N 1/36071; A61N 1/36078; A61N 1/36128; A61N 1/3615; A61N 1/36167
See application file for complete search history.

(56) References Cited

U.S. PATENT DOCUMENTS

| | | | |
|---|---|---|---|
| 3,195,540 A | 7/1965 | Waller |
| 3,727,616 A | 4/1973 | Lenzkes |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,155,366 A | 5/1979 | Di Mucci |
| 4,331,145 A | 5/1982 | Winter |
| 4,379,462 A | 4/1983 | Borkan et al. |
| 4,414,986 A | 11/1983 | Dickhudt et al. |
| 4,535,777 A | 8/1985 | Castel |
| 4,541,432 A | 9/1985 | Molina-Negro et al. |
| 4,550,733 A | 11/1985 | Liss et al. |
| 4,608,985 A | 9/1986 | Crish et al. |
| 4,612,934 A | 9/1986 | Borkan et al. |
| 4,649,935 A | 3/1987 | Charmillot et al. |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill et al. |
| 5,036,862 A | 8/1991 | Pohndorf |
| 5,188,104 A | 2/1993 | Wernicke et al. |
| 5,335,657 A | 8/1994 | Terry, Jr. et al. |
| 5,514,175 A | 5/1996 | Kim et al. |
| 5,540,734 A | 7/1996 | Zabara |
| 5,562,717 A | 10/1996 | Tippey et al. |
| 5,643,330 A | 7/1997 | Holsheimer et al. |
| 5,713,922 A | 2/1998 | King |
| 5,716,377 A | 2/1998 | Rise et al. |
| 5,725,563 A | 3/1998 | Klotz et al. |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,941,906 A | 8/1999 | Barreras, Sr. et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feier et al. |
| 6,049,701 A | 4/2000 | Sparksman |
| 6,058,331 A | 5/2000 | King |
| 6,161,044 A | 12/2000 | Silverstone |
| 6,161,048 A | 12/2000 | Sluijter et al. |
| 6,167,305 A | 12/2000 | Cammilli et al. |
| 6,167,311 A | 12/2000 | Rezai |
| 6,176,242 B1 | 1/2001 | Rise |
| 6,185,463 B1 | 2/2001 | Baudino |
| 6,192,279 B1 | 2/2001 | Barreras, Sr. et al. |
| 6,233,488 B1 | 5/2001 | Hess |
| 6,238,423 B1 | 5/2001 | Bardy |
| 6,246,912 B1 | 6/2001 | Sluijter et al. |
| 6,292,695 B1 | 9/2001 | Webster, Jr. et al. |
| 6,308,103 B1 | 10/2001 | Gielen |
| 6,319,241 B1 | 11/2001 | King et al. |
| 6,341,236 B1 | 1/2002 | Osorio et al. |
| 6,356,786 B1 | 3/2002 | Rezai et al. |
| 6,364,899 B1 | 4/2002 | Dobak, III |
| 6,366,814 B1 | 4/2002 | Boveja |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,529,774 B1 | 3/2003 | Greene |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann |
| 6,659,968 B1 | 12/2003 | McClure |
| 6,662,051 B1 | 12/2003 | Eraker et al. |
| 6,714,822 B2 | 3/2004 | King et al. |
| 6,721,603 B2 | 4/2004 | Zabara et al. |
| 6,745,079 B2 | 6/2004 | King |
| 6,795,737 B2 | 9/2004 | Gielen et al. |
| 6,850,802 B2 | 2/2005 | Holsheimer et al. |
| 6,856,315 B2 | 2/2005 | Eberlein |
| 6,871,090 B1 | 3/2005 | He et al. |
| 6,871,099 B1 | 3/2005 | Whitehurst et al. |
| 6,885,888 B2 | 4/2005 | Rezai |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,110,820 B2 | 9/2006 | Tcheng et al. |
| 7,110,827 B2 | 9/2006 | Sage et al. |
| 7,117,034 B2 | 10/2006 | Kronberg |
| 7,142,923 B2 | 11/2006 | North et al. |
| 7,146,217 B2 | 12/2006 | Firlik et al. |
| 7,146,224 B2 | 12/2006 | King |
| 7,149,574 B2 | 12/2006 | Yun et al. |
| 7,162,304 B1 | 1/2007 | Bradley |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B2 | 2/2007 | Varrichio et al. |
| 7,181,286 B2 | 2/2007 | Sieracki et al. |
| 7,206,640 B1 | 4/2007 | Overstreet |
| 7,212,865 B2 | 5/2007 | Cory |
| 7,221,979 B2 | 5/2007 | Zhou et al. |
| 7,225,035 B2 | 5/2007 | Brabec et al. |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,328,068 B2 | 2/2008 | Spinelli et al. |
| 7,328,069 B2 | 2/2008 | Gerber |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |

(56) References Cited

U.S. PATENT DOCUMENTS

| | | |
|---|---|---|
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,427,280 B2 | 9/2008 | Gerber |
| 7,433,734 B2 | 10/2008 | King |
| 7,463,927 B1 | 12/2008 | Chaouat |
| 7,483,747 B2 | 1/2009 | Gliner et al. |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,613,520 B2 | 11/2009 | De Ridder |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,877,136 B1 | 1/2011 | Moffitt et al. |
| 7,877,146 B2 | 1/2011 | Rezai |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,027,718 B2 | 9/2011 | Spinner et al. |
| 8,060,208 B2 | 11/2011 | Kilgore et al. |
| 8,082,039 B2 | 12/2011 | Kim et al. |
| 8,209,028 B2 | 6/2012 | Skelton et al. |
| 8,224,459 B1 | 7/2012 | Pianca et al. |
| 8,280,515 B2 | 10/2012 | Greenspan |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,396,559 B2 | 3/2013 | Alataris et al. |
| 8,428,735 B2 | 4/2013 | Littlewood et al. |
| 8,612,018 B2 | 12/2013 | Gillbe |
| 8,649,874 B2 | 2/2014 | Alataris et al. |
| 8,666,506 B2 | 3/2014 | King |
| 8,718,781 B2 | 5/2014 | Alataris et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 9,002,459 B2 | 4/2015 | Lee et al. |
| 9,067,076 B2 | 6/2015 | Nolan et al. |
| 9,180,298 B2 | 11/2015 | Alataris et al. |
| 9,295,840 B1 | 3/2016 | Thacker |
| 9,327,127 B2 | 5/2016 | Alataris et al. |
| 9,561,370 B2 | 2/2017 | Rezai |
| 9,895,539 B1 | 2/2018 | Heit et al. |
| 2002/0055779 A1 | 5/2002 | Andrews |
| 2002/0128700 A1 | 9/2002 | Cross |
| 2003/0100931 A1 | 5/2003 | Mullett |
| 2003/0120323 A1 | 6/2003 | Meadows et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 | 6/2004 | Whitehorse |
| 2004/0162590 A1 | 8/2004 | Whitehurst et al. |
| 2004/0167584 A1* | 8/2004 | Carroll ............... A61N 1/0551 607/46 |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038484 A1 | 2/2005 | Knudson et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0240241 A1 | 10/2005 | Yun et al. |
| 2005/0245978 A1 | 11/2005 | Varrichio et al. |
| 2005/0246006 A1 | 11/2005 | Daniels |
| 2005/0267545 A1 | 12/2005 | Cory |
| 2005/0278000 A1 | 12/2005 | Strother et al. |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0161236 A1 | 7/2006 | King |
| 2006/0167525 A1 | 7/2006 | King |
| 2006/0168805 A1 | 8/2006 | Hegland et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0106337 A1 | 5/2007 | Errico et al. |
| 2007/0106342 A1 | 5/2007 | Schumann |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0203537 A1 | 8/2007 | Goetz et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265681 A1 | 11/2007 | Gerber et al. |
| 2007/0293915 A1 | 12/2007 | Kilgore et al. |
| 2007/0299482 A1 | 12/2007 | Littlewood et al. |
| 2008/0033511 A1 | 2/2008 | Dobak |
| 2008/0058878 A1 | 3/2008 | King |
| 2008/0058888 A1 | 3/2008 | King |

(56) References Cited

U.S. PATENT DOCUMENTS

| | | |
|---|---|---|
| 2008/0065158 A1 | 3/2008 | Ben-Ezra |
| 2008/0097539 A1 | 4/2008 | Belalcazar |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0294221 A1 | 11/2008 | Kilgore et al. |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0112282 A1 | 4/2009 | Kast et al. |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264973 A1 | 10/2009 | Boling et al. |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0069993 A1 | 3/2010 | Greenspan |
| 2010/0094375 A1 | 4/2010 | Donders et al. |
| 2010/0125313 A1 | 5/2010 | Lee et al. |
| 2010/0137938 A1 | 6/2010 | Kishawl et al. |
| 2010/0152817 A1 | 6/2010 | Gillbe |
| 2010/0191307 A1 | 7/2010 | Fang et al. |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0150252 A1 | 6/2012 | Feldman et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris et al. |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0261695 A1 | 10/2013 | Thacker et al. |
| 2013/0261696 A1 | 10/2013 | Thacker et al. |
| 2013/0261697 A1 | 10/2013 | Parker et al. |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032182 A1 | 1/2015 | Alataris et al. |
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0217116 A1 | 8/2015 | Parramon et al. |
| 2015/0343220 A1 | 12/2015 | Alataris et al. |
| 2016/0121119 A1 | 5/2016 | Alataris et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2017/0050021 A1 | 2/2017 | Cosman, Sr. |
| 2017/0165485 A1 | 6/2017 | Sullivan et al. |

FOREIGN PATENT DOCUMENTS

| | | |
|---|---|---|
| EP | 2243511 A2 | 10/2010 |
| EP | 2448633 A1 | 5/2012 |
| EP | 2630984 A1 | 8/2013 |
| GB | 2449546 A | 11/2008 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006083884 A1 | 8/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |

(56) References Cited

FOREIGN PATENT DOCUMENTS

| WO | WO-2008142402 A1 | 11/2008 |
|---|---|---|
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009097226 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2016154091 A1 | 9/2016 |

OTHER PUBLICATIONS

U.S. Appl. No. 12/765,805, filed Apr. 22, 2010 and entitled *Selective High Frequency Spinal Cord Modulation for Inhibiting Pain with Reduced Side Effects, and Associated Systems and Methods, Including Implantable Patient Leads*.

U.S. Appl. No. 13/245,471, filed Sep. 26, 2011 and entitled *Selective High Frequency Spinal Cord Modulation for Inhibiting Pain with Reduced Side Effects, and Associated Systems and Methods*.

U.S. Appl. No. 13/398,693, filed Feb. 16, 2012 and entitled *Selective High Frequency Spinal Cord Modulation for Inhibiting Pain with Reduced Side Effects, and Associated Systems and Methods*.

U.S. Appl. No. 13/446,944, filed Apr. 13, 2012 and entitled *Selective High Frequency Spinal Cord Modulation for Inhibiting Pain with Reduced Side Effects, and Associate Systems and Methods*.

U.S. Appl. No. 13/446,992, filed Apr. 13, 2012 and entitled *Selective High Frequency Spinal Cord Modulation for Inhibiting Pain with Reduced Side Effects, and Associate Systems and Methods*.

U.S. Appl. No. 13/447,026, filed Apr. 13, 2012 and entitled *Selective High Frequency Spinal Cord Modulation for Inhibiting Pain with Reduced Side Effects, and Associate Systems and Methods*.

U.S. Appl. No. 13/447,050, filed Apr. 13, 2012 and entitled *Selective High Frequency Spinal Cord Modulation for Inhibiting Pain with Reduced Side Effects, and Associate Systems and Methods*.

U.S. Appl. No. 13/620,235, filed Sep. 14, 2012 and entitled *Selective High Frequency Spinal Cord Modulation for Inhibiting Pain with Reduced Side Effects, and Associate Systems and Methods*.

U.S. Appl. No. 13/728,965, filed Dec. 27, 2012 and entitled *Selective High Frequency Spinal Cord Modulation for Inhibiting Pain with Reduced Side Effects, and Associate Systems and Methods*.

U.S. Appl. No. 13/830,886, filed Mar. 14, 2013 and entitled *Selective High Frequency Spinal Cord Modulation for Inhibiting Pain with Reduced Side Effects, and Associate Systems and Methods*.

U.S. Appl. No. 13/830,992, filed Mar. 14, 2013 and entitled *Selective High Frequency Spinal Cord Modulation for Inhibiting Pain with Reduced Side Effects, and Associate Systems and Methods*.

U.S. Appl. No. 13/830,788, filed Mar. 14, 2013 and entitled *Selective High Frequency Spinal Cord Modulation for Inhibiting Pain with Reduced Side Effects, and Associate Systems and Methods*.

U.S. Appl. No. 13/831,057, filed Mar. 14, 2013 and entitled *Selective High Frequency Spinal Cord Modulation for Inhibiting Pain with Reduced Side Effects, and Associate Systems and Methods*.

U.S. Appl. No. 14/037,193, filed Sep. 25, 2013 and entitled *Selective High Frequency Spinal Cord Modulation for Inhibiting Pain with Reduced Side Effects, and Associated Systems and Methods*.

U.S. Appl. No. 14/037,230, filed Sep. 25, 2013 and entitled *Selective High Frequency Spinal Cord Modulation for Inhibiting Pain with Reduced Side Effects, and Associate Systems and Methods*.

U.S. Appl. No. 14/037,262, filed Sep. 25, 2013 and entitled *Selective High Frequency Spinal Cord Modulation for Inhibiting Pain with Reduced Side Effects, and Associate Systems and Methods*.

U.S. Appl. No. 14/164,044, filed Jan. 24, 2014 and entitled *Selective High Frequency Spinal Cord Modulation for Inhibiting Pain with Reduced Side Effects, and Associate Systems and Methods*.

U.S. Appl. No. 14/164,057, filed Jan. 24, 2014 and entitled *Selective High Frequency Spinal Cord Modulation for Inhibiting Pain with Reduced Side Effects, and Associate Systems and Methods*.

U.S. Appl. No. 14/164,082, filed Jan. 24, 2014 and entitled *Selective High Frequency Spinal Cord Modulation for Inhibiting Pain with Reduced Side Effects, and Associate Systems and Methods*.

U.S. Appl. No. 14/164,096, filed Jan. 24, 2014 and entitled *Selective High Frequency Spinal Cord Modulation for Inhibiting Pain with Reduced Side Effects, and Associate Systems and Methods*.

U.S. Appl. No. 14/164,100, filed Jan. 24, 2014 and entitled *Selective High Frequency Spinal Cord Modulation for Inhibiting Pain with Reduced Side Effects, and Associate Systems and Methods*.

U.S. Appl. No. 14/199,867, filed Mar. 6, 2014 and entitled *Selective High Frequency Spinal Cord Modulation for Inhibiting Pain with Reduced Side Effects, and Associate Systems and Methods*.

U.S. Appl. No. 14/261,369, filed Apr. 24, 2014 and entitled *Selective High Frequency Spinal Cord Modulation for Inhibiting Pain with Reduced Side Effects, and Associate Systems and Methods*.

U.S. Appl. No. 11/235,947, filed Sep. 26, 2005 and entitled *Neural Blocking Therapy*.

U.S. Appl. No. 12/045,394, filed Mar. 10, 2008 and entitled *Neural Blocking Therapy*.

U.S. Appl. No. 12/765,790, filed Apr. 22, 2010 and entitled *Devices for Controlling High Frequency Spinal Cord Modulation for Inhibiting Pain, and Associated Systems and Methods, Including Simplified Controllers*.

U.S. Appl. No. 12/765,810, filed Apr. 22, 2010 and entitled *Devices for Controlling High Frequency Spinal Cord Modulation for Inhibiting Pain, and Associated Systems and Methods, Including Simplified Contact Selection*.

U.S. Appl. No. 12/765,824, filed Apr. 22, 2010 and entitled *Devices for Controlling High Frequency Spinal Cord Modulation for Inhibiting Pain, and Associated Systems and Methods, Including Simplified Program Selection*.

U.S. Appl. No. 13/245,500, filed Sep. 26, 2011 and entitled *Devices for Controlling High Frequency Spinal Cord Modulation for Inhibiting Pain, and Associated Systems and Methods, Including Simplified Controllers*.

U.S. Appl. No. 12/264,836, filed Nov. 4, 2008 and entitled *Multi-Frequency Neural Treatments and Associated Systems and Methods*.

U.S. Appl. No. 13/620,307, filed Sep. 14, 2012 and entitled *Multi-Frequency Neural Treatments and Associated Systems and Methods*.

U.S. Appl. No. 13/705,021, filed Dec. 14, 2012 and entitled *Multi-Frequency Neural Treatments and Associated Systems and Methods*.

U.S. Appl. No. 13/705,045, filed Dec. 14, 2012 and entitled *Multi-Frequency Neural Treatments and Associated Systems and Methods*.

U.S. Appl. No. 14/181,549, filed Feb. 14, 2014 and entitled *Multi-Frequency Neural Treatments and Associated Systems and Methods*.

U.S. Appl. No. 12/765,685, filed Apr. 22, 2010 and entitled *Spinal Cord Modulation for Inducing Paresthetic and Anesthetic Effects, and Associated Systems and Methods*.

Bahdra et al., Stimulation of High-Frequency Sinusoidal Electrical Block of Mammalian Myelinated Axons, J Comput Neurosco, 22:313-326, 2007.

Barolat et al., "Multifactorial Analysis of Epidural Spinal Cord Stimulation," Sterotactic and Functional Neurosurgery, 1991; 56: 77-103.

Bhadra et al., "High Frequency electrical conduction block of the pudendal nerve," Journal of Neural Engineering—Institute of Physics Publishing, 2006, 8 pages.

Bhadra MD, Niloy et al., "High-Frequency Electrical Conduction Block of Mammalian Peripheral Motor Nerve," Muscle and Nerve, Dec. 2005, 9 pages.

Boger et al., "Bladder Voiding by Combined High Frequency Electrical Pudendal Nerve Block and Sacral Root Stimulation," Neurourology and Urodynamics, 27, 2008, 5 pages.

Bowman and McNeal, Response of Single Alpha Motoneurons to High-Frequency Pulse Trains, Appl. Neurophysiol. 49, p. 121-138, 1986, 10 pages.

Burton, Charles, "Dorsal Column Stimulation: Optimization of Application,"Surgical Neurology, vol. 4 No. 1, Jul. 1975, 10 pages.

Dapoigny, "Vagal influence on colonic motor activity in conscious nonhuman primates," AM Journal Physiological Society, 1992, 6 pages.

(56) References Cited

OTHER PUBLICATIONS

DeRidder et al., "Are Paresthesias necessary for pain suppression in SCS—Burst Stimulation," Brain, Brain Research Center Antwerp of Innovative and Interdisciplinary Neuromodulation, 2010, 27 pages.

DeRidder et al., "Burst Spinal Cord Stimulation: Toward Paresthesia-Free Pain Suppression," www.neurosurgery-online.com, vol. 66, No. May 5, 2010, 5 pages.

Extended European Search Report for European Application No. 10767788.2, Applicant: Nevro Corporation, dated Nov. 11, 2012, 3 pages.

Grill, Warren et al., "Stimulus Waveforms for Selective Neural Stimulation," IEEE Engineering in Medicine and Biology, Jul./Aug. 1995, pp. 375-365.

Holsheimer—Effectiveness of Spinal Cord Stimulation in the Management of Chronic Pain: Analysis of Technical Drawbacks and Solutions, Neurosurgery, vol. 40, No. 5, May 1997, pp. 909-999.

Hopp et al , "Effect of anodal blockade of myelinated fibers on vagal c-fiber afferents," American Journal Physiological Society, Nov. 1980; 239(5), 9 pages.

Hoppenstein, Reuben, "Electrical Stimulation of the Ventral and Dorsal Columns of the Spianl Cord for Relief of Chronic Intractable Pain: Preliminary Report," Surgical Neurology, vol. 4, No. 1, Jul. 1975, 9 pages.

Huxely et al., "Excitation and Conduction in Nerve: Quantitative Analysis." Science. Sep. 11, 1964; 145: 1154-9.

International Search Report and Written Opinion, International Application No. PCT/US2010/032110, Applicant: Nevro Corporation, dated Jun. 28, 2010, 19 pages.

Jang et al., "Analysis of Failed Spinal Cord Stimulation Trails in the Treatment of Intractable Chronic Pain," J. Korean Neurosurg Soc 43, 2008, 5 pages.

Kilgore et al. "Nerve Conduction Block Utilizing High-Frequency Alternating Current" Medical & Biology Engineering and Computing, 2004, vol. 24, pp. 394-406.

Kilgore et al. "Reversible Nerve Conduction Block Using Kilohertz Frequency Alternating Current," Neuromodulation Technology at the Neural Interface, International Neuromodulation Society, 2013, 13 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Linderoth et al., "Mechanisms of Spinal Cord Stimulation in Painful Syndromes: Role of Animal Models," Pain Medicine, vol. 7, No. S1, 2006, 13 pages.

Linderoth et al., "Physiology of Spinal Cord Stimulation: Review and Update," Neuromodulation, vol. 2, No. 3, 1999, 15 pages.

Mediati, R.D., , "Mechanisms of Spinal Cord Stimulation." Florence, Oct. 2, 2002, 31 pages.

Melzack, Ronald et al., "Pain Mechanisms: A New Theory," Science, vol. 150, No. 3699, Nov. 19, 1965, 9 pages.

Muller and Hunsperger, "Helvetica Physiologica Acta—Reversible Blockierung der Erregungsleitung im Nerven durch Mittelfrequenz—Daverstrom," Schwabe & Co. Basel, vol. 25, Fasc. 1, 1967, 4 pages.

North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.

North et al., "Spinal Cord Stimulation for Axial Low Back Pain," SPINE. vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Oakley, John C., "Spinal Cord Stimulation Mechanisms of Action," SPINE vol. 27, No. 22, copyright 2002, 10 pages.

Paterson CA et al., "Determinants of Occurrence and Volume of Transpyloric Flow During Gastric Emptying of Liquids in Dogs: Importance of Vagal Input," Digital Disease and Science, vol. 45, No. 8, Aug. 2000, 8 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Shealy MD, C. Norman et al., "Electrical Inhibition of Pain by Stimulation of the Dorsal Columns: Preliminary Clinical Report," Anesthesia and Analgesia Current Researches, vol. 446, No. 4, Jul.-Aug. 1967,3 pages.

Simpson, BA, "Spinal Cord Stimulation in 60 cases of Intractable Pain." Journal of Neurology, Neurosurgery and Psychiatry, 1991; 54 pp. 196-199.

Simpson, BA, "Spinal Cord Stimulation." British Journal of Neurosurgery, Feb. 11, 1997 (1), 5-11, 7 pages.

Solomonow et al., "Control of Muscle Contractile Force through Indirect High-Frequency Stimulation," AM Journal of Physical Medicine, 1983, vol. 62, No. 3. pp. 71-82.

Tanner, J.A., "Reversible blocking of nerve conduction by alternating-current excitation," Nature, Aug. 18, 1962; 195: 712-3.

Urban et al., "Percutaneous epidural stimulation of the spinal cord for relief of pain—Long Term Results," Journal of Neurosurgery, vol. 48, Mar. 1978, 7 pages.

Van Den Honert et al. "Generation of Unidirectionally Propagated Action Potentials Nerve by Brief Stimuli" Science, vol. 26, pp. 1311-1312.

Van Den Honert, Mortimer JT, "A Technique for Collison Block of Peripheral Nerve: Frequency Dependence," MP-11 IEEE Trans. Biomed. Eng. 28: 379-382, 1981.

Wolter et al., "Continuous Versus Intermittent Spinal Cord Stimulation. An Analysis of Factors Influencing Clinical Efficacy," Neuromodulation: Technology at Neural Interface, www.neuromodulationjournal.com, 2011, 8 pages.

Woo MY, Campbell B. "Asynchronous Firing and Block of Peripheral Nerve Conduction by 20KC Alternating Current," Los Angeles Neuro Society, Jun. 1964; 87-94, 5 pages.

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.

"The Need for Mechanism-Based Medicine in Neuromodulation," Neuromodulation: Technology at the Neural Interface, 2012, 7 pages.

Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.

Amendment in Response to Ex Parte Office Action for U.S. Appl. No. 13/446,970, First Named Inventor: Konstantinos Alataris, dated Nov. 28, 2012, 14 pages.

Amendment in Response to Non-Final Office Action for U.S. Appl. No. 13/245,450, First Named Inventor: Konstantinos Alataris, filed: Feb. 7, 2012, 15 pages.

Amendment in Response to Non-Final Office Action for U.S. Appl. No. 12/765,747, First Named Inventor: Konstantinos Alataris, dated Jan. 24, 2014, 21 pages.

Applicant-Initiated Interview Summary for U.S. Appl. No. 13/245,450, First Named Inventor: Konstantinos Alataris, dated Feb. 1, 2012, 2 pages.

Applicant-Initiated Interview Summary for U.S. Appl. No. 13/725,770, First Named Inventor: Konstantinos Alataris, dated Apr. 5, 2013, 3 pages.

Applicant-Initiated Interview Summary for U.S. Appl. No. 12/765,747, First Named Inventor: Konstantinos Alataris, dated Sep. 11, 2013, 3 pages.

Application Data Sheet for U.S. Appl. No. 13/446,970 (U.S. Pat. No. 8,359,102), First Named Inventor: Konstantinos Alataris, filed Apr. 13, 2012, 6 pages.

Barolat et al., "Surgical Management of Pain—Spinal Cord Stimulation: Equipment and Implantation Techniques," Chapter 41, Thieme Medical Publishers, New York, 2002, 11 pages.

Boston Scientific "Precision™ Spinal Cord Stimulator System Clinician Manual—Directions for Use," 2015, 74 pages.

(56) References Cited

OTHER PUBLICATIONS

Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
ClinicalTrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Declaration of Cameron C. McIntyre, Ph.D., May 6, 2015, Attorney Ref: 1014.0248AB1, 88 pages.
Declaration of Cameron C. McIntyre, Ph.D., May 6, 2015, Attorney Ref: 1014.0248AB2, 57 pages.
Declaration of M. Jason D. Rahn, Jan. 7, 2015, 7 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Ex Parte Office Action for U.S. Appl. No. 13/446,970, First Inventor Named: Konstantinos Alataris, dated Oct. 15, 2012, 9 pages.
First Preliminary Amendment for U.S. Appl. No. 13/446,970, First Named Inventor: Konstantinos Alataris, dated May 18, 2012, 7 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
JMP Securities, "Nevro Corp. (NVRO) Initiating Coverage on Nevro Corp. with a Market Outperform Rating—Investment Highlights," Dec. 1, 2014, 42 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Munglani, Rajesh, "The Longer Term Effect of Pulsed Radiofrequency for Neuropathic Pain," PAIN 80, 1999, 3 pages.
Nevro Senza Patient Manual, Jan. 16, 2015, 53 pages.
Nevro Senza Physician Implant Manual, Jan. 16, 2015, 31 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Merriam Webster's Collegiate Dictionary, Tenth Edition, definition of "Implantable," 1995, 3 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Nevro, PMA Approval Letter and Referenced Summary of Safety and Effectiveness Data (SSED) May 8, 2015, 60 pages.
News Release Details, "Nevro Corp. Announces Pricing of Initial Public Offering," 2014, 1 page.
Non-Final Office Action for U.S. Appl. No. 12/765,747, First Named Inventor: Konstantinos Alataris, dated Jul. 25, 2013, 7 pages.
Non-Final Office Acton for U.S. Appl. No. 13/245,450, First Named Inventor: Konstantinos Alataris, dated Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
Notice of Opposition to a European Patent, Argument and Facts, and Annex for European Patent No. 2421600, Proprietor of the Patent: Nevro Corporation; Opponent: Boston Scientific Neuromodulation Corporation, dated Dec. 4, 2014, 22 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
Notice of Allowance for U.S. Appl. No. 13/245,450, First Named Inventor: Konstantinos Alataris, dated Mar. 14, 2012, 8 pages.
Notice of Opposition to a European Patent, Argument and Facts, for European Patent No. 2243510, Proprietor of the Patent: Nevro Corporation, Opponent: Medtronic, dated Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, dated Jan. 8, 2015, 28 pages.
Notice of Opposition to a European Patent, Argument and Facts for European Patent No. 2630984, Proprietor of the Patent: Nevro Corporation; Opponent: Medtronic, dated Mar. 17, 2015, 17 pages.
Notice of Opposition to a European Patent, Argument and Facts, and Annex for European Patent No. 2630984, Proprietor of the Patent: Nevro Corporation; Opponent: Boston Scientific Neuromodulation Corporation, dated Mar. 17, 2015, 21 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley et al., "Spinal Cord Stimulation in Axial Low Back Pain: Solving the Dilemma," Pain Medicine, vol. 7, No. S1, 2006, 6 pages.
Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, dated Sep. 1, 2015, 70 pages.
Science Daily, "Chronic Pain Costs U.S. up to $635 billion, study shows," www.sciencedaily.com/releases/2012/09/120911091100.htm, Sep. 11, 2012, 2 pages.

(56) References Cited

OTHER PUBLICATIONS

Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, mailed Sep. 1, 2015, 63 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB2, May 14, 2015, 45 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, Attorney Ref: 1014.0248AB1, May 14, 2015, 67 pages.
Prausnitz et al., "The Effects of Electric Current Applied to Skin: A Review for Transdermal Drug Delivery," Advanced Drug Delivery Reviews 18, ; 1996, 31 pages.
Resume of Jason D. Rahn, Jan. 7, 2015, 2 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
St. Jude Medical, "Eon Mini™ Rechargeable IPG," Apr. 29, 2013, 3 pages.
St. Jude Medical, "Individualized Therapy through Diverse Lead Options," 2008, 6 pages.
Stimwave, News Release: "Stimwave Receives FDA Approval for High Frequency IDE," http://stimwave.com/newsroom/latest-news, Jun. 9, 2015, 2 pages.
Tesfaye et al., "Electrical Spinal Cord Stimulation for Painful Diabetic Peripheral Neuropathy," The Lancet, vol. 348, Dec. 21-28, 1996, 4 pages.
Tollison et al., "Practical Pain Management; Neurostimulation Techniques," Chapter 12, Lippincott Williams and Wilkins, Third Edition, 2002, 13 pages.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neurmodulation Society, 2014, 4 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Webster's Third New International Dictionary of the English Language Unabridged, "Paresthesia," 1993, 3 pages.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Non-Final Office Action for U.S. Appl. No. 14/512,325, dated Oct. 7, 2015, 15 pages.
Acticare.com website, http://web.archive.org/web/*/acticare.com, Internet Archive Way Back Machine, 2012, 22 pages.
Hefferman et al., "Efficacy of Transcutaneous Spinal Electroanalgesia in Acute Postoperative Pain Management," Anesthesiology, 2001, 2 pages.
Hilberstadt et al., "The Effect of Transcutaneous Spinal Electroanalgesia upon Chronic Pain: A single case study," Physiotherapy, vol. 86 No. 3, Mar. 2000, 2 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Notice of Opposition to a European Patent, Argument and Facts, for European Patent No. 2207587, Proprietor of the Patent: Nevro Corporation; Opponent: Medtronic, Inc., dated Jan. 12, 2016, 22 pages.
Notice of Opposition to a European Patent, Argument and Facts, for European Patent No. 2207587, Proprietor of the Patent: Nevro Corporation; Opponent: Boston Scientific Neuromodulation Corporation, dated Jan. 8, 2016, 17 pages.
Palmer et al., "Transcutaneous electrical nerve stimulation and transcutaneous spinal electroanalgesia: A preliminary efficacy and mechanisms-based investigation," Physiotherapy, 95, 2009, 7 pages.
Remedi Pain Relief—ENM (Electronic Nerve Modulation), https://web.archive.org/web/20050906181041/http://www.remediuk.com/trials.htm, 2005, 5 pages.
Robb et al., "Transcutaneous Electrical Nerve Stimulation vs. Transcutaneous Spinal Electroanalgesia for Chronic Pain Associated with Breast Cancer Treatments," Journal of Pain and Symptom Management, vol. 33, No. 4, Apr. 2007, 10 pages.
Royle, John., "Transcutaneous Spinal Electroanalgesia and Chronic Pain," Physiotherapy, vol. 86, No. 5, May 2000, 1 page.
Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Towell et al., "High Frequency non-invasive stimulation over the spine: Effects on mood and mechanical pain tolerance in normal subjects," Behavioral Neurology, vol. 10, 1997, 6 pages.
Advanced Neuromodulation Systems, Compustim SCS Systems, Clinical Manual, 1997, 52 pages.
Augustinsson et al., "Spinal Cord Stimulation in Cardiovascular Disease," Functional Neurosurgery, vol. 6, No. 1, Jan. 1995, 10 pages.
Barolat et al., "Spinal Cord Stimulation for Chronic Pain Management," Seminars in Neurosurgery, vol. 15, Nos. 2/3, 2004, 26 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Butt et al., "Histological Findings Using Novel Stimulation Parameters in a Caprine Model," European Journal of Pain Supplements, 2011, 2 pages.
Curriculum Vitae and Declaration of Dr. Ganesan Baranidharan on behalf of European Patent No. 2630984, 19 pages, 2016.
Curriculum Vitae and Declaration of Dr. Jonathan Miller on behalf of European Patent No. 2630984,42 pages, Oct. 25, 2016.
Curriculum Vitae and Declaration of Dr. Simon James Thomson on behalf of European Patent No. 2630984, Oct. 24, 2016, 13 pages.
Curriculum Vitae and Declaration of Prof. Bengt Linderoth on behalf of European Patent No. 2630984, Oct. 21, 2016, 6 pages.
Curriculum Vitae of Michael A. Moffitt for European Patent No. 2630984, 2015, 2 pages.
Declaration of M. Jason D. Rahn for European Patent No. 2243510, dated Feb. 2, 2017, 2 pages.
Declaration of Prof. Bengt Linderoth for European Patent No. 2421600, dated Dec. 16, 2016 2 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Feeling vs. Function Poster, Mager and Associates Consulting, 2009, 1 page.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Manola et al., "Technical Performance of Percutaneous Leads for Spinal Cord Stimulation: A Modeling Study," International Neuromodulation Society, 2005, 12 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx, 2016, 3 pages.

(56) References Cited

OTHER PUBLICATIONS

Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview, www.nevro.com/English/Physicians/Physician-Overview/default.aspx, 2016, 5 pages.
Nevro—Senza System, http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Observations and Response to Notice of Oppositions filed by Medtronic Inc., and Boston Scientific for European Patent No. 2207587, mailed Aug. 26, 2016, 16 pages.
Nevro Response to Notice of Oppositions filed by Boston Scientific for European Patent No. 2421600, mailed Jul. 22, 2015, 16 pages.
Nevro Response to Notice of Oppositions filed by Medtronic and Boston Scientific for European Patent No. 2630984, mailed Dec. 7, 2015, 26 pages.
Nevro Response to Opposition of Division's Comments and Summons to Oral Proceedings for European Patent No. 2630984, mailed Oct. 25, 2016, 8 pages.
Nevro website: HF10 Therapy Advantages, www.nevro.com/English/Patients/HF10-Therapy-Advantages/default.aspx, 2016, 3 pages.
Nevro Written Submissions and Response to Notice of Oppositions filed by Medtronic Inc., and Boston Scientific for European Patent No. 2243510, mailed Aug. 28,2015, 17 pages.
Nevro's Response to Further Submission by Medtronic, Inc., and Boston Scientific Neuromodulation Corporation for European Patent No. 2243510, mailed Feb. 24, 2017, 9 pages.
Nevro's presentation of HF10 therapy on Nevro's website, http://www.nevro.com/English/Home/default.aspx, 2016, 2 pages.
Nevros Response to Opponent Submission of Declaration of Jonathan Miller in European Patent No. 2630984, mailed Nov. 18, 2016, 4 pages.
Nevro's Response to Preliminary Opinion for Opposition by Medtronic, Inc., and Boston Scientific Neuromodulation Corporation for European Patent No. 2243510, mailed Feb. 3, 2017, 36 pages.
Opponent Boston Scientific: Response to Attend Oral Proceedings for European Patent No. 2630984, mailed Oct. 25, 2016, 21 pages.
Opponent Response to Patent Proprietor Comments to Declaration of Dr. Jonathan Miller for European Patent No. 2630984, mailed Nov. 22, 2016, 3 pages.
Opponents Boston Scientific Neuromodulation Corp.: Additional Observations in view of Oral Proceedings for European Patent No. 2243510, mailed Feb. 2, 2017, 8 pages.
Opponents Boston Scientific: Response to Summons to Attend Oral Proceedings for European Patent No. 2421600, mailed Jan. 2, 2017, 15 pages.
Opponents Medtronic, Inc.: Additional Observations in view of Oral Proceedings for European Patent No. 2243510, mailed Feb. 3, 2017, 10 pages.
Opponents Medtronic, Inc.: Response to Attend Oral Proceedings for European Patent No. 2630984, mailed Oct. 25, 2016, 26 pages.
Opponents Response to Patentee's (Nevro) Written Submissions for European Patent No. 2243510, mailed Feb. 22, 2016, 21 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Agnew et al., "Considerations for safety with chronically implanted nerve electrodes," Epilepsia, 31.s2, 1990, 6 pages.
Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural; Interface, 2015, 6 pages.
Al-Kaisy et al., Poster: "High-Frequency Spinal Cord Stimulation at 10 kHz for the Treatment of Chronic Back Pain Patients without Prior Back Surgery," 1 page.
Bara et al., Poster re: High Frequency Spinal Cord Stimulation for Dominant Back Pain—1 year follow up, 2013, 1 page.
Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.
BionicNAVIGATOR Software Guide, Part MP9055261-001, 2004, 58 pages.
Broseta et al., "High-Frequency cervical spinal cord stimulation in spasticity and motor disorders," Advances in Stereotactic and Functional Neurosurgery 7. Springer Verlag 1987, 6 pages.
Cahana et al., "Acute Differential Modulation of Synaptic Transmission and Cell Survival During Exposure to Pulsed and Continuous Radiofrequency; Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
Crapanzano et al., "High Frequency Spinal Cord Stimulation for Complex Regional Pain Syndrome: A Case Report," Pain Physician, 2017, 6 pages.
De Carolis et al., Poster: "Efficacy of Spinal Cord Stimulation (SCS) in the Treatment of Failed Back Surgery Syndrome (FBSS): a comparative study," 2013, 1 page.
Decision and Minutes: Opposition of European Patent No. 2421600 by Boston Scientific Neuromodulation Corporation, Apr. 3, 2017, 28 pages.
Geddes, "A Short History of the electrical stimulation of excitable tissue—Including Electrotherapeutic Applications," The Physiologist, vol. 27, No. 1, Feb. 1984, 51 pages.
Gulve et al., Poster: "10kHz High Frequency Spinal Cord Stimulation: Middlesbrough Experience," 2013, 1 page.
Higuchi et al., "Exposure of the Dorsal Root Ganglion in Rats to Pulsed Radiofrequency Currents Activates Dorsal Horn Lamina I and II Neurons,"; Neurosurgery, vol. 50, No. 4, Apr. 2002, 7 pages.
House et al., "Safety and Efficacy of the House/3M Cochlear Implant in Profoundly Deaf Adults," Otolaryngologic Clinics of North America, vol. 19, No. 2, May 1986, 12 pages.
International Neuromodulation Society 10th World Congress, Neuromodulation: Technology that Improves Patient Care, London, England, May 21-26, 2011, 385 pages.
Jacques et al., "Development of a New Implantable Bio-Telestimulator," Surg. Neurol., vol. 13, May 1980, 2 pages.
Jezernik et al., "Electrical Stimulation for the Treatment of Bladder; Dysfunction: Current Status and Future Possibilities," Neurological Research, vol. 24, Jul. 2002, 18 pages.
Kapural et al., "Comparison of 10-kHz High Frequency and Traditional Low-Frequency Spinal Cord Stimulation for the Treatment

(56) References Cited

OTHER PUBLICATIONS of Chronic Back ; and Leg Pain: 24-Month Results From a Multi-center, Randomized, Controlled Pivotal Trial," Neurosurgery, vol. 79, No. 5, Nov. 2016, 11 pages.

Lambru et al., "Safety and Efficacy of Cervical 10 kHz Spinal Cord Stimulation in Chronic Refractory Primary Headaches: A Retrospective Case Series," The Journal of Headache and Pain, 2016, 8 pages.

Mavoori et al., "An Autonomous implantable computer for neural recording and stimulation in unrestrained primates," Journal of Neuroscience Methods, 2005, 7 pages.

Meyerson et al., Mechanisms of spinal cord stimulation in neuropathic pain, Neurological Research, vol. 22, Apr. 2000, 5 pages.

Miller, Jonathan, "Parameters of Spinal Cord Stimulation and Their Role in Electrical Charge Delivery: A Review," Neuromodulation: Technology at the Neural Interface, 2016.

Mounaïm et al., "New Neurostimulation Strategy and Corresponding Implantable Device to Enhance Bladder Functions," Biomedical Engineering Trends in Electronics, Communications and Software, Chapter 5, 2011, 15 pages.

Mueller et al., "The Med-El Sonatati 100 Cochlear Implant: An evaluation of its safety in adults and children," Acta Oto-Laryngologica, vol. 131, No. 5, 2011, 8 pages.

NIDCD-NIH 2011, Cochlear Implant Brochure, http://www.nidcd.nih.gov/health/hearing/pages/coch.aspx, Jun. 29, 2012, 2 pages.

North et al., "Spinal Cord Stimulation With Interleaved Pulses: A ; Randomized, Controlled Trial," vol. 10, No. 4, 2007, 9 pages.

Notice of Opposition to a European Patent for European Patent No. 2853285, Proprietor of the Patent: Nevro Corporation; Opponent: Medtronic, Inc., Apr. 19, 2017, 40 pages.

OHSIPP Summer Newsletter, The Official Newsletter for the Ohio Society of Interventional Pain Physicians, vol. 1 Ed. 2, Summer 2010, 8 pages.

Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.

Precision—Physician System Handbook, Advanced Bionic Corporation, Part 9055253-0001, 2005, 92 pages.

Precision—Physician Trail Kit Insert, Advanced Bionic Corporation, Part 9055258-0001, 2005, 2 pages.

Precision Spinal Cord Stimulation—Charging System Insert, Advanced Bionic Corporation, Part 9055074-0001, 2004, 2 pages.

Precision Spinal Cord Stimulation—Charging System, Advanced Bionic Corporation, Part 9055259-0001, 2004, 2 pages.

Precision Spinal Cord Stimulation—Patient System Handbook, Advanced Bionic Corporation, Part 9055072-0001, 2004, 93 pages.

Precision Spinal Cord Stimulation—Patient Trial Journal, Advanced Bionic Corporation, Part 9055260-0001, 2004, 10 pages.

Precision Spinal Cord Stimulation—Physician Implant Manual, Advanced Bionic Corporation, Part 9055100, 2004, 62 pages.

Precision Spinal Cord Stimulation—Physician Implant Manual, Advanced Bionic Corporation, Part 9055255-0001, 2005, 70 pages.

Precision Spinal Cord Stimulation—Physician Lead Manual, Advanced Bionic Corporation, Part No. 9055183-001, May 2004, 31 pages.

Precision Spinal Cord Stimulation—Physician Lead Manual, Advanced Bionic Corporation, Part 9055095, 2004, 62 pages.

Precision Spinal Cord Stimulation—Physician Lead Manual, Advanced Bionic Corporation, Part 9055256-0001, 2005, 56 pages.

Precision Spinal Cord Stimulation—Physician Trail Handbook, Advanced Bionic Corporation, Part 9055254-0001, 2005, 66 pages.

Precision Spinal Cord Stimulation—Physician Trail Kit Model SC-7005, Part 9055066-001, Advanced Bionic Corporation, 2004, 2 pages.

Precision Spinal Cord Stimulation—Remote Control Model SC-5200, Part 9055107-001, 2004, Advanced Bionic Corporation, 2 pages.

Precision Spinal Cord Stimulation—Remote Control Model SC-5210, Advanced Bionic Corporation, Part 9055257-001, 2005, 2 pages.

Precision Spinal Cord Stimulation System—Patient System Handbook, Advanced Bionic Corporation, Part No. 9055184-001, May 2004, 86 pages.

Precision Spinal Cord Stimulation System, Patient Trial Handbook, Part 9055078, 2004, 74 pages.

Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.

Pudenz et al., "Neural Stimulation: Clinical and Laboratory Experiences", Surg. Neurol, 39:235-242 (1993).

Rapcan et al., Clinical Study, "High-Frequency—Spinal Cord Stimulation," Indexed and Abstracted in Science Citation Index Expanded and in Journal Citation Reports, 2015, 3 pages.

Schulman et al., "Battery Powered BION FES Network," Proceedings of the 26th Annual Conference of the IEEE EMBS, San Francisco, CA., Sep. 1-5, 2004, 4 pages.

Shealy et al., "Dorsal Column Electrohypalgesia," Jul. 1969, 8 pages.

Shelden et al., "Depolarization in the Treatment of Trigeminal Neuralgia," Evaluation of Compression and Electrical Methods; Clinical Concept of Neurophysiological Mechanism, 1966, 8 pages.

Shelden et al., "Development and Clinical Capabilities of a New Implantable Biostimulator," The American J. of Surgery, vol. 124, Aug. 1972, 6 pages.

Shelden et al., Electrical Control of Facial Pain, Am. J. of Surgery, vol. 114, Aug. 1967, 6 pages.

Shelden et al., "Electrical stimulation of the nervous system," Surg. Neurol. vol. 4, No. 1, Jul. 1975, 6 pages.

Smet et al,., "Successful Treatment of Low Back Pain with a Novel Neuromodulation Device," AZ Nikolaas, 12 pages.

Smet et al., Poster: "High-Frequency Spinal Cord Stimulation at 10 kHz after Failed Traditional Spinal Cord Stimulation," NANS, 2013, 1 page.

Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.

Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.

Van Buyten et al., "Pain Relief for Axial Back Pain Patients," INS Meeting; Poster, 1 page.

Verrills et al., "Peripheral Nerve Field Stimulation for Chronic Pain: 100 Cases and Review of the Literature," Pain Medicine, 2011, 11 pages.

Verrills et al., "Salvaging Failed Neuromodulation Implants with Nevro High Frequency Spinal Cord System," NANS Poster, 2013, 1 page.

Von Korff et al., "Assessing Global Pain Severity by Self-Report in Clinical and Health Services Research," SPINE, vol. 25, No. 24, 2000, 12 pages.

Ward et al., "Electrical Stimulation Using Kilohertz-Frequency Alternating Current," Journal of the American Physical Therapy Association, vol. 89, No. 2, Feb. 2009, 12 pages.

Ward et al., "Variation in Motor Threshold with Frequency Using kHz Frequency Alternating Current," Muscle and Nerve, Oct. 2001, 9 pages.

Weinberg et al., "Increasing the oscillation frequency of strong magnetic fields above 101 kHz significantly raises peripheral nerve excitation thresholds," Medical Physics Letter, May 2012, 6 pages.

Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.

(56) References Cited

OTHER PUBLICATIONS

Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Defendant's Boston Scientific Corporation's and Boston Scientific Neuromodulation Corporation's Preliminary Invalidity Contentions, Case No. 3:16-cv-06830-VC, filed Mar. 17, 2017, 159 pages.
Exhibit A1: *Invalidity Chart* v. *MacDonald* (U.S. Pat. No. 5,776,170), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 294 pages.
Exhibit A2: *Invalidity Chart* v. *Spinner* (U.S. Patent Application Publication No. 2007/0213771), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 235 pages.
Exhibit A3: *Invalidity Chart* v. *Knudson* (U.S. Patent Application Publication No. 2007/0073354), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 301 pages.
Exhibit A4: *Invalidity Chart* v. *Butukhanov* (Soviet Union Publication No. 1512625), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 233 pages.
Exhibit A5: *Invalidity Chart* v. *Sluijter* (U.S. Pat. No. 6,246,912), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 226 pages.
Exhibit A6: *Invalidity Chart* v. *Kilgore* (U.S. Pat. No. 7,389,145), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 219 pages.
Exhibit A7: *Invalidity Chart* v. *Royle* (U.S. Patent Application Publication No. 2006/0009820), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 188 pages.
Exhibit A8: *Invalidity Chart* v. *King* (U.S. Patent Application Publication No. 2007/0149148), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 222 pages.
Exhibit A9: *Invalidity Chart* v. *DeRidder* (U.S. Patent Application Publication No. 2011/0184488), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 266 pages.
Exhibit A10: *Invalidity Chart* v. *Fang* (U.S. Patent Application Publication No. 2009/0204173), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 191 pages.
Exhibit B1: *Invalidity Chart* v. *Boston Scientific's Precision Spinal Cord Stimulation System,* Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 337 pages.
Exhibit C1: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 400 pages.
Declaration of Rafael Carbunaru in Support of Boston Scientific's Invalidity Contentions, *Nevro Corp.* (Plaintiff) vs. *Boston Scientific Corporation and Boston Scientific Neuromodulation Corporation,* Case No. 3:16-cv-06830-VC, executed Mar. 17, 2017, 5 pages.
Exhibit A of Declaration of Rafael Carbunaru: "Physician Implant Manual—Precision," in Support in Support of Defendants Boston Scientific Corporation's and Boston Scientific Neuromodulation Corporation's Invalidity Contentions, Advanced Bionics, 2004, 62 pages.
Exhibit B of Declaration of Rafael Carbunaru: "Physician Lead Manual—Precision," in Support in Support of Defendants Boston Scientific Corporation's and Boston Scientific Neuromodulation Corporation's Invalidity Contentions, Advanced Bionics, 2004, 62 pages.
Exhibit C of Declaration of Rafael Carbunaru: "Patient System Handbook—Precision," in Support in Support of Defendants Boston Scientific Corporation's and Boston Scientific Neuromodulation Corporation's Invalidity Contentions, Advanced Bionics, 2004, 93 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Yearwood et al., "Pulse Width Programming in Spinal Cord Stimulation: A Clinical Study," Pain Physician Journal, Jul./Aug. 2010, 16 pages.
De Ridder et al., Copy of U.S. Appl. No. 60/895,061, Applicant: Dirk De Ridder, filed Mar. 15, 2007, 47 pages.
Boston Scientific's Answer to First Amended Complaint and Defense, *Nevro Corp.* vs. *Boston Scientific Corporation and Boston Scientific Neuromodulation Corporation,* Case No. 3:16-cv-06830-Vc, Jul. 13, 2017, 22 pages.
Defendant's First Amended Preliminary Invalidity Contentions, *Nevro Corp.* v. *Boston Scientific Corporation and Boston Scientific Neuromodulation Corporation,* Case No. 3:16-cv-06830-VC, Jun. 17, 2017, 93 pages.
First Amended Complaint for Patent Infringement and Declaratory Judgment, *Nevro Corp.* v. *Boston Scientific Corporation and Boston Scientific Neuromodulation Corporation,* Case No. 3:16-cv-06830-VC, Jun. 29, 2017, 45 pages.
Amended Exhibit C1 (amendments redlined): 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N. D. Cal.), Jun. 13, 2017, 423 pages.
Plaintiff Nevro Corp's Motion to Strike Inequitable Conduct Allegations From Defendants' Twelfth Affirmative Defense; Memorandum of Points and Authorities, *Nevro Corp.* vs. *Boston Scientific Corporation and Boston Scientific Neuromodulation Corporation,* Case No. 3:16-cv-06830-VC, Aug. 3, 2017, 10 pages.
Boston Scientific's Opposition to Nevro's Motion to Strike Inequitable Conduct Allegations from Defendants' Twelfth Affirmative Defense (ECF No. 172), *Nevro Corp.* vs. *Boston Scientific Corporation and Boston Scientific Neuromodulation Corporation,* Case No. 3:16-cv-06830-VC, Aug. 17, 2017, 17 pages.
Defendant's Second Amended Preliminary Invalidity Contentions, *Nevro Corp.* vs. *Boston Scientific Corporation and Boston Scientific Neuromodulation Corporation,* Case No. 3:16-cv-06830-VC, Aug. 10, 2017, 108 pages.

(56) References Cited

OTHER PUBLICATIONS

Exhibit A1 for Defendant's Second Amended Preliminary Invalidity Contentions: *Invalidity Chart v. MacDonald* (U.S. Pat. No. 5,776,170), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 168 pages.

Exhibit A2 for Defendant's Second Amended Preliminary Invalidity Contentions: *Invalidity Chart v. Spinner* (U.S. Patent Application Publication No. 2007/0213771), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 129 pages.

Exhibit A3 for Defendant's Second Amended Preliminary Invalidity Contentions: *Invalidity Chart v. Knudson* (U.S. Patent Application Publication No. 2007/0073354), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 173 pages.

Exhibit A5 for Defendant's Second Amended Preliminary Invalidity Contentions: *Invalidity Chart v. Sluijter* (U.S. Pat. No. 6,246,912), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 135 pages.

Exhibit A6 for Defendant's Second Amended Preliminary Invalidity Contentions: *Invalidity Chart v. Kilgore* (U.S. Pat. No. 7,389,145), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 110 pages.

Exhibit A7 for Defendant's Second Amended Preliminary Invalidity Contentions: *Invalidity Chart v. Royle* (U.S. Patent Application Publication No. 2006/0009820), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 111 pages.

Exhibit A9 for Defendant's Second Amended Preliminary Invalidity Contentions: *Invalidity Chart v. DeRidder* (U.S. Patent Application Publication No. 2011/0184488), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 160 pages.

Exhibit A10 for Defendant's Second Amended Preliminary Invalidity Contentions: *Invalidity Chart v. Fang* (U.S. Patent Application Publication No. 2009/0204173), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 114 pages.

Exhibit A11 for Defendant's Second Amended Preliminary Invalidity Contentions: *Invalidity Chart v. Alataris* (U.S. Pat. No. 8,712,533), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 13 pages.

Exhibit A12 for Defendant's Second Amended Preliminary Invalidity Contentions: *Invalidity Chart v. Gaunt* (U.S. Patent Publication No. 2006/0184211), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 113 pages.

Exhibit B1 for Defendant's Second Amended Preliminary Invalidity Contentions: *Invalidity Chart v. Boston Scientific's Precision Spinal Cord Stimulation System, Boston Scientific Corporation's and Boston Scientific Neuromodulation Corporation's Invalidity Contentions, Nevro Corp. v. Boston Scientific Corporation and Boston Scientific Neuromodulation Corporation*, Case No. 3:16-cv-06830-VC (N.D. Cal.), Aug. 10, 2017, 180 pages.

Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 174 pages.

Corrected Exhibit C1 for Defendant's Second Amended Preliminary Invalidity Contentions: 35 U.S.C. § 103(a) Invalidity Chart, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Aug. 10, 2017, 171 pages.

Statement of Grounds of Appeal for the Opposition of European Patent No. 2421600 (Appeal No. T1450/17-3.4.01) by Boston Scientific Neuromodulation Corporation, Aug. 14, 2017, 17 pages.

Nevro's Notice of Appeal for Opposition by Medtronic, Inc., and Boston Scientific Neuromodulation Corporation for European Patent No. 2243510, dated Aug. 3, 2017, 1 page.

Provision of a Copy of Minutes in accordance with Rule 124(4) EPC for Opposition by Medtronic, Inc., and Boston Scientific Neuromodulation Corporation for European Patent No. 2243510, dated Jul. 27, 2017, 23 pages.

Decision Revoking the European Patent for Opposition by Medtronic, Inc., and Boston Scientific Neuromodulation Corporation for European Patent No. 2243510, dated Jul. 27, 2017, 37 pages.

Nevro's Reply of the Patentee to the Notices of Opposition filed by Medtronic, Inc., and Boston Scientific Neuromodulation Corporation for EP2853285, filed Nov. 3, 2017, 34 pages.

Nevro's Statement of Grounds of Appeal for EP2243510 (Appeal No. T 17484/17-3.4.01), filed Nov. 30, 2017, 16 pages.

Abejon et al., "Is Impedance a Parameter to be Taken into Account in Spinal Cord Stimulation?" Pain Physician, 2007, 8 pages.

Alo et al., "Factors Affecting Impedance of Percutaneous Leads in Spinal Cord Stimulation," International Neuromodulation Society, vol. 9, No. 2, 2006, 8 pages.

Bronstein et al., "The Rationale Driving the Evolution of Deep Brain Stimulation of Constant-Current Devices," International Neuromodulation Society 2014, 5 pages.

McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.

McCreery et al., "Damage in Peripheral Nerve from Continuous Electrical Stimulation: Comparison of Two Stimulus Waveforms," Medical and Biological Engineering and Computing, Jan. 1992, 6 pages.

McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.

Notice of Opposition to a European Patent, Copy of Argument and Facts, for European Patent No. 2586488, Proprietor of the Patent: Nevro Corporation Opponent: Boston Scientific Neuromodulation Corporation, Dec. 15, 2017, 35 pages.

Opponents Boston Scientific Neuromodulation Corporation: Response to Nov. 9, 2017 Brief Communication in Opposition for European Patent No. 2853285, dated Feb. 13, 2018, 9 pages.

Opponents Medtronic, Inc.: Facts and Arguments in Support of Opposition for European Patent No. 2586488, dated Dec. 15, 2017, 18 pages.

(56) References Cited

OTHER PUBLICATIONS

Rosenblueth et al., "The Blocking and Deblocking Effects of Alternating Currents on Nerve," Department of Physiology in Harvard Medical School, Nov. 1938, 13 pages.
St. Jude Medical, "Clinician's Manual—Percutaneous Lead Kit, Models 3143, 3146, 3149, 3153, 3156, 3159, 3183, 3186, 3189," 2016, 24 pages.
Wesselink et al., Analysis of Current Density and Related Parameters in Spinal Cord Stimulation, IEEE Transaction on Rehabilitation Engineering vol. 6, No. 2, Jun. 1998, 8 pages.
U.S. Appl. No. 14/534,769, filed Nov. 6, 2014, Park.
U.S. Appl. No. 15/606,869, filed May 26, 2017, Lee.
Nevro's Motion for Summary Adjudication—Notice of Motion, Motion and Memorandum of Points and Authorities in the Support of Nevro's Motion for Summary Adjudication (Document 461), *Nevro Corp. vs. Boston Scientific Corporation and Boston Scientific Neuromodulation Corporation*, Case No. 3:16-cv-06830-VC-MEJ, filed Jul. 30, 2018, 50 pages.
Declaration of Konstantinos Alataris in Support of Nevro's Motion of Summary Adjudication (Document 342-1), *Nevro Corp. vs. Boston Scientific Corporation and Boston Scientific Neuromodulation Corporation*, Case No. 3:16-cv-06830-VC-MEJ, Apr. 11, 2018, 3 pages.
Exhibit 1 for Declaration of Konstantinos Alataris in Support of Nevro's Motion of Summary Adjudication (Document 342-2), Notes from NBI Mayo Physician Meeting Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), Apr. 12, 2018, 3 pages.
Exhibit 2 for Declaration of Konstantinos Alataris in Support of Nevro's Motion of Summary Adjudication (Document 342-3), Notes from NBI Development—Mayo Clinic Dec. 4, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 3 for Declaration of Konstantinos Alataris in Support of Nevro's Motion of Summary Adjudication (Document 342-4), Sep. 2007 Email between O. Filho and Konstantinos Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 4 for Declaration of Konstantinos Alataris in Support of Nevro's Motion of Summary Adjudication (Document 342-5) NBI Development Inc., Jun. 12, 2007 Board Meeting, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 31 pages.
Declaration of Ben Pless in Support of Nevro's Motion for Summary Adjudication (Updated Redacted Version of EFC No. 347-24), *Nevro Corp. vs. Boston Scientific Corporation and Boston Scientific Neuromodulation Corporation*, Case No. 3:16-cv-06830-VC-MEJ, Apr. 11, 2018, 64 pages.
Exhibit A for Declaration of Ben Pless in Support of Nevro's Motion for Summary Adjudication (Document 342-7) Curriculum Vitae of Benjamin Pless, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 15 pages.
Declaration of Eric C. Pai in Support of Nevro's Motion for Summary Adjudication (Document 343), *Nevro Corp. vs. Boston Scientific Corporation and Boston Scientific Neuromodulation Corporation*, Case No. 3:16-cv-06830-VC-MEJ, Apr. 12, 2018, 11 pages.
Exhibit 1 for Declaration of Eric C. Pai in Support of Nevro's Motion for Summary Adjudication (Document 343-1) Chart—Asserted Claims with Disputed Terms Underlined, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 2 for Declaration of Eric C. Pai in Support of Nevro's Motion for Summary Adjudication (Document 343-2) Certified Copy of U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 3 for Declaration of Eric C. Pai in Support of Nevro's Motion for Summary Adjudication (Document 343-3) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 4 for Declaration of Eric C. Pai in Support of Nevro's Motion for Summary Adjudication (Document 343-4) Certified Copy of U.S. Pat. No. 8,768,472, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 37 pages.
Exhibit 5 for Declaration of Eric C. Pai in Support of Nevro's Motion for Summary Adjudication (Document 343-5) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 35 pages.
Exhibit 6 for Declaration of Eric C. Pai in Support of Nevro's Motion for Summary Adjudication (Document 343-6) Certified Copy of U.S. Pat. No. 9,327,125, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 40 pages.
Exhibit 7 for Declaration of Eric C. Pai in Support of Nevro's Motion for Summary Adjudication (Document 343-7) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 39 pages.
Exhibit 8 for Declaration of Eric C. Pai in Support of Nevro's Motion for Summary Adjudication (Document 343-8) Certified Copy of U.S. Pat. No. 9,480,842, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 38 pages.
Exhibit 9 for Declaration of Eric C. Pai in Support of Nevro's Motion for Summary Adjudication (Document 343-9) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 10 for Declaration of Eric C. Pai in Support of Nevro's Motion for Summary Adjudication (Document 343-10) Article by Antonio Foletti et al., Boston Scientific Corporation's and Boston Scientific Neuromodulation Corporation's Invalidity Contentions, *Nevro Corp. v. Boston Scientific Corporation and Boston Scientific*

(56) References Cited

OTHER PUBLICATIONS

*Neuromodulation Corporation*, Case No. 3:16-cv-06830-VC (N.D. Cal.), filed Apr. 12, 2018, 15 pages.
Exhibit 11 for Declaration of Eric C. Pai in Support of Nevro's Motion for Summary Adjudication (Document 343-11) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 12 for Declaration of Eric C. Pai in Support of Nevro's Motion for Summary Adjudication (Document 343-12) Poster by Mark Wallace et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 2 pages.
Exhibit 13 for Declaration of Eric C. Pai in Support of Nevro's Motion for Summary Adjudication (Document 343-13) Summary of Safety and Effectiveness Data (SSED), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 14 for Declaration of Eric C. Pai in Support of Nevro's Motion for Summary Adjudication (Document 343-14) Nevro—Notes from Las Vegas and Our Survey of 50 US pain docs, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 19 pages.
Exhibit 15 for Declaration of Eric C. Pai in Support of Nevro's Motion for Summary Adjudication (Document 343-15) Apr. 2012 Email between K. Bradley and J. Cassidy, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 16 for Declaration of Eric C. Pai in Support of Nevro's Motion for Summary Adjudication (Document 343-16) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 17 for Declaration of Eric C. Pai in Support of Nevro's Motion for Summary Adjudication (Document 343-17) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 18 for Declaration of Eric C. Pai in Support of Nevro's Motion for Summary Adjudication (Document 343-18) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 19 for Declaration of Eric C. Pai in Support of Nevro's Motion for Summary Adjudication (Document 343-19) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 pages.
Exhibit 20 for Declaration of Eric C. Pai in Support of Nevro's Motion for Summary Adjudication (Document 343-20) Redacted Version of Document Sought to be Sealed—Excerpts from May 18, 2018 Deposition of R. Carbunaru, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 21 for Declaration of Eric C. Pai in Support of Nevro's Motion for Summary Adjudication (Document 343-21) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.
Exhibit 22 for Declaration of Eric C. Pai in Support of Nevro's Motion for Summary Adjudication (Document 462) Updated Redacted Version of ECF No. 347-10—Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 9 pages.
Exhibit 23 for Declaration of Eric C. Pai in Support of Nevro's Motion for Summary Adjudication (Document 463) Updated Redacted Version of ECF No. 347-12, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 23 pages.
Exhibit 24 for Declaration of Eric C. Pai in Support of Nevro's Motion for Summary Adjudication (Document 343-24) Redacted Version of Document Sought to Be Sealed—BSC's Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.
Exhibit 25 for Declaration of Eric C. Pai in Support of Nevro's Motion for Summary Adjudication (Document 464) Updated Redacted Version of ECF No. 347-16—BSC's Second Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 26 for Declaration of Eric C. Pai in Support of Nevro's Motion for Summary Adjudication (Document 343-26) Decision Denying Institution of Inter Partes Review 37 CFR § 42.108—IPR2015-01203 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 21 pages.
Exhibit 27 for Declaration of Eric C. Pai in Support of Nevro's Motion for Summary Adjudication (Document 343-27) Decision Denying Institution of Inter Partes Review 37 CFR § 42.108—IPR2015-01204 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.
Exhibit 28 for Declaration of Eric C. Pai in Support of Nevro's Motion for Summary Adjudication (Document 343-28) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 29 for Declaration of Eric C. Pai in Support of Nevro's Motion for Summary Adjudication (Document 343-29) Rebuttal Expert Report and Declaration of Gene Fridman, Ph.D., regarding Claim Construction—Feb. 14, 2018, Boston Scientific Corporation's and Boston Scientific Neuromodulation Corporation's Invalidity Contentions, *Nevro Corp. v. Boston Scientific Corporation*

(56) References Cited

OTHER PUBLICATIONS and Boston Scientific Neuromodulation Corporation, Case No. 3:16-cv-06830-VC (N.D. Cal.), filed Apr. 12, 2018, 13 pages.
Exhibit 30 for Declaration of Eric C. Pai in Support of Nevro's Motion for Summary Adjudication (Document 343-30) Deposition of Dr. Gene Fridman on Mar. 7, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 49 pages.
Exhibit 31 for Declaration of Eric C. Pai in Support of Nevro's Motion for Summary Adjudication (Document 343-31) Rebuttal Expert Report and Declaration of Gene Fridman, Ph.D., regarding Claim Construction—Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 32 for Declaration of Eric C. Pai in Support of Nevro's Motion for Summary Adjudication (Document 343-32) Deposition of Kaoru Lee Adair—May 10, 2017, Entire Document Sought to be Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 33 for Declaration of Eric C. Pai in Support of Nevro's Motion for Summary Adjudication (Document 343-33) Expert Report and Declaration of Adam Lipson, M.D., pursuant to Federal Rule of Civil Procedure 26(A)(2)(B) dated Jan. 18, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 34 for Declaration of Eric C. Pai in Support of Nevro's Motion for Summary Adjudication (Document 343-34) Stedman's Medical Dictionary 27th Edition, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 35 for Declaration of Eric C. Pai in Support of Nevro's Motion for Summary Adjudication (Document 343-35) Dorland's Illustrated Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 36 for Declaration of Eric C. Pai in Support of Nevro's Motion for Summary Adjudication (Document 343-36) Mosby's Medical Dictionary, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 37 for Declaration of Eric C. Pai in Support of Nevro's Motion for Summary Adjudication (Document 343-37) National Institute of Neurological Disorders and Stroke—Paresthesia Information Page, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 38 for Declaration of Eric C. Pai in Support of Nevro's Motion for Summary Adjudication (Document 343-38) Videotaped Deposition of Richard T. Mihran, Ph.D. on Mar. 12, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.
Exhibit 39 for Declaration of Eric C. Pai in Support of Nevro's Motion for Summary Adjudication (Document 343-39) Boston Scientific—Precision Spinal Cord Stimulator System with MultiWave Technology Clinician Manual,, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 68 pages.
Exhibit 40 for Declaration of Eric C. Pai in Support of Nevro's Motion for Summary Adjudication (Document 343-40) BSC's Amended and Supplemental Responses and Objections to Nevro's Second Set of Interrogatories (Nos. 9, 10) dated Aug. 24, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 18 pages.
Exhibit 41 for Declaration of Eric C. Pai in Support of Nevro's Motion for Summary Adjudication (Document 343-41) Rebuttal Expert Report of Richard T. Mihran, Ph.D. dated Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 23 pages.
Exhibit 42 for Declaration of Eric C. Pai in Support of Nevro's Motion for Summary Adjudication (Document 343-42) Redacted Version of Document Sought to be Sealed—Videotaped Deposition of Nevro Corp. with designated corporate representative Jim Cassidy on May 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 43 for Declaration of Eric C. Pai in Support of Nevro's Motion for Summary Adjudication (Document 343-43) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 pages.
Exhibit 44 for Declaration of Eric C. Pai in Support of Nevro's Motion for Summary Adjudication (Document 343-44) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 45 for Declaration of Eric C. Pai in Support of Nevro's Motion for Summary Adjudication (Document 343-45) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 46 for Declaration of Eric C. Pai in Support of Nevro's Motion for Summary Adjudication (Document 343-46) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 47 for Declaration of Eric C. Pai in Support of Nevro's Motion for Summary Adjudication (Document 343-47) Entire Document Sought to be Sealed—Deposition of Kaoru Lee Adair taken on

(56) References Cited

OTHER PUBLICATIONS

May 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 48 for Declaration of Eric C. Pai in Support of Nevro's Motion for Summary Adjudication (Document 343-48) Defendant's Identification of 40 Prior Art Grounds for Invalidity dated Dec. 22, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 49 for Declaration of Eric C. Pai in Support of Nevro's Motion for Summary Adjudication (Document 343-49) Defendants Second Amended Preliminary Invalidity Contentions dated Aug. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 47 pages.
Exhibit 50 for Declaration of Eric C. Pai in Support of Nevro's Motion for Summary Adjudication (Document 343-50) Declaration of Rafael Carbunaru in Support of Boston Scientific's Invalidity Contentions dated Mar. 17, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 51 for Declaration of Eric C. Pai in Support of Nevro's Motion for Summary Adjudication (Document 343-51) Declaration of Kaoru Lee Adair in Support of Boston Scientific's Motion to Dismiss Nevro's Declaratory Judgment Claims dated Dec. 27, 2016, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Exhibit 52 for Declaration of Eric C. Pai in Support of Nevro's Motion for Summary Adjudication (Document 343-52) Expert Report of Richard T. Mihran, Ph.D., regarding Invalidity of U.S. Pat. Nos. 8,712,533; 9,327,125; 8,359,102; 9,480,842; 9,333,357; 8,792,988; and 8,768,472 dated Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 78 pages.
Exhibit 53 for Declaration of Eric C. Pai in Support of Nevro's Motion for Summary Adjudication (Document 343-53) Redacted Version of Document Sought to be Sealed—Rebuttal Expert Report and Declaration of Daniel Lanovaz dated Feb. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 54 for Declaration of Eric C. Pai in Support of Nevro's Motion for Summary Adjudication (Document 343-54) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 55 for Declaration of Eric C. Pai in Support of Nevro's Motion for Summary Adjudication (Document 343-55) Copy of U.S. Patent Application No. 2009/0204173 to Fang et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 33 pages.
Exhibit 56 for Declaration of Eric C. Pai in Support of Nevro's Motion for Summary Adjudication (Document 343-56) Deposition of Konstantinos Alataris dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 57 for Declaration of Eric C. Pai in Support of Nevro's Motion for Summary Adjudication (Document 343-57) Videotaped Deposition of Andre B. Walker dated Nov. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 26 pages.
Exhibit 58 for Declaration of Eric C. Pai in Support of Nevro's Motion for Summary Adjudication (Document 343-58) Videotaped Deposition of Zi-Ping Fang dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 59 for Declaration of Eric C. Pai in Support of Nevro's Motion for Summary Adjudication (Document 343-59) Videotaped Deposition of Anthony Vincent Caparso dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 60 for Declaration of Eric C. Pai in Support of Nevro's Motion for Summary Adjudication (Document 343-60) Videotaped Deposition of Brian Erickson dated Dec. 15, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 44 pages.
Exhibit 61 for Declaration of Eric C. Pai in Support of Nevro's Motion for Summary Adjudication (Document 343-61) Deposition of Yougandh Chitre dated Nov. 20, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 62 for Declaration of Eric C. Pai in Support of Nevro's Motion for Summary Adjudication (Document 343-62) Deposition of Sangsoo Wesley Park dated Nov. 27, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 63 for Declaration of Eric C. Pai in Support of Nevro's Motion for Summary Adjudication (Document 343-63) Deposition of Jon Parker dated Nov. 16, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 64 for Declaration of Eric C. Pai in Support of Nevro's Motion for Summary Adjudication (Document 343-64) Videotaped James Thacker dated Dec. 7, 2017 (vol. 1), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.

(56) References Cited

OTHER PUBLICATIONS

Exhibit 65 for Declaration of Eric C. Pai in Support of Nevro's Motion for Summary Adjudication (Document 343-65) Sep. 2007 Email between O. Filho and K. Alataris, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 4 pages.
Exhibit 66 for Declaration of Eric C. Pai in Support of Nevro's Motion for Summary Adjudication (Document 343-66) Redacted Version of Document Sought to be Sealed—BSC's Dec. 1, 2017 Supplemental Responses and Objections to Nevro's Second Set of Interrogatories (Nos. 10 and 14), Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 13 pages.
Exhibit 67 for Declaration of Eric C. Pai in Support of Nevro's Motion for Summary Adjudication (Document 343-67) Certified Copy of U.S. Appl. No. 60/985,353, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 63 pages.
Exhibit 68 for Declaration of Eric C. Pai in Support of Nevro's Motion for Summary Adjudication (Document 343-68) Certified Copy of U.S. Appl. No. 12/264,836, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 67 pages.
Exhibit 69 for Declaration of Eric C. Pai in Support of Nevro's Motion for Summary Adjudication (Document 343-69) Certified Copy File Wrapper for U.S. Appl. No. 12/264,836, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 119 pages.
Exhibit 70 for Declaration of Eric C. Pai in Support of Nevro's Motion for Summary Adjudication (Document 343-70) Copy of Request to Add to Originally Named Inventors for U.S. Appl. No. 12/264,836, filed Aug. 13, 2012, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 27 pages.
Exhibit 71 for Declaration of Eric C. Pai in Support of Nevro's Motion for Summary Adjudication (Document 343-71) Poster by Yearwood et al., Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 8 pages.
Exhibit 72 for Declaration of Eric C. Pai in Support of Nevro's Motion for Summary Adjudication (Document 343-72) Case Report by Yearwood et al., Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 3 pages.
Exhibit 73 for Declaration of Eric C. Pai in Support of Nevro's Motion for Summary Adjudication (Document 343-73) Entire Document Sought to be Sealed—Deposition of Rafael Carbunaru taken on Nov. 14, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.
Exhibit 74 for Declaration of Eric C. Pai in Support of Nevro's Motion for Summary Adjudication (Document 343-74) Deposition of David Caraway dated Nov. 14, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 9 pages.
Exhibit 75 for Declaration of Eric C. Pai in Support of Nevro's Motion for Summary Adjudication (Document 343-75) Boston Scientific document, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 5 pages.
Declaration of Carson D. Anderson in Support of Nevro's Administrative Motion to File under Seal Portions of Nevro's Motion for Summary Adjudication and Supporting Documents (Document 348), *Nevro Corp.* vs. *Boston Scientific Corporation and Boston Scientific Neuromodulation Corporation*, Case No. 3:16-cv-06830-VC-MEJ, Apr. 16, 2018, 10 pages.
Exhibit A for Declaration of Carson D. Anderson in Support of Nevro's Administrative Motion to File under Seal Portions of Nevro's Motion for Summary Adjudication and Supporting Documents (Document 347-1) Redacted Version of Document Sought to Be Filed under Seal—Nevro's Notice of Motion, *Nevro Corp.* vs. *Boston Scientific Corporation and Boston Scientific Neuromodulation Corporation*, Case No. 3:16-cv-06830-VC-MEJ, Apr. 16, 2018, 50 pages.
Exhibit A—Updated—for Declaration of Carson D. Anderson in Support of Nevro's Administrative Motion to File under Seal Portions of Nevro's Motion for Summary Adjudication and Supporting Documents (Document 347-2 / Document 461) Redacted Version of Document Sought to Be Filed under Seal—Nevro's Motion for Summary Adjudication, *Nevro Corp.* vs. *Boston Scientific Corporation and Boston Scientific Neuromodulation Corporation*, Case No. 3:16-cv-06830-VC-MEJ, Jul. 30, 2018, 50 pages.
Exhibit B for Declaration of Carson D. Anderson in Support of Nevro's Administrative Motion to File under Seal Portions of Nevro's Motion for Summary Adjudication and Supporting Documents (Document 347-3) Redacted Version of Document Sought to Be Filed under Seal—Videotaped Deposition of Rafael Carbunaru, Ph.D., taken Nov. 15, 2017, *Nevro Corp.* vs. *Boston Scientific Corporation and Boston Scientific Neuromodulation Corporation*, Case No. 3:16-cv-06830-VC-MEJ, filed Apr. 16, 2018, 46 pages.
Exhibit C for Declaration of Carson D. Anderson in Support of Nevro's Administrative Motion to File under Seal Portions of Nevro's Motion for Summary Adjudication and Supporting Documents (Document 347-5) Boston Scientific Neuromodulation—SPRINT High Rate—Product Opportunity Proposal, *Nevro Corp.* vs. *Boston Scientific Corporation and Boston Scientific Neuromodulation Corporation*, Case No. 3:16-cv-06830-VC-MEJ, filed Apr. 16, 2018, 14 pages.
Exhibit D for Declaration of Carson D. Anderson in Support of Nevro's Administrative Motion to File under Seal Portions of Nevro's Motion for Summary Adjudication and Supporting Documents (Document 347-7) Redacted Version of Document Sought to be Filed under Seal—Boston Scientific Neuromodulation—SPRINT High Rate—Project Authorization Review, *Nevro Corp.* vs. *Boston Scientific Corporation and Boston Scientific Neuromodulation Corporation*, Case No. 3:16-cv-06830-VC-MEJ, filed Apr. 16, 2018, 7 pages.
Exhibit E for Declaration of Carson D. Anderson in Support of Nevro's Administrative Motion to File under Seal Portions of Nevro's Motion for Summary Adjudication and Supporting Documents (Document 347-9) Redacted Version of Document Sought to be Filed under Seal—Videotaped Deposition of Kaoru Lee Adair, *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit E—Updated—for Declaration of Carson D. Anderson in Support of Nevro's Administrative Motion to File under Seal Portions of Nevro's Motion for Summary Adjudication and Supporting Documents (Document 347-10) Redacted Version of Docu-

(56) References Cited

OTHER PUBLICATIONS ment Sought to be Filed under Seal—Videotaped Deposition of Kaoru Lee Adair, taken Nov. 17, 2017, *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit F for Declaration of Carson D. Anderson in Support of Nevro's Administrative Motion to File under Seal Portions of Nevro's Motion for Summary Adjudication and Supporting Documents (Document 347-11) Redacted Version of Document Sought to be Filed under Seal—Videotaped Deposition of Kaoru Lee Adair, taken May 10, 2017, *Nevro Corp.* vs. *Boston Scientific Corporation and Boston Scientific Neuromodulation Corporation*, Case No. 3:16-cv-06830-VC-MEJ, filed Apr. 16, 2018, 23 pages.
Exhibit F—Updated—for Declaration of Carson D. Anderson in Support of Nevro's Administrative Motion to File under Seal Portions of Nevro's Motion for Summary Adjudication and Supporting Documents (Document 347-12) Redacted Version of Document Sought to be Filed under Seal—Videotaped Deposition of Kaoru Lee Adair, taken May 10, 2017, *Nevro Corp.* vs. *Boston Scientific Corporation and Boston Scientific Neuromodulation Corporation*, Case No. 3:16-cv-06830-VC-MEJ, filed Apr. 16, 2018, 23 pages.
Exhibit G for Declaration of Carson D. Anderson in Support of Nevro's Administrative Motion to File under Seal Portions of Nevro's Motion for Summary Adjudication and Supporting Documents (Document 347-13) BSC's Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit H for Declaration of Carson D. Anderson in Support of Nevro's Administrative Motion to File under Seal Portions of Nevro's Motion for Summary Adjudication and Supporting Documents (Document 347-15) Redacted Version of Document Sought to be Filed under Seal—BSC's Second Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit H—Updated—for Declaration of Carson D. Anderson in Support of Nevro's Administrative Motion to File under Seal Portions of Nevro's Motion for Summary Adjudication and Supporting Documents (Document 347-16) Updated Redacted Version of Document Sought to be Filed under Seal—BSC's Second Supplemental Responses and Objections to Nevro's First Set of Interrogatory Requests (1-8), *Nevro Corp.* vs. *Boston Scientific Corporation and Boston Scientific Neuromodulation Corporation*, Case No. 3:16-cv-06830-VC-MEJ, filed Apr. 16, 2018, 12 pages.
Exhibit I for Declaration of Carson D. Anderson in Support of Nevro's Administrative Motion to File under Seal Portions of Nevro's Motion for Summary Adjudication and Supporting Documents (Document 347-17) Redacted Version of Document Sought to be Filed under Seal—Rebuttal Expert Report of Richard T. Mihran, Ph.D., *Nevro Corp.* vs. *Boston Scientific Corporation and Boston Scientific Neuromodulation Corporation*, Case No. 3:16-cv-06830-VC-MEJ, filed Apr. 16, 2018, 24 pages.
Exhibit J for Declaration of Carson D. Anderson in Support of Nevro's Administrative Motion to File under Seal Portions of Nevro's Motion for Summary Adjudication and Supporting Documents (Document 347-19) Redacted Version of Document Sought to be Filed under Seal—Oct. 24, 2016 Boston Scientific Letter to U.S. Food and Drug Administration, *Nevro Corp.* vs. *Boston Scientific Corporation and Boston Scientific Neuromodulation Corporation*, Case No. 3:16-cv-06830-VC-MEJ, filed Apr. 16, 2018, 5 pages.
Exhibit K for Declaration of Carson D. Anderson in Support of Nevro's Administrative Motion to File under Seal Portions of Nevro's Motion for Summary Adjudication and Supporting Documents (Document 347-21) Redacted Version of Document Sought to be Filed under Seal—Rebuttal Expert Report and Declaration of Daniel Lanovaz dated Feb. 14, 2017, *Nevro Corp.* vs. *Boston Scientific Corporation and Boston Scientific Neuromodulation Corporation*, Case No. 3:16-cv-06830-VC-MEJ, filed Apr. 16, 2018, 7 pages.
Exhibit L for Declaration of Carson D. Anderson in Support of Nevro's Administrative Motion to File under Seal Portions of Nevro's Motion for Summary Adjudication and Supporting Documents (Document 347-23) Redacted Version of Document Sought to be Filed under Seal—Declaration of Ben Pless in Support of Nevro's Motion of Summary Adjudication dated Apr. 12, 2018, *Nevro Corp.* vs. *Boston Scientific Corporation and Boston Scientific Neuromodulation Corporation*, Case No. 3:16-cv-06830-VC-MEJ, filed Apr. 16, 2018, 64 pages.
Exhibit L—Updated—for Declaration of Carson D. Anderson in Support of Nevro's Administrative Motion to File under Seal Portions of Nevro's Motion for Summary Adjudication and Supporting Documents (Document 347-24) Updated Redacted Version of Document Sought to be Filed under Seal—Declaration of Ben Pless in Support of Nevro's Motion of Summary Adjudication dated Apr. 12, 2018, *Nevro Corp.* vs. *Boston Scientific Corporation and Boston Scientific Neuromodulation Corporation*, Case No. 3:16-cv-06830-VC-MEJ, filed Apr. 16, 2018, 64 pages.
Declaration of Rafael Carbunaru in Support of Nevro's Administrative Motion to File under Seal Portions of Nevro's Motion for Summary Adjudication and Supporting Documents (Document 34725), *Nevro Corp.* vs. *Boston Scientific Corporation and Boston Scientific Neuromodulation Corporation*, Case No. 3:16-cv-06830-VC-MEJ, filed Apr. 16, 2018, 13 pages.
[Proposed] Order Granting Administrative Motion to File under Seal Portions of Nevro's Administrative Motion to File under Seal Portions of Nevro's Motion for Summary Adjudication and Supporting Documents (ECF No. 341) (Document 347-26), *Nevro Corp.* vs. *Boston Scientific Corporation and Boston Scientific Neuromodulation Corporation*, Case No. 3:16-cv-06830-VC-MEJ, filed Apr. 16, 2018, 5 pages.
Boston Scientific's Responsive Claim Construction Brief, Opposition to Nevro's Motion for Summary Adjudication and Supporting Documents (Document 466), Updated Redacted Version of ECF No. 357-4, *Nevro Corp.* vs. *Boston Scientific Corporation and Boston Scientific Neuromodulation Corporation*, Case No. 3:16-cv-06830-VC-MEJ, filed Jul. 30, 2018, 61 pages.
Expert Report and Declaration of Gene Fridman, Ph.D., regarding Claim Construction (Document 358-1), *Nevro Corp.* vs. *Boston Scientific Corporation and Boston Scientific Neuromodulation Corporation*, Case No. 3:16-cv-06830-VC-MEJ, filed Apr. 26, 2018, 18 pages.
Rebuttal Expert Report and Declaration of Gene Fridman, Ph.D., regarding Claim Construction (Document 358-2), *Nevro Corp.* vs. *Boston Scientific Corporation and Boston Scientific Neuromodulation Corporation*, Case No. 3:16-cv-06830-VC-MEJ, filed Apr. 26, 2018, 11 pages.
Declaration of Richard T. Mihran, Ph.D., regarding Claim Construction Brief (Document 358-3), *Nevro Corp.* vs. *Boston Scientific Corporation and Boston Scientific Neuromodulation Corporation*, Case No. 3:16-cv-06830-VC-MEJ, filed Apr. 26, 2018, 2 pages.
Exhibit A for Declaration of Richard T. Mihran, Ph.D., regarding Claim Construction Brief (Document 358-4), Expert Report of Richard T. Mihran, Ph.D. regarding Invalidity of U.S. Pat. Nos. 8,712,533; 9,327,125; 8,359,102; 9,480,842; 9,333,357; 8,792,988; and 8,768,472, *Nevro Corp.* vs. *Boston Scientific Corporation and Boston Scientific Neuromodulation Corporation*, Case No. 3:16-cv-06830-VC-MEJ, filed Apr. 26, 2018, 129 pages.
Exhibit B Declaration of Richard T. Mihran, Ph.D., regarding Claim Construction Brief (Document 358-5), Redacted Version of Document Sought to be Filed under Seal—Rebuttal Expert Report of Richard T. Mihran, Ph.D., *Nevro Corp.* vs. *Boston Scientific Corporation and Boston Scientific Neuromodulation Corporation*, Case No. 3:16-cv-06830-VC-MEJ, filed Apr. 26, 2018, 79 pages.
Declaration of Clara W. Wang in Support of Boston Scientific's Responsive regarding Claim Construction Brief; Opposition to Nevro's Motion for Summary Judgement and Opening Motion for Summary Judgement (Document 358-6), *Nevro Corp.* vs. *Boston*

(56) References Cited

OTHER PUBLICATIONS

*Scientific Corporation and Boston Scientific Neuromodulation Corporation*, Case No. 3:16-cv-06830-VC-MEJ, filed Apr. 26, 2018, 8 pages.
Exhibit 1 for Declaration of Clara W. Wang in Support of Boston Scientific's Responsive regarding Claim Construction Brief; Opposition to Nevro's Motion for Summary Judgement and Opening Motion for Summary Judgement (Document 358-7), Sep. 2005 Email between K. Bradley and M. Moffitt, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 2 for Declaration of Clara W. Wang in Support of Boston Scientific's Responsive regarding Claim Construction Brief; Opposition to Nevro's Motion for Summary Judgement and Opening Motion for Summary Judgement (Document 358-8), Filed under Seal—Document NEVRO_BSXCA0165810-52, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 3 for Declaration of Clara W. Wang in Support of Boston Scientific's Responsive regarding Claim Construction Brief; Opposition to Nevro's Motion for Summary Judgement and Opening Motion for Summary Judgement (Document 358-9), Filed under Seal—Document NEVRO_BSXCA0389050-100, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 4 for Declaration of Clara W. Wang in Support of Boston Scientific's Responsive regarding Claim Construction Brief; Opposition to Nevro's Motion for Summary Judgement and Opening Motion for Summary Judgement (Document 358-10), Summary of Safety and Effectiveness Data (SSED), *Nevro Corp. vs. Boston Scientific Corporation and Boston Scientific Neuromodulation Corporation*, Case No. 3:16-cv-06830-VC-MEJ, filed Apr. 26, 2018, 57 pages.
Exhibit 5 for Declaration of Clara W. Wang in Support of Boston Scientific's Responsive regarding Claim Construction Brief; Opposition to Nevro's Motion for Summary Judgement and Opening Motion for Summary Judgement (Document 358-11), Article by Andres et al., *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 6 for Declaration of Clara W. Wang in Support of Boston Scientific's Responsive regarding Claim Construction Brief; Opposition to Nevro's Motion for Summary Judgement and Opening Motion for Summary Judgement (Document 358-12), Article by Thomson et al., *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 7 for Declaration of Clara W. Wang in Support of Boston Scientific's Responsive regarding Claim Construction Brief; Opposition to Nevro's Motion for Summary Judgement and Opening Motion for Summary Judgement (Document 358-13), Filed under Seal—Document labeled NEVRO_BSXCA0053540-89, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 8 for Declaration of Clara W. Wang in Support of Boston Scientific's Responsive regarding Claim Construction Brief; Opposition to Nevro's Motion for Summary Judgement and Opening Motion for Summary Judgement (Document 358-14), Filed under Seal—Document labeled NEVRO_BSXCA0055766-70, *Nevro Corp. vs. Boston Scientific Corporation and Boston Scientific Neuromodulation Corporation*, Case No. 3:16-cv-06830-VC-MEJ, filed Apr. 26, 2018, 1 pages.
Exhibit 9 for Declaration of Clara W. Wang in Support of Boston Scientific's Responsive regarding Claim Construction Brief; Opposition to Nevro's Motion for Summary Judgement and Opening Motion for Summary Judgement (Document 358-15), Filed under Seal—Document labeled NEVRO_BSXCA0049348-69, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 10 for Declaration of Clara W. Wang in Support of Boston Scientific's Responsive regarding Claim Construction Brief; Opposition to Nevro's Motion for Summary Judgement and Opening Motion for Summary Judgement (Document 358-16), Videotaped Deposition of Rafael Carbunaru, Ph.D., taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 11 for Declaration of Clara W. Wang in Support of Boston Scientific's Responsive regarding Claim Construction Brief; Opposition to Nevro's Motion for Summary Judgement and Opening Motion for Summary Judgement (Document 358-17), Redacted Version of Document Sought to be Filed under Sealed—Videotaped Deposition of Jim Cassidy, taken on Nov. 29, 2017, *Nevro Corp. vs. Boston Scientific Corporation and Boston Scientific Neuromodulation Corporation*, Case No. 3:16-cv-06830-VC-MEJ, filed Apr. 26, 2018, 9 pages.
Exhibit 12 for Declaration of Clara W. Wang in Support of Boston Scientific's Responsive regarding Claim Construction Brief; Opposition to Nevro's Motion for Summary Judgement and Opening Motion for Summary Judgement (Document 467), Filed under Sealed—Videotaped Deposition of Kaoru Lee Adair, taken on Nov. 17, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 13 for Declaration of Clara W. Wang in Support of Boston Scientific's Responsive regarding Claim Construction Brief; Opposition to Nevro's Motion for Summary Judgement and Opening Motion for Summary Judgement (Document 358-19), Redacted Version of Document Sought to be Filed under Seal—Videotaped Deposition of Jim Cassidy, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 14 for Declaration of Clara W. Wang in Support of Boston Scientific's Responsive regarding Claim Construction Brief; Opposition to Nevro's Motion for Summary Judgement and Opening Motion for Summary Judgement (Document 358-20), Apr. 2018 Email between K. Carter and MoFo-NevroBSX, taken on Nov. 30, 2017, *Nevro Corp. vs. Boston Scientific Corporation and Boston Scientific Neuromodulation Corporation*, Case No. 3:16-cv-06830-VC-MEJ, filed Apr. 26, 2018, 2 pages.
Exhibit 15 for Declaration of Clara W. Wang in Support of Boston Scientific's Responsive regarding Claim Construction Brief; Opposition to Nevro's Motion for Summary Judgement and Opening Motion for Summary Judgement (Document 358-21), Boston Scientific Advancing Science for Life—Technical Sales Training, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 16 for Declaration of Clara W. Wang in Support of Boston Scientific's Responsive regarding Claim Construction Brief; Opposition to Nevro's Motion for Summary Judgement and Opening Motion for Summary Judgement (Document 358-22), Product Specification for Ninja System, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 17 for Declaration of Clara W. Wang in Support of Boston Scientific's Responsive regarding Claim Construction Brief; Opposition to Nevro's Motion for Summary Judgement and Opening Motion for Summary Judgement (Document 358-23), Deposition of Ben Pless, taken on Apr. 10, 2018, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 18 for Declaration of Clara W. Wang in Support of Boston Scientific's Responsive regarding Claim Construction Brief; Opposition to Nevro's Motion for Summary Judgement and Opening Motion for Summary Judgement (Document 358-24), Merriam-Webster's Collegiate Dictionary, *Nevro Corp. vs. Boston Scientific*

US 10,493,275 B2

Page 20

(56) References Cited

OTHER PUBLICATIONS

*Corporation and Boston Scientific Neuromodulation Corporation*, Case No. 3:16-cv-06830-VC-MEJ, filed Apr. 26, 2018, 5 pages.
Exhibit 19 for Declaration of Clara W. Wang in Support of Boston Scientific's Responsive regarding Claim Construction Brief; Opposition to Nevro's Motion for Summary Judgement and Opening Motion for Summary Judgement (Document 358-25), Merriam-Webster's Collegiate Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 20 for Declaration of Clara W. Wang in Support of Boston Scientific's Responsive regarding Claim Construction Brief; Opposition to Nevro's Motion for Summary Judgement and Opening Motion for Summary Judgement (Document 358-26), Concise Oxford Dictionary, *Nevro Corp. vs. Boston Scientific Corporation and Boston Scientific Neuromodulation Corporation*, Case No. 3:16-cv-06830-VC-MEJ, filed Apr. 26, 2018, 5 pages.
Exhibit 21 for Declaration of Clara W. Wang in Support of Boston Scientific's Responsive regarding Claim Construction Brief; Opposition to Nevro's Motion for Summary Judgement and Opening Motion for Summary Judgement (Document 358-27), Copy of Final Office Action for U.S. Appl. No. 15/134,285, issued Nov. 28, 2017, *Nevro Corp. vs. Boston Scientific Corporation and Boston Scientific Neuromodulation Corporation*, Case No. 3:16-cv-06830-VC-MEJ, filed Apr. 26, 2018, 22 pages.
Exhibit 22 for Declaration of Clara W. Wang in Support of Boston Scientific's Responsive regarding Claim Construction Brief; Opposition to Nevro's Motion for Summary Judgement and Opening Motion for Summary Judgement (Document 358-28), Copy of U.S. Pat. No. 8,355,797 by Caparso et al., *Nevro Corp. vs. Boston Scientific Corporation and Boston Scientific Neuromodulation Corporation*, Case No. 3:16-cv-06830-VC-MEJ, filed Apr. 26, 2018, 21 pages.
Exhibit 23 for Declaration of Clara W. Wang in Support of Boston Scientific's Responsive regarding Claim Construction Brief; Opposition to Nevro's Motion for Summary Judgement and Opening Motion for Summary Judgement (Document 358-29), Redacted Version of the Document Sought to be Filed under Seal—Deposition of Jon Parker dated Nov. 16, 2017, *Nevro Corp. vs. Boston Scientific Corporation and Boston Scientific Neuromodulation Corporation*, Case No. 3:16-cv-06830-VC-Mej, filed Apr. 26, 2018, 12 pages.
Exhibit 24 for Declaration of Clara W. Wang in Support of Boston Scientific's Responsive regarding Claim Construction Brief; Opposition to Nevro's Motion for Summary Judgement and Opening Motion for Summary Judgement (Document 358-30), Redacted Version of the Document Sought to be Filed under Seal—Corrected Rebuttal Expert Report of Ben Plesss regarding Validity dated Mar. 5, 2018, *Nevro Corp. vs. Boston Scientific Corporation and Boston Scientific Neuromodulation Corporation*, Case No. 3:16-cv-06830-VC-MEJ, filed Apr. 26, 2018, 55 pages.
Exhibit 25 for Declaration of Clara W. Wang in Support of Boston Scientific's Responsive regarding Claim Construction Brief; Opposition to Nevro's Motion for Summary Judgement and Opening Motion for Summary Judgement (Document 358-31), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed Apr. 26, 2018, 14 pages.
Exhibit 26 for Declaration of Clara W. Wang in Support of Boston Scientific's Responsive regarding Claim Construction Brief; Opposition to Nevro's Motion for Summary Judgement and Opening Motion for Summary Judgement (Document 358-32), Redacted Version of Document Sought to be Filed under Seal—Opening Expert Report of Ben Pless regarding Infringement dated Jan. 18, 2018, *Nevro Corp. vs. Boston Scientific Corporation and Boston Scientific Neuromodulation Corporation*, Case No. 3:16-cv-06830-VC-MEJ, filed Apr. 26, 2018, 23 pages.
Exhibit 27 for Declaration of Clara W. Wang in Support of Boston Scientific's Responsive regarding Claim Construction Brief; Opposition to Nevro's Motion for Summary Judgement and Opening Motion for Summary Judgement (Document 358-33), Copy of U.S. Patent Application Publication No. 2017/0050021 to Cosman Sr., *Nevro Corp. vs. Boston Scientific Corporation and Boston Scientific Neuromodulation Corporation*, Case No. 3:16-cv-06830-VC-MEJ, filed Apr. 26, 2018, 32 pages.
Exhibit 28 for Declaration of Clara W. Wang in Support of Boston Scientific's Responsive regarding Claim Construction Brief; Opposition to Nevro's Motion for Summary Judgement and Opening Motion for Summary Judgement (Document 358-34), Expert Report of William S. Rosenberg, MD, FAANS, dated Jan. 18, 2018, *Nevro Corp. vs. Boston Scientific Corporation and Boston Scientific Neuromodulation Corporation*, Case No. 3:16-cv-06830-VC-MEJ, filed Apr. 26, 2018, 4 pages.
Exhibit 29 for Declaration of Clara W. Wang in Support of Boston Scientific's Responsive regarding Claim Construction Brief; Opposition to Nevro's Motion for Summary Judgement and Opening Motion for Summary Judgement (Document 358-35), Declaration of David Caraway, M.D. Ph.D., dated Feb. 16, 2016, *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 30 for Declaration of Clara W. Wang in Support of Boston Scientific's Responsive regarding Claim Construction Brief; Opposition to Nevro's Motion for Summary Judgement and Opening Motion for Summary Judgement (Document 358-36), Filed under Seal—Document NEVRO_BSXCA0073295-300, *Nevro Corp. vs. Boston Scientific Corporation and Boston Scientific Neuromodulation Corporation*, Case No. 3:16-cv-06830-VC-MEJ, filed Apr. 26, 2018, 1 pages.
Exhibit 31 for Declaration of Clara W. Wang in Support of Boston Scientific's Responsive regarding Claim Construction Brief; Opposition to Nevro's Motion for Summary Judgement and Opening Motion for Summary Judgement (Document 358-37), Article by Alexander J.R. Macdonald et al., *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 32 for Declaration of Clara W. Wang in Support of Boston Scientific's Responsive regarding Claim Construction Brief; Opposition to Nevro's Motion for Summary Judgement and Opening Motion for Summary Judgement (Document 358-38), Copy of U.S. Pat. No. 5,776,170 to MacDonald et al., *Nevro Corp. vs. Boston Scientific Corporation and Boston Scientific Neuromodulation Corporation*, Case No. 3:16-cv-06830-VC-MEJ, filed Apr. 26, 2018, 12 pages.
Exhibit 33 for Declaration of Clara W. Wang in Support of Boston Scientific's Responsive regarding Claim Construction Brief; Opposition to Nevro's Motion for Summary Judgement and Opening Motion for Summary Judgement (Document 358-39), Copy of File History for U.S. Appl. No. 14/525,134, issued Mar. 12, 2015, *Nevro Corp. vs. Boston Scientific Corporation and Boston Scientific Neuromodulation Corporation*, Case No. 3:16-cv-06830-VC-MEJ, filed Apr. 26, 2018, 34 pages.
Exhibit 34 for Declaration of Clara W. Wang in Support of Boston Scientific's Responsive regarding Claim Construction Brief; Opposition to Nevro's Motion for Summary Judgement and Opening Motion for Summary Judgement (Document 358-40), Filed under Seal—Document NEVRO_BSXCA0108347-8, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 35 for Declaration of Clara W. Wang in Support of Boston Scientific's Responsive regarding Claim Construction Brief; Opposition to Nevro's Motion for Summary Judgement and Opening Motion for Summary Judgement (Document 358-41), Copy of Non-Final Office Action for U.S. Appl. No. 14/503,259, issued Dec. 3, 2015, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 36 for Declaration of Clara W. Wang in Support of Boston Scientific's Responsive regarding Claim Construction Brief; Opposition to Nevro's Motion for Summary Judgement and Opening Motion for Summary Judgement (Document 358-42), Documents

(56) References Cited

OTHER PUBLICATIONS from File History for U.S. Appl. No. 14/261,369, *Nevro Corp.* vs. *Boston Scientific Corporation and Boston Scientific Neuromodulation Corporation*, Case No. 3:16-cv-06830-VC-MEJ, filed Apr. 26, 2018, 59 pages.

Exhibit 37 for Declaration of Clara W. Wang in Support of Boston Scientific's Responsive regarding Claim Construction Brief; Opposition to Nevro's Motion for Summary Judgement and Opening Motion for Summary Judgement (Document 358-43), Copy of Final Office Action for U.S. Appl. No. 15/134,285, issued Nov. 28, 2017, *Nevro Corp.* vs. *Boston Scientific Corporation and Boston Scientific Neuromodulation Corporation*, Case No. 3:16-cv-06830-VC-MEJ, filed Apr. 26, 2018, 22 pages.

Exhibit 38 for Declaration of Clara W. Wang in Support of Boston Scientific's Responsive regarding Claim Construction Brief; Opposition to Nevro's Motion for Summary Judgement and Opening Motion for Summary Judgement (Document 358-44), U.S. National Library of Medicine—ClinicalTrials.gov, *Nevro Corp.* vs. *Boston Scientific Corporation and Boston Scientific Neuromodulation Corporation*, Case No. 3:16-cv-06830-VC-MEJ, filed Apr. 26, 2018, 6 pages.

Exhibit 39 for Declaration of Clara W. Wang in Support of Boston Scientific's Responsive regarding Claim Construction Brief; Opposition to Nevro's Motion for Summary Judgement and Opening Motion for Summary Judgement (Document 358-45), Redacted Version of Document Sought to be Filed under Seal—Jan. 23, 2014 Correspondence to Boston Scientific Corporation, *Nevro Corp.* vs. *Boston Scientific Corporation and Boston Scientific Neuromodulation Corporation*, Case No. 3:16-cv-06830-VC-MEJ, filed Apr. 26, 2018, 10 pages.

Exhibit 40 for Declaration of Clara W. Wang in Support of Boston Scientific's Responsive regarding Claim Construction Brief; Opposition to Nevro's Motion for Summary Judgement and Opening Motion for Summary Judgement (Document 358-46), Redacted Version of Document Sought to be Filed under Seal—Nov. 23, 2016 Email and Correspondence to Kaoru Adair, *Nevro Corp.* vs. *Boston Scientific Corporation and Boston Scientific Neuromodulation Corporation*, Case No. 3:16-cv-06830-VC-MEJ, filed Apr. 26, 2018, 8 pages.

Exhibit 41 for Declaration of Clara W. Wang in Support of Boston Scientific's Responsive regarding Claim Construction Brief; Opposition to Nevro's Motion for Summary Judgement and Opening Motion for Summary Judgement (Document 358-47), Boston Scientific—Investigational Device Exemption (IDE) Application, submission date Feb. 21, 2013, *Nevro Corp.* vs. *Boston Scientific Corporation and Boston Scientific Neuromodulation Corporation*, Case No. 3:16-cv-06830-VC-MEJ, filed Apr. 26, 2018, 5 pages.

Exhibit 42 for Declaration of Clara W. Wang in Support of Boston Scientific's Responsive regarding Claim Construction Brief; Opposition to Nevro's Motion for Summary Judgement and Opening Motion for Summary Judgement (Document 358-48), Redacted Version of Document Sought to be Filed under Seal—Boston Scientific—A Randomized Controlled Study to Evaluate the Safety and Effectiveness of the Precision Spinal Cord Stimulator System Adapted for High-Rate Spinal Cord Stimulation, *Nevro Corp.* vs. *Boston Scientific Corporation and Boston Scientific.*

Exhibit 43 for Declaration of Clara W. Wang in Support of Boston Scientific's Responsive regarding Claim Construction Brief; Opposition to Nevro's Motion for Summary Judgement and Opening Motion for Summary Judgement (Document 358-49), World Medical Association—WMA Declaration of Helsinki—Ethical Principles for Medical Research Involving Human Subjects, *Nevro Corp.* v. *Boston Scientific Corporation and Boston Scientific Neuromodulation Corporation*, Case No. 3:16-cv-06830-VC-MEJ, filed Apr. 29, 2018, 3 pages.

Exhibit 44 for Declaration of Clara W. Wang in Support of Boston Scientific's Responsive regarding Claim Construction Brief; Opposition to Nevro's Motion for Summary Judgement and Opening Motion for Summary Judgement (Document 358-50), Copy of U.S. Patent Application Publication No. 2007/0073354 to Knudson et al., *Nevro Corp.* vs. *Boston Scientific Corporation and Boston Scientific Neuromodulation Corporation*, Case No. 3:16-cv-06830-VC-MEJ, filed Apr. 26, 2018, 15 pages.

Exhibit 45 for Declaration of Clara W. Wang in Support of Boston Scientific's Responsive regarding Claim Construction Brief; Opposition to Nevro's Motion for Summary Judgement and Opening Motion for Summary Judgement (Document 358-51), Copy of U.S. Patent Application Publication No. 2007/0060954 to Cameron et al., *Nevro Corp.* vs. *Boston Scientific Corporation and Boston Scientific Neuromodulation Corporation*, Case No. 3:16-cv-06830-VC-MEJ, filed Apr. 26, 2018, 21 pages.

Exhibit 46 for Declaration of Clara W. Wang in Support of Boston Scientific's Responsive regarding Claim Construction Brief; Opposition to Nevro's Motion for Summary Judgement and Opening Motion for Summary Judgement (Document 358-52), Copy of Documents from File History for U.S. Appl. No. 12/765,747, *Nevro Corp.* vs. *Boston Scientific Corporation and Boston Scientific Neuromodulation Corporation*, Case No. 3:16-cv-06830-VC-MEJ, filed Apr. 26, 2018, 57 pages.

Exhibit 47 for Declaration of Clara W. Wang in Support of Boston Scientific's Responsive regarding Claim Construction Brief; Opposition to Nevro's Motion for Summary Judgement and Opening Motion for Summary Judgement (Document 358-53), Copy of Response to Final Office Action for U.S. Appl. No. 14/292,671, filed Jan. 17, 2017, *Nevro Corp.* vs. *Boston Scientific Corporation and Boston Scientific Neuromodulation Corporation*, Case No. 3:16-cv-06830-VC-MEJ, filed Apr. 26, 2018, 12 pages.

Exhibit 48 for Declaration of Clara W. Wang in Support of Boston Scientific's Responsive regarding Claim Construction Brief; Opposition to Nevro's Motion for Summary Judgement and Opening Motion for Summary Judgement (Document 358-54), Copy of Response to Non-Final Office Action for U.S. Appl. No. 14/503,259, filed Mar. 16, 2015, *Nevro Corp.* vs. *Boston Scientific Corporation and Boston Scientific Neuromodulation Corporation*, Case No. 3:16-cv-06830-VC-MEJ, filed Apr. 26, 2018, 30 pages.

Exhibit 49 for Declaration of Clara W. Wang in Support of Boston Scientific's Responsive regarding Claim Construction Brief; Opposition to Nevro's Motion for Summary Judgement and Opening Motion for Summary Judgement (Document 358-55), Redacted Version of Document Sought to be Filed under Seal—Deposition of Konstantinos Alataris dated Nov. 14, 2017, *Nevro Corp.* vs. *Boston Scientific Corporation and Boston Scientific Neuromodulation Corporation*, Case No. 3:16-cv-06830-VC-MEJ, filed Apr. 26, 2018, 21 pages.

Exhibit 50 for Declaration of Clara W. Wang in Support of Boston Scientific's Responsive regarding Claim Construction Brief; Opposition to Nevro's Motion for Summary Judgement and Opening Motion for Summary Judgement (Document 358-56), Chart for Asserted Claims by Limitation Category, *Nevro Corp.* vs. *Boston Scientific Corporation and Boston Scientific Neuromodulation Corporation*, Case No. 3:16-cv-06830-VC-MEJ, filed Apr. 26, 2018, 12 pages.

Exhibit 51 for Declaration of Clara W. Wang in Support of Boston Scientific's Responsive regarding Claim Construction Brief; Opposition to Nevro's Motion for Summary Judgement and Opening Motion for Summary Judgement (Document 358-57), Copy of U.S. Patent Application Publication No. 2009/0204173 to Fang et al., *Nevro Corp.* vs. *Boston Scientific Corporation and Boston Scientific Neuromodulation Corporation*, Case No. 3:16-cv-06830-VC-MEJ, filed Apr. 26, 2018, 33 pages.

Exhibit 52 for Declaration of Clara W. Wang in Support of Boston Scientific's Responsive regarding Claim Construction Brief; Opposition to Nevro's Motion for Summary Judgement and Opening Motion for Summary Judgement (Document 358-58), Copy of Applicant-Initiated Interview Summary for U.S. Appl. No. 14/037,262, dated Feb. 25, 2014, Nevro Corp. vs. Boston Scientific Corporation and Boston Scientific Neuromodulation Corporation, Case No. 3:16-cv-06830-VC-MEJ, filed Apr. 26, 2018, 5 pages.

Exhibit 53 for Declaration of Clara W. Wang in Support of Boston Scientific's Responsive regarding Claim Construction Brief; Opposition to Nevro's Motion for Summary Judgement and Opening Motion for Summary Judgement (Document 358-59), Redacted Version of Document Sought to be Filed under Seal—Videotaped

(56) References Cited

OTHER PUBLICATIONS

Deposition of Zi-Ping Fang dated Nov. 2, 2017, *Nevro Corp. vs. Boston Scientific Corporation and Boston Scientific Neuromodulation Corporation*, Case No. 3:16-cv-06830-VC-MEJ, filed Apr. 26, 2018, 16 pages.
Exhibit 54 for Declaration of Clara W. Wang in Support of Boston Scientific's Responsive regarding Claim Construction Brief; Opposition to Nevro's Motion for Summary Judgement and Opening Motion for Summary Judgement (Document 358-60), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 55 for Declaration of Clara W. Wang in Support of Boston Scientific's Responsive regarding Claim Construction Brief; Opposition to Nevro's Motion for Summary Judgement and Opening Motion for Summary Judgement (Document 358-61), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 56 for Declaration of Clara W. Wang in Support of Boston Scientific's Responsive regarding Claim Construction Brief; Opposition to Nevro's Motion for Summary Judgement and Opening Motion for Summary Judgement (Document 358-62), Declaration of Rafael Cabunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed Apr. 26, 2018, 132 pages.
Exhibit 57 for Declaration of Clara W. Wang in Support of Boston Scientific's Responsive regarding Claim Construction Brief; Opposition to Nevro's Motion for Summary Judgement and Opening Motion for Summary Judgement (Document 358-63), Deposition of David Caraway, M.D., Ph.D., dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 58 for Declaration of Clara W. Wang in Support of Boston Scientific's Responsive regarding Claim Construction Brief; Opposition to Nevro's Motion for Summary Judgement and Opening Motion for Summary Judgement (Document 358-64), Filed under Seal—Document NEVRO_BSXCA0209790-812, *Nevro Corp. vs. Boston Scientific Corporation and Boston Scientific Neuromodulation Corporation*, Case No. 3:16-cv-06830-VC-MEJ, filed Apr. 26, 2018, 1 pages.
Exhibit 59 for Declaration of Clara W. Wang in Support of Boston Scientific's Responsive regarding Claim Construction Brief; Opposition to Nevro's Motion for Summary Judgement and Opening Motion for Summary Judgement (Document 358-65), Videotaped Deposition of Dr. James North taken on Nov. 18, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 60 for Declaration of Clara W. Wang in Support of Boston Scientific's Responsive regarding Claim Construction Brief; Opposition to Nevro's Motion for Summary Judgement and Opening Motion for Summary Judgement (Document 358-66), Videotaped Deposition of Robert Nathan taken on Nov. 15, 2017, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 61 for Declaration of Clara W. Wang in Support of Boston Scientific's Responsive regarding Claim Construction Brief; Opposition to Nevro's Motion for Summary Judgement and Opening Motion for Summary Judgement (Document 358-67), Case Report by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 3 pages.
Exhibit 62 for Declaration of Clara W. Wang in Support of Boston Scientific's Responsive regarding Claim Construction Brief; Opposition to Nevro's Motion for Summary Judgement and Opening Motion for Summary Judgement (Document 358-68), Videotaped Deposition of Dr. William S. Rosenberg dated Mar. 21, 2018, *Nevro Corp. vs. Boston Scientific Corporation and Boston Scientific Neuromodulation Corporation*, Case No. 3:16-cv-06830-VC-MEJ, filed Apr. 26, 2018, 11 pages.
Exhibit 63 for Declaration of Clara W. Wang in Support of Boston Scientific's Responsive regarding Claim Construction Brief; Opposition to Nevro's Motion for Summary Judgement and Opening Motion for Summary Judgement (Document 358-69), Document by Yearwood et al., *Nevro Corp. vs. Boston Scientific Corporation and Boston Scientific Neuromodulation Corporation*, Case No. 3:16-cv-06830-VC-MEJ, filed Apr. 26, 2018, 8 pages.
Exhibit 64 for Declaration of Clara W. Wang in Support of Boston Scientific's Responsive regarding Claim Construction Brief; Opposition to Nevro's Motion for Summary Judgement and Opening Motion for Summary Judgement (Document 358-70), Redacted Version of Document Sought to be Filed under Seal—Videotaped Deposition of James Thacker (vol. I) dated Dec. 7, 2017, *Nevro Corp. vs. Boston Scientific Corporation and Boston Scientific Neuromodulation Corporation*, Case No. 3:16-cv-06830-VC-MEJ, filed Apr. 26, 2018, 35 pages.
Exhibit 65 for Declaration of Clara W. Wang in Support of Boston Scientific's Responsive regarding Claim Construction Brief; Opposition to Nevro's Motion for Summary Judgement and Opening Motion for Summary Judgement (Document 358-71), Filed under Seal—Document NEVRO_BSXCA0118164-203, *Nevro Corp. vs. Boston Scientific Corporation and Boston Scientific Neuromodulation Corporation*, Case No. 3:16-cv-06830-VC-MEJ, filed Apr. 26, 2018, 1 page.
Exhibit 66 for Declaration of Clara W. Wang in Support of Boston Scientific's Responsive regarding Claim Construction Brief; Opposition to Nevro's Motion for Summary Judgement and Opening Motion for Summary Judgement (Document 358-72), Videotaped Deposition of Kerry Bradley dated Nov. 8, 2017, *Nevro Corp. vs. Boston Scientific Corporation and Boston Scientific Neuromodulation Corporation*, Case No. 3:16-cv-06830-VC-MEJ, filed Apr. 26, 2018, 10 pages.
Exhibit 67 for Declaration of Clara W. Wang in Support of Boston Scientific's Responsive regarding Claim Construction Brief; Opposition to Nevro's Motion for Summary Judgement and Opening Motion for Summary Judgement (Document 358-73), Response to Final Office Action for U.S. Appl. No. 12/765,685 filed Sep. 19, 2013, *Nevro Corp. vs. Boston Scientific Corporation and Boston Scientific Neuromodulation Corporation*, Case No. 3:16-cv-06830-VC-MEJ, filed Apr. 26, 2018, 15 pages.
Exhibit 68 for Declaration of Clara W. Wang in Support of Boston Scientific's Responsive regarding Claim Construction Brief; Opposition to Nevro's Motion for Summary Judgement and Opening Motion for Summary Judgement (Document 358-74), Response to Non-Final Office Action for U.S. Appl. No. 13/830,992 filed Feb. 24, 2014, *Nevro Corp. vs. Boston Scientific Corporation and Boston Scientific Neuromodulation Corporation*, Case No. 3:16-cv-06830-VC-MEJ, filed Apr. 26, 2018, 15 pages.
Rebuttal Expert Report and Declaration of Daniel Lanovaz (Document 359), *Nevro Corp. vs. Boston Scientific Corporation and Boston Scientific Neuromodulation Corporation*, Case No. 3:16-cv-06830-VC-MEJ, filed Apr. 26, 2018, 10 pages.
Nevro's Reply in Support of its Motion for Summary Adjudication and Opposition to BSC's Motion for Summary Judgement (Document 468), Updated Redacted Version of ECF No. 382-2, *Nevro Corp. vs. Boston Scientific Corporation and Boston Scientific Neuromodulation Corporation*, Case No. 3:16-cv-06830-VC-MEJ, filed Jul. 30, 2018, 40 pages.
Declaration of Joshua Goshorn in Support of Nevro's Reply in Support of Motion for Summary Adjudication and Opposition to BSC's Motion for Summary Judgement (Document 375), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Joshua Goshorn in Support of Nevro's Reply in Support of Motion for Summary Adjudication and Opposition to Bsc's Motion for Summary Judgement (Document 375-1), Entire Document Sought—Joshua Goshorn opening Expert Report,

(56) References Cited

OTHER PUBLICATIONS

*Nevro Corp. vs. Boston Scientific Corporation and Boston Scientific Neuromodulation Corporation*, Case No. 3:16-cv-06830-VC-MEJ, filed May 10, 2018, 1 page.
Declaration of Ben Pless in Support of Nevro's Reply in Support of Motion for Summary Adjudication and Opposition to BSC's Motion for Summary Judgement (Document 376), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of Ben Pless in Support of Nevro's Reply in Support of Motion for Summary Adjudication and Opposition to BSC's Motion for Summary Judgement (Document 376-1), Redacted Version of Document Sought to be Sealed —Opening Expert Report of Ben Pless, *Nevro Corp. vs. Boston Scientific Corporation and Boston Scientific Neuromodulation Corporation*, Case No. 3:16-cv-06830-VC-MEJ, filed May 10, 2018, 151 pages.
Exhibit B for Declaration of Ben Pless in Support of Nevro's Reply in Support of Motion for Summary Adjudication and Opposition to BSC's Motion for Summary Judgement (Document 376-2), Redacted Version of Document Sought to be Sealed—Corrected Rebuttal Expert Report of Ben Pless regarding Validity, dated Mar. 5, 2018, *Nevro Corp. vs. Boston Scientific Corporation and Boston Scientific Neuromodulation Corporation*, Case No. 3:16-cv-06830-VC-MEJ, filed May 10, 2018, 116 pages.
Declaration of William Sanford Rosenberg in Support of Nevro's Reply in Support of Motion for Summary Adjudication and Opposition to BSC's Motion for Summary Judgement (Document 377), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A for Declaration of William Sanford Rosenberg in Support of Nevro's Reply in Support of Motion for Summary Adjudication and Opposition to BSC's Motion for Summary Judgement (Document 377-1), Curriculum Vitae of William Sanford Rosenberg, M.D., *Nevro Corp. vs. Boston Scientific Corporation and Boston Scientific Neuromodulation Corporation*, Case No. 3:16-cv-06830-VC-MEJ, filed May 10, 2018, 21 pages.
Exhibit B for Declaration of William Sanford Rosenberg in Support of Nevro's Reply in Support of Motion for Summary Adjudication and Opposition to BSC's Motion for Summary Judgement (Document 377-2), Redacted Version of Document Sought to be Sealed—Deposition of William Sanford Rosenberg, M.D. FAAMS, *Nevro Corp. vs. Boston Scientific Corporation and Boston Scientific Neuromodulation Corporation*, Case No. 3:16-cv-06830-VC-MEJ, filed May 10, 2018, 40 pages.
Declaration of Robert Schiff in Support of Nevro's Reply in Support of Motion for Summary Adjudication and Opposition to BSC's Motion for Summary Judgement (Document 378), *Nevro Corp. vs. Boston Scientific Corporation and Boston Scientific Neuromodulation Corporation*, Case No. 3:16-cv-06830-VC-MEJ, filed May 10, 2018, 2 pages.
Exhibit A—Updated—for Declaration of Robert Schiff in Support of Nevro's Reply in Support of Motion for Summary Adjudication and Opposition to BSC's Motion for Summary Judgement (Document 410), Redacted Version of ECF No. 382-10—Exhibit A to the May 9, 2018 Declaration of Robert Schiff, *Nevro Corp. vs. Boston Sci7ntific Corporation and Boston Scientific Neuromodulation Corporation*, Case No. 3:16-cv-06830-VC-MEJ, filed May 10, 2018, 72 pages.
Declaration of Nicholas Fung in Support of Nevro's Reply in Support of Motion for Summary Adjudication and Opposition to BSC's Motion for Summary Judgement (Document 379), *Nevro Corp. vs. Boston Scientific Corporation and Boston Scientific Neuromodulation Corporation*, Case No. 3:16-cv-06830-VC-MEJ, filed May 10, 2018, 5 pages.
Exhibit 1 for Declaration of Nicholas Fung in Support of Nevro's Reply in Support of Motion for Summary Adjudication and Opposition to BSC's Motion for Summary Judgement (Document 379-1), Claims Chart, *Nevro Corp. vs. Boston Scientific Corporation and Boston Scientific Neuromodulation Corporation*, Case No. 3:16-cv-06830-VC-MEJ, filed May 10, 2018, 3 pages.
Exhibit 2 for Declaration of Nicholas Fung in Support of Nevro's Reply in Support of Motion for Summary Adjudication and Opposition to BSC's Motion for Summary Judgement (Document 379-2), Entire Document Sought to be Sealed—Document BSC-NVRO_ 00713169-172, *Nevro Corp. vs. Boston Scientific Corporation and Boston Scientific Neuromodulation Corporation*, Case No. 3:16-cv-06830-VC-MEJ, filed May 10, 2018, 1 page.
Exhibit 3 for Declaration of Nicholas Fung in Support of Nevro's Reply in Support of Motion for Summary Adjudication and Opposition to BSC's Motion for Summary Judgement (Document 379-3), Redacted Version of Document Sought to be Sealed—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 10, 2018, 13 pages.
Exhibit 4 for Declaration of Nicholas Fung in Support of Nevro's Reply in Support of Motion for Summary Adjudication and Opposition to BSC's Motion for Summary Judgement (Document 379-4), Redacted Version of Document Sought to be Sealed—Videotaped Deposition of Sridhar Kothandaraman, *Nevro Corp. vs. Boston Scientific Corporation and Boston Scientific Neuromodulation Corporation*, Case No. 3:16-cv-06830-VC-MEJ, filed May 10, 2018, 14 pages.
Exhibit 5 for Declaration of Nicholas Fung in Support of Nevro's Reply in Support of Motion for Summary Adjudication and Opposition to BSC's Motion for Summary Judgement (Document 379-5), Videotaped Deposition of Brian Erickson dated Dec. 15, 2017, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 6 for Declaration of Nicholas Fung in Support of Nevro's Reply in Support of Motion for Summary Adjudication and Opposition to BSC's Motion for Summary Judgement (Document 379-6), Plaintiffs Brief regarding Claim Construction of the "Adapted to" Claim Term, *Nevro Corp. vs. Boston Scientific Corporation and Boston Scientific Neuromodulation Corporation*, Case No. 3:16-cv-06830-VC-MEJ, filed May 10, 2018, 7 pages.
Exhibit 7 for Declaration of Nicholas Fung in Support of Nevro's Reply in Support of Motion for Summary Adjudication and Opposition to BSC's Motion for Summary Judgement (Document 379-7), Plaintiffs Response Brief regarding Claim Construction of the "Adapted to" Claim Term, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 8 for Declaration of Nicholas Fung in Support of Nevro's Reply in Support of Motion for Summary Adjudication and Opposition to BSC's Motion for Summary Judgement (Document 379-8), Deposition of Ben Pless dated Apr. 10, 2018, *Nevro Corp. vs. Boston Scientific Corporation and Boston Scientific Neuromodulation Corporation*, Case No. 3:16-cv-06830-VC-MEJ, filed May 10, 2018, 31 pages.
Exhibit 9 for Declaration of Nicholas Fung in Support of Nevro's Reply in Support of Motion for Summary Adjudication and Opposition to BSC's Motion for Summary Judgement (Document 379-9), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed May 10, 2018, 62 pages.
Exhibit 10 for Declaration of Nicholas Fung in Support of Nevro's Reply in Support of Motion for Summary Adjudication and Opposition to BSC's Motion for Summary Judgement (Document 379-10) Expert Report and Declaration of Gene Fridman, Ph.D., regarding Claim Construction, *Nevro Corp. vs. Boston Scientific Corporation and Boston Scientific Neuromodulation Corporation*, Case No. 3:16-cv-06830-VC-MEJ, filed May 10, 2018, 6 pages.
Exhibit 11 for Declaration of Nicholas Fung in Support of Nevro's Reply in Support of Motion for Summary Adjudication and Opposition to BSC's Motion for Summary Judgement (Document 379-11), Article by Tan et al., *Nevro Corp. vs. Boston Scientific Corporation and Boston Scientific Neuromodulation Corporation*, Case No. 3:16-cv-06830-VC-MEJ, filed May 10, 2018, 8 pages.

(56) References Cited

OTHER PUBLICATIONS

Exhibit 12 for Declaration of Nicholas Fung in Support of Nevro's Reply in Support of Motion for Summary Adjudication and Opposition to BSC's Motion for Summary Judgement (Document 379-12), Decision Denying Institution of Inter Partes Review for U.S. Pat. No. 8,359,102 (Case IPR2015-01203), *Nevro Corp. vs. Boston Scientific Corporation and Boston Scientific Neuromodulation Corporation*, Case No. 3:16-cv-06830-VC-MEJ, filed May 10, 2018, 21 pages.

Exhibit 13 for Declaration of Nicholas Fung in Support of Nevro's Reply in Support of Motion for Summary Adjudication and Opposition to BSC's Motion for Summary Judgement (Document 379-13), Certified Copy of U.S. Pat. No. 9,327,125, *Nevro Corp. vs. Boston Scientific Corporation and Boston Scientific Neuromodulation Corporation*, Case No. 3:16-cv-06830-VC-MEJ, filed May 10, 2018, 66 pages.

Exhibit 14 for Declaration of Nicholas Fung in Support of Nevro's Reply in Support of Motion for Summary Adjudication and Opposition to BSC's Motion for Summary Judgement (Document 379-14), Copy of U.S. Pat. No. 9,492,664, *Nevro Corp. vs. Boston Scientific Corporation and Boston Scientific Neuromodulation Corporation*, Case No. 3:16-cv-06830-VC-MEJ, filed May 10, 2018, 25 pages.

Exhibit 15 for Declaration of Nicholas Fung in Support of Nevro's Reply in Support of Motion for Summary Adjudication and Opposition to Bsc's Motion for Summary Judgement (Document 379-15), Copy of U.S. Pat. No. 9,339,655, *Nevro Corp. vs. Boston Scientific Corporation and Boston Scientific Neuromodulation Corporation*, Case No. 3:16-cv-06830-VC-MEJ, filed May 10, 2018, 23 pages.

Exhibit 16 for Declaration of Nicholas Fung in Support of Nevro's Reply in Support of Motion for Summary Adjudication and Opposition to Bsc's Motion for Summary Judgement (Document 379-16), Redacted Version of Document Sought to be Sealed—Videotaped Deposition of Richard T. Mihran, Ph.D., dated Mar. 12, 2018, *Nevro Corp. vs. Boston Scientific Corporation and Boston Scientific Neuromodulation Corporation*, Case No. 3:16-cv-06830-VC-MEJ, filed May 10, 2018, 29 pages.

Exhibit 17 for Declaration of Nicholas Fung in Support of Nevro's Reply in Support of Motion for Summary Adjudication and Opposition to BSC's Motion for Summary Judgement (Document 379-17), Redacted Version of Document Sought to be Sealed—Videotaped Deposition of Jim Cassidy, dated May 17, 2017, *Nevro Corp. vs. Boston Scientific Corporation and Boston Scientific Neuromodulation Corporation*, Case No. 3:16-cv-06830-VC-MEJ, filed May 10, 2018, 13 pages.

Exhibit 18 for Declaration of Nicholas Fung in Support of Nevro's Reply in Support of Motion for Summary Adjudication and Opposition to BSC's Motion for Summary Judgement (Document 379-18), Redacted Version of Document Sought to be Sealed—Deposition of Adam Lipson, M.D., dated Apr. 12, 2018, *Nevro Corp. vs. Boston Scientific Corporation and Boston Scientific Neuromodulation Corporation*, Case No. 3:16-cv-06830-VC-MEJ, filed May 10, 2018, 10 pages.

Exhibit 19 for Declaration of Nicholas Fung in Support of Nevro's Reply in Support of Motion for Summary Adjudication and Opposition to BSC's Motion for Summary Judgement (Document 379-19), Redacted Version of Document Sought to be Sealed—BSC's Nov. 10, 2017 Supplemental Responses and Objections to Nevro's Interrogatory Requests Nos. 2, 4, 5, and 7, *Nevro Corp. vs. Boston Scientific Corporation and Boston Scientific Neuromodulation Corporation*, Case No. 3:16-cv-06830-VC-MEJ, filed May 10, 2018, 9 pages.

Exhibit 20 for Declaration of Nicholas Fung in Support of Nevro's Reply in Support of Motion for Summary Adjudication and Opposition to BSC's Motion for Summary Judgement (Document 379-20), Entire Document Sought to be Sealed—Deposition of Kaoru Adair, *Nevro Corp. vs. Boston Scientific Corporation and Boston Scientific Neuromodulation Corporation*, Case No. 3:16-cv-06830-VC-MEJ, filed May 10, 2018, 1 page.

Exhibit 21—Updated—for Declaration of Nicholas Fung in Support of Nevro's Reply in Support of Motion for Summary Adjudication and Opposition to BSC's Motion for Summary Judgement (Document 471), Redacted Version of ECF No. 382-24—Videotaped Deposition of Kaoru Adair dated May 10, 2017, *Nevro Corp. vs. Boston Scientific Corporation and Boston Scientific Neuromodulation Corporation*, Case No. 3:16-cv-06830-VC-MEJ, filed May 10, 2018, 18 pages.

Exhibit 22 Declaration of Nicholas Fung in Support of Nevro's Reply in Support of Motion for Summary Adjudication and Opposition to BSC's Motion for Summary Judgement (Document 379-22), Redacted Version of Document Sought to be Sealed—Nevro Corp.'s First Amended Disclosure of Asserted Claims and Infringement Contentions, *Nevro Corp. vs. Boston Scientific Corporation and Boston Scientific Neuromodulation Corporation*, Case No. 3:16-cv-06830-VC-MEJ, filed May 10, 2018, 6 pages.

Exhibit 23 for Declaration of Nicholas Fung in Support of Nevro's Reply in Support of Motion for Summary Adjudication and Opposition to BSC's Motion for Summary Judgement (Document 379-23), Entire Document Sought to be Sealed—Document BSC-NVRO_00720938-940, *Nevro Corp. vs. Boston Scientific Corporation and Boston Scientific Neuromodulation Corporation*, Case No. 3:16-cv-06830-VC-MEJ, filed May 10, 2018, 1 page.

Exhibit 24 for Declaration of Nicholas Fung in Support of Nevro's Reply in Support of Motion for Summary Adjudication and Opposition to BSC's Motion for Summary Judgement (Document 379-24), Redacted Version of Document Sought to be Sealed—Deposition of Joshua Goshorn, dated Mar. 23, 2018, *Nevro Corp. vs. Boston Scientific Corporation and Boston Scientific Neuromodulation Corporation*, Case No. 3:16-cv-06830-VC-MEJ, filed May 10, 2018, 15 pages.

Exhibit 25 for Declaration of Nicholas Fung in Support of Nevro's Reply in Support of Motion for Summary Adjudication and Opposition to BSC's Motion for Summary Judgement (Document 379-25), Redacted Version of Document Sought to be Sealed—Videotaped Deposition of Daniel Lanovaz, dated Mar. 21, 2018, *Nevro Corp. vs. Boston Scientific Corporation and Boston Scientific Neuromodulation Corporation*, Case No. 3:16-cv-06830-VC-MEJ, filed May 10, 2018, 11 pages.

Exhibit 26 for Declaration of Nicholas Fung in Support of Nevro's Reply in Support of Motion for Summary Adjudication and Opposition to BSC's Motion for Summary Judgement (Document 379-26), Redacted Version of Document Sought to be Sealed—Rebuttal Expert Report of Richard T. Mihran, Ph.D. dated Feb. 14, 2018, *Nevro Corp. vs. Boston Scientific Corporation and Boston Scientific Neuromodulation Corporation*, Case No. 3:16-cv-06830-VC-MEJ, filed May 10, 2018, 23 pages.

Exhibit 27 for Declaration of Nicholas Fung in Support of Nevro's Reply in Support of Motion for Summary Adjudication and Opposition to BSC's Motion for Summary Judgement (Document 379-27), Expert Report of Richard T. Mihran, Ph.D., regarding Invalidity of U.S. Pat. Nos. 8,712,533; 9,327,125; 8,359,102; 9,480,842; 9,333,357; 8,792,988, and 8,768,472, *Nevro Corp. vs. Boston Scientific Corporation and Boston Scientific Neuromodulation Corporation*, Case No. 3:16-cv-06830-VC-MEJ, filed May 10, 2018, 6 pages.

Exhibit 28 for Declaration of Nicholas Fung in Support of Nevro's Reply in Support of Motion for Summary Adjudication and Opposition to BSC's Motion for Summary Judgement (Document 379-28), Declaration of Rafael Carbunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed May 10, 2018, 13 pages.

Exhibit 29 for Declaration of Nicholas Fung in Support of Nevro's Reply in Support of Motion for Summary Adjudication and Opposition to BSC's Motion for Summary Judgement (Document 379-29), Redacted Version of Document Sought to be Sealed—Videotaped Deposition of Nevro Corp., with designated corporate representative Rafael Carbunaru, dated May 18, 2017, *Nevro Corp. vs. Boston Scientific Corporation and Boston Scientific Neuromodulation Corporation*, Case No. 3:16-cv-06830-VC-MEJ, filed May 10, 2018, 8 pages.

(56) References Cited

OTHER PUBLICATIONS

Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382), *Nevro Corp. vs. Boston Scientific Corporation and Boston Scientific Neuromodulation Corporation*, Case No. 3:16-cv-06830-VC-MEJ, filed May 14, 2018, 13 pages.
Exhibit A—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 468), Redacted Version of ECF No. 382-2—Nevro's Reply in Support of its Motion for Summary Adjudication and Opposition to BSC's Motion for Summary Judgment, *Nevro Corp. vs. Boston Scientific Corporation and Boston Scientific Neuromodulation Corporation*, Case No. 3:16-cv-06830-VC-MEJ, filed May 14, 2018, 40 pages.
Exhibit B for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-3), Redacted Version of Document Sought to be Filed under Seal—Expert Report of Joshua Goshorn, *Nevro Corp. vs. Boston Scientific Corporation and Boston Scientific Neuromodulation Corporation*, Case No. 3:16-cv-06830-VC-MEJ, filed May 14, 2018, 15 pages.
Exhibit C for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-5), Redacted Version of Document Sought to be Filed under Seal—Expert Report of William S. Rosenberg, M.D., Faans, *Nevro Corp. vs. Boston Scientific Corporation and Boston Scientific Neuromodulation Corporation*, Case No. 3:16-cv-06830-VC-MEJ, filed May 14, 2018, 41 pages.
Exhibit D—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 469), Redacted Version of ECF No. 382-8—Opening Expert Report of Ben Pless regarding Infringement, dated Jan. 18, 2018, *Nevro Corp. vs. Boston Scientific Corporation and Boston Scientific Neuromodulation Corporation*, Case No. 3:16-cv-06830-VC-MEJ, filed May 14, 2018, 152 pages.
Exhibit E—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 470), Redacted Version of ECF No. 382-10—Expert Report of Robert Schiff, Ph.D., RAC, CQA, FRAPS, *Nevro Corp. vs. Boston Scientific Corporation and Boston Scientific Neuromodulation Corporation*, Case No. 3:16-cv-06830-VC-MEJ, filed May 14, 2018, 72 pages.
Exhibit F for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-11), Redacted Version of Document Sought to be Filed under Seal—Cross-Border HCP Arrangement Request, *Nevro Corp. vs. Boston Scientific Corporation and Boston Scientific Neuromodulation Corporation*, Case No. 3:16-cv-06830-VC-MEJ, filed May 14, 2018, 6 pages.
Exhibit G for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-13), Redacted Version of Document Sought to be Filed under Seal—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 14, 2018, 14 pages.
Exhibit H for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-15), Redacted Version of Document Sought to be Filed under Seal—Videotaped Deposition of Sridhar Kothandaraman, dated Nov. 17, 2017, *Nevro Corp. vs. Boston Scientific Corporation and Boston Scientific Neuromodulation Corporation*, Case No. 3:16-cv-06830-VC-MEJ, filed May 14, 2018, 15 pages.
Exhibit I for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-17), Redacted Version of Document Sought to be Filed under Seal—Videotaped Deposition of Richard T. Mihran, dated Mar. 12, 2018, *Nevro Corp. vs. Boston Scientific Corporation and Boston Scientific Neuromodulation Corporation*, Case No. 3:16-cv-06830-VC-MEJ, filed May 14, 2018, 30 pages.
Exhibit J for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-19), Redacted Version of Document Sought to be Filed under Seal—BSC's Nov. 10, 2017 Supplemental Responses and Objections to Nevro's Interrogatory Requests Nos. 2, 4, 5, and 7, *Nevro Corp. vs. Boston Scientific Corporation and Boston Scientific Neuromodulation Corporation*, Case No. 3:16-cv-06830-VC-MEJ, filed May 14, 2018, 10 pages.
Exhibit K for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-21), Redacted Version of Document Sought to be Filed under Seal—Dec. 14, 2016 Correspondence between Boston Scientific and U.S. Food and Drug Administration, *Nevro Corp. vs. Boston Scientific Corporation and Boston Scientific Neuromodulation Corporation*, Case No. 3:16-cv-06830-VC-MEJ, filed May 14, 2018, 23 pages.
Exhibit L—Updated for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 471), Updated Redacted Version of ECF No. 382-24—Videotaped Deposition of Kaoru Lee Adair, dated May 10, 2017, *Nevro Corp. vs. Boston Scientific Corporation and Boston Scientific Neuromodulation Corporation*, Case No. 3:16-cv-06830-VC-MEJ, filed May 14, 2018, 18 pages.
Exhibit M for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-25), Redacted Version of Document Sought to be Filed under Seal—Nevro Corp.'s First Amended Disclosure of Asserted Claims and Infringement Contentions, *Nevro Corp. vs. Boston Scientific Corporation and Boston Scientific Neuromodulation Corporation*, Case No. 3:16-cv-06830-VC-MEJ, filed May 14, 2018, 7 pages.
Exhibit N For Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-27), Redacted Version of Document Sought to be Filed under Seal—Feb. 2016 Email regarding Precision 10K Training Follow-up, *Nevro Corp. vs. Boston Scientific Corporation and Boston Scientific Neuromodulation Corporation*, Case No. 3:16-cv-06830-VC-MEJ, filed May 14, 2018, 5 pages.
Exhibit O for Declaration of Carson D. Anderson in Support of Nevro's Administrative Motion to File under Seal Portions of Nevro's Reply in Support of It's Motion for Summary Judgement (Docu-

(56) References Cited

OTHER PUBLICATIONS ment 382-29), Redacted Version of Document Sought to be Filed under Seal—Deposition of Joshua Goshorn dated Mar. 23, 2018, *Nevro Corp.* vs. *Boston Scientific Corporation and Boston Scientific Neuromodulation Corporation*, Case No. 3:16-cv-06830-VC-MEJ, filed May 14, 2018, 16 pages.
Exhibit P For Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-31), Redacted Version of Document Sought to be Filed under Seal—Videotaped Deposition of Daniel Lanovaz dated Mar. 21, 2018, *Nevro Corp.* vs. *Boston Scientific Corporation and Boston Scientific Neuromodulation Corporation*, Case No. 3:16-cv-06830-VC-MEJ, filed May 14, 2018, 12 pages.
[Proposed] Order Granting Administrative Motion to File under Seal Portions of Nevro's Reply in Support of It's Motion for Summary Adjudication and Opposition to BSC's Motion for Summary Judgement and Supporing Documents (Document 382-33), *Nevro Corp.* vs. *Boston Scientific Corporation and Boston Scientific Neuromodulation Corporation*, Case No. 3:16-cv-06830-VC-MEJ, filed May 14, 2018, 7 pages.
Updated Boston Scientific's Reply in Support of Motion for Summary Judgement (Document 473), Updated Redacted Version of ECF No. 397-3, *Nevro Corp.* vs. *Boston Scientific Corporation and Boston Scientific Neuromodulation Corporation*, Case No. 3:16-cv-06830-VC-MEJ, filed Jul. 30, 2018, 27 pages.
Declaration of Carson D. Anderson in Support of Boston Scientific's Reply in Support of Motion for Summary Judgement (Document 398-1), Redacted Version of Document Sought to be Filed under Seal—Cross-Border HCP Arrangement Request, *Nevro Corp.* vs. *Boston Scientific Corporation and Boston Scientific Neuromodulation Corporation*, Case No. 3:16-cv-06830-VC-MEJ, filed May 24, 2018, 3 pages.
Exhibit 1 for Declaration of Carson D. Anderson in Support of Boston Scientific's Reply in Support of Motion for Summary Judgement (Document 398-2), Redacted Version of Document Sought to be Filed under Seal—May 2004 Email regarding Post-Market Studies for AB SCS System, *Nevro Corp.* vs. *Boston Scientific Corporation and Boston Scientific Neuromodulation Corporation*, Case No. 3:16-cv-06830-VC-MEJ, filed May 24, 2018, 5 pages.
Exhibit 2 for Declaration of Carson D. Anderson in Support of Boston Scientific's Reply in Support of Motion for Summary Judgement (Document 398-3), Redacted Version of Document Sought to be Filed under Seal—Corrected Rebuttal Expert Report of Ben Pless regarding Validity, dated Mar. 5, 2018, *Nevro Corp.* vs. *Boston Scientific Corporation and Boston Scientific Neuromodulation Corporation*, Case No. 3:16-cv-06830-VC-MEJ, filed May 24, 2018, 4 pages.
Exhibit 3 for Declaration of Carson D. Anderson in Support of Boston Scientific's Reply in Support of Motion for Summary Judgement (Document 398-4), Copy of U.S. Pat. No. 7,389,145 by Kilgore et al., *Nevro Corp.* vs. *Boston Scientific Corporation and Boston Scientific Neuromodulation Corporation*, Case No. 3:16-cv-06830-VC-MEJ, filed May 24, 2018, 12 pages.
Exhibit 4 for Declaration of Carson D. Anderson in Support of Boston Scientific's Reply in Support of Motion for Summary Judgement (Document 398-5), Redacted Version of Document Sought to be Filed under Seal—Videotaped Deposition of Robert Schiff, dated Mar. 15, 2018, *Nevro Corp.* vs. *Boston Scientific Corporation and Boston Scientific Neuromodulation Corporation*, Case No. 3:16-cv-06830-VC-MEJ, filed May 24, 2018, 19 pages.
Exhibit 5 for Declaration of Carson D. Anderson in Support of Boston Scientific's Reply in Support of Motion for Summary Judgement (Document 398-6), Filed under Seal—Document NEVRO_BSXCA0093092-109, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 6 for Declaration of Carson D. Anderson in Support of Boston Scientific's Reply in Support of Motion for Summary Judgement (Document 398-7), Filed under Seal—Document NEVRO_BSXCA0067869-75, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 7 for Declaration of Carson D. Anderson in Support of Boston Scientific's Reply in Support of Motion for Summary Judgement (Document 398-8), Filed under Seal—Document NEVRO_BSXCA0147580-86, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 8 for Declaration of Carson D. Anderson in Support of Boston Scientific's Reply in Support of Motion for Summary Judgement (Document 398-9), Filed under Seal—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 7 pages.
Exhibit 9 for Declaration of Carson D. Anderson in Support of Boston Scientific's Reply in Support of Motion for Summary Judgement (Document 398-10), Filed under Seal—Expert Report of W. Todd Schoettelkotte Relating to Damages, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 1 page.
Exhibit 10 for Declaration of Carson D. Anderson in Support of Boston Scientific's Reply in Support of Motion for Summary Judgement (Document 398-11), Redacted Version of Document Sought to be Filed under Seal—Design Change Analysis Form (DCAF), *Nevro Corp.* vs. *Boston Scientific Corporation and Boston Scientific Neuromodulation Corporation*, Case No. 3:16-cv-06830-VC-MEJ, filed May 24, 2018, 2 pages.
Exhibit 11 for Declaration of Carson D. Anderson in Support of Boston Scientific's Reply in Support of Motion for Summary Judgement (Document 398-12), Redacted Version of Document Sought to be Filed under Seal—Videotaped Deposition of Rafael Carbunaru, Ph.D., dated Nov. 14, 2017, *Nevro Corp.* vs. *Boston Scientific Corporation and Boston Scientific Neuromodulation Corporation*, Case No. 3:16-cv-06830-VC-MEJ, filed May 24, 2018, 9 pages.
Exhibit 12 for Declaration of Carson D. Anderson in Support of Boston Scientific's Reply in Support of Motion for Summary Judgement (Document 398-13), Declaration of James Thacker under 37 CFR 1.1.32, dated Jun. 6, 2013, *Nevro Corp.* vs. *Boston Scientific Corporation and Boston Scientific Neuromodulation Corporation*, Case No. 3:16-cv-06830-VC-MEJ, filed May 24, 2018, 9 pages.
Exhibit 13 for Declaration of Carson D. Anderson in Support of Boston Scientific's Reply in Support of Motion for Summart Judgement (Document 398-14), Copy of Information Disclosure Statement SB-08 Form for U.S. Appl. No. 14/525,134, *Nevro Corp.* vs. *Boston Scientific Corporation and Boston Scientific Neuromodulation Corporation*, Case No. 3:16-cv-06830-VC-MEJ, filed May 24, 2018, 13 pages.
Exhibit 14 for Declaration of Carson D. Anderson in Support of Boston Scientific's Reply in Support of Motion for Summary Judgement (Document 398-15), Copy of Amendment in Response to Final Office Action for U.S. Appl. No. 12/765,685, filed Sep. 19, 2013, *Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 15 for Declaration of Carson D. Anderson in Support of Boston Scientific's Reply in Support of Motion for Summary Judgement (Document 398-16), Copy of Amendment in Response to Non-Final Office Action for U.S. Appl. No. 13/830,992, filed Feb. 24, 2014, *Nevro Corp.* vs. *Boston Scientific Corporation and Boston Scientific Neuromodulation Corporation*, Case No. 3:16-cv-06830-VC-MEJ, filed May 24, 2018, 15 pages.
Exhibit 16 for Declaration of Carson D. Anderson in Support of Boston Scientific's Reply in Support of Motion for Summary Judgement (Document 398-17), Copy of Amendment in Response to Final Office Action for U.S. Appl. No. 14/292,671, filed Jan. 17,

(56) References Cited

OTHER PUBLICATIONS

2017, *Nevro Corp.* vs. *Boston Scientific Corporation and Boston Scientific Neuromodulation Corporation*, Case No. 3:16-cv-06830-VC-MEJ, filed May 24, 2018, 12 pages.
Declaration of J. Lawrence Stevens in Support of Boston Scientific's Reply in Support of Motion for Summary Judgement (Document 398-18), *Nevro Corp.* vs. *Boston Scientific Corporation and Boston Scientific Neuromodulation Corporation*, Case No. 3:16-cv-06830-VC-MEJ, filed May 24, 2018, 34 pages.
Boston Scientific's Response to the Summons to Attend Oral Proceedings for European Patent No. 2207587, *Nevro Corp.* vs. *Boston Scientific Neuromodulation Corporation*, filed Sep. 6, 2018, 31 pages.
Boston Scientific's Responsive Claim Construction Brief, Opposition to in Nevro's Motion for Summary Judgment and Opening Motion for Summary Judgment (Document 358), *Nevro Corp.* vs. *Boston Scientific Corporation and Boston Scientific Neuromodulation Corporation*, Case No. 3:16-cv-06830-VC-MEJ, filed Apr. 26, 2018, 60 pages.
Declaration of Rafael Carbunaru in Support of Boston Scientific Administrative Motion to File under Seal Portions of Boston Scientific's Opposition to Nevro's Motion to Strike BSC's Undisclosed Invalidity Theories and Supporting Documents (Document 355-2), *Nevro Corp.* vs. *Boston Scientific Corporation and Boston Scientific Neuromodulation Corporation*, Case No. 3:16-cv-06830-VC-MEJ, filed Apr. 26, 2018, 3 pages.
Declaration of Sridhar Kothandaraman (Document 356-1), *Nevro Corp.* vs. *Boston Scientific Corporation and Boston Scientific Neuromodulation Corporation*, Case No. 3:16-cv-06830-VC-MEJ, filed Apr. 26, 2018, 4 pages.
Exhibit B to the Declaration of Clara W. Wang in Support of Nevro's Administrative Motion to File under Seal Portions of Nevro's Reply to Strike BSC's Invalidity Positions and Supporting Documents (Document 368-4), *Nevro Corp.* vs. *Boston Scientific Corporation and Boston Scientific Neuromodulation Corporation*, Case No. 3:16-cv-06830-VC-MEJ, filed May 7, 2018, 10 pages.
Order Re: Claim Construction and Cross-Motions for Summary Judgement (Document 449), *Nevro Corp.* vs. *Boston Scientific Corporation and Boston Scientific Neuromodulation Corporation*, Case No. 3:16-cv-06830-VC-MEJ, filed Jul. 24, 2018, 9 pages.
Tentative Ruling (Document 422), *Nevro Corp.* vs. *Boston Scientific Corporation and Boston Scientific Neuromodulation Corporation*, Case No. 3:16-cv-06830-VC-MEJ, filed Jul. 5, 2018, 3 pages.
Nevro Written Submissions for European Patent No. 2207587, Opponents: Medtronic Inc., and Boston Scientific Neuromodulation Corporation, dated Jul. 24, 2018, 9 pages.
Notice of Opposition for European Patent No. 3156099, Proprietor of the Patent: Nevro Corporation; Opponent: Boston Scientific Neuromodulation Corporation, Dec. 15, 2017, 27 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, 2018, 9 pages.
Corrected Rebuttal Expert Report of Ben Pless Regarding Validity on behalf of Plaintiff Nevro Corp., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Mar. 5, 2018, 785 pages.
Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Jan. 18, 2018, 958 pages.
Nevro—Leadership Through Innovation, J. P. Morgan 36th Annual Healthcare Conference, Jan. 7, 2018, 21 pages.
Nevro Observations and Response to Notice of Oppositions filed by Medtronic Inc., and Boston Scientific for European Patent No. 2586488, dated May 18, 2018, 87 pages.
Opponents Boston Scientific Neuromodulation Corporation: Response to Appeal in Opposition for European Patent No. 2243510, dated May 2, 2018, 31 pages.
Opponents Medtronic, Inc.: Response to Appeal in Opposition for European Patent No. 2243510, dated Apr. 30, 2018, 23 pages.
Rebuttal Expert Report of Richard T. Mihran, Ph.D., regarding Invalidity of U.S. Pat. Nos. 8,712,533, 9,327,125, 8,359,102, 9,480,842, 9,333,357, 8,792,988, and 8,768,472, *Nevro Corp.* vs. *Boston Scientific Corporation and Boston Scientific Neuromodulation Corporation*, Case No. 3:16-cv-06830-VC-MEJ, Feb. 14, 2018, 195 pages.
Renew Neurostimulation System—Clinician's Manual—Advanced Neuromodulation Systems, Life Gets Better, 2000, 77 pages.
Summons to Attend Oral Proceedings pursuant to Rule 115(1) EPC for European Patent No. 2207587, Applicant: Nevro Corporation, dated Mar. 9, 2018, 15 pages.
Medtronic's Response to the Summons to Attend Oral Proceedings for European Patent No. 2853285, *Nevro Corp.* vs. *Boston Scientific Neuromodulation Corporation and Medtronic, Inc.*, filed Nov. 30, 2018, 8 pages.
Boston Scientific's Response to the Summons to Attend Oral Proceedings for European Patent No. 2853285, *Nevro Corp.* vs. *Boston Scientific Neuromodulation Corporation and Medtronic, Inc*, filed Nov. 30, 2018, 5 pages.
Brief for Plaintiff-Appellant Nevro Corp., *Nevro Corp.* vs. *Boston Scientific Corporation and Boston Scientific Neuromodulation Corporation*, Case No. 3:16-cv-06830-VC-MEJ, filed Nov. 8, 2018, 341 pages.
Decision Rejecting the Opposition (Art. 101(2) EPC) for European Patent No. 2207587, *Nevro Corp.* vs. *Boston Scientific Neuromodulation Corporation and Medtronic*, Inc., Jan. 4, 2019, 18 pages.
Provision of a Copy of Minutes in accordance with Rule 124(4) EPC for Opposition by Medtronic, Inc., and Boston Scientific Neuromodulation Corporation for European Patent No. 2207587, dated Jan. 4, 2019, 10 pages.
Medtronic's Submissions Commenting on the Auxiliary Requests for European Patent No. 2853285, *Nevro Corp.* vs. *Boston Scientific Neuromodulation Corporation and Medtronic, Inc*, filed Jan. 11, 2019, 13 pages.
Medtronic—Spinal Cord Stimulation (SCS) Patient Management Guidelines for Clinicians, 1999, 114 pages.
Nevro—Leadership Through Innovation, J. P. Morgan 36th Annual Healthcare Conference, Jan. 24, 2019, 2 pages.
Notice of Opposition for European Patent No. 3156099, Proprietor of the Patent: Nevro Corporation; Opponent: Medtronic, Inc., dated Mar. 11, 2019, 31 pages.
Opponent Response to Patent Proprietor Comments to Declaration of Dr. Baranidharan for European Patent No. 2630984, dated Nov. 8, 2016, 3 pages.
Opponents Boston Scientific Neuromodulation Corporation.: Statement Setting Out the Grounds of Appeal for European Patent No. 2207587, dated May 2, 2019, 12 pages.
Opponents Medtronic, Inc.: Response to Grounds of Appeal for European Patent No. 2630984, dated Dec. 19, 2017, 23 pages.
Opponents Medtronic, Inc.: Statement Setting Out the Grounds of Appeal for European Patent No. 2207587, dated May 19, 2019, 21 pages.

\* cited by examiner

SPINAL CORD MODULATION FOR INDUCING PARESTHETIC AND ANESTHETIC EFFECTS, AND ASSOCIATED SYSTEMS AND METHODS

CROSS-REFERENCE TO RELATED APPLICATION

The present application is a continuation of U.S. patent application Ser. No. 12/765,685, filed Apr. 22, 2010, which claims priority to U.S. Provisional Application 61/171,790, filed on Apr. 22, 2009, both of which are incorporated herein by reference.

TECHNICAL FIELD

The present disclosure is directed generally to spinal cord modulation for inducing paresthetic and anesthetic effects, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

DETAILED DESCRIPTION

The present disclosure is directed generally to spinal cord modulation and associated systems and methods that induce, produce, generate, or otherwise cause paresthetic and anesthetic effects in a patient. Such systems and methods can be used to treat patient pain. Specific details of certain embodiments of the disclosure are described below with reference to methods for modulating one or more target neural populations or sites of a patient, and associated implantable structures for providing the modulation. Although selected embodiments are described below with reference to modulating the dorsal root and/or other particular regions of the spinal column to control pain, the leads may be in some instances be used to modulate other neurological structures of the spinal cord. Some embodiments can have configurations, components or procedures different than those described in this section, and other embodiments may eliminate particular components or procedures. A person of ordinary skill in the relevant art, therefore, will understand that the invention may have other embodiments with additional elements, and/or may have other embodiments without several of the features shown and described below with reference to FIGS. 1-6.

In general terms, aspects of many of the following embodiments are directed to producing a sensation (e.g., paresthesia or a paresthetic effect) in the patient, in addition to producing a therapeutic effect (e.g., anesthesia or an anesthetic effect) in the patient. The therapeutic effect can be produced by inhibiting, suppressing, downregulating, blocking, preventing, or otherwise modulating the activity of the affected neural population (e.g., nerve cells). Such embodiments may be useful in cases for which the patient benefits from an anesthetic effect, but, because the anesthetic effect typically creates an absence of pain and/or other sensations, the patient may require the assurance or comfort of a detectable sensation. By supplementing the anesthetic effect with a paresthetic effect, which is detected by the patient, the patient and/or the associated practitioner can better monitor the manner in which the anesthesia-producing signals are provided. In other embodiments, the patient and/or the practitioner may have other bases for supplementing anesthesia-producing signals with paresthesia-producing signals. Further details are described below with reference to FIGS. 1-6.

Figure 1:
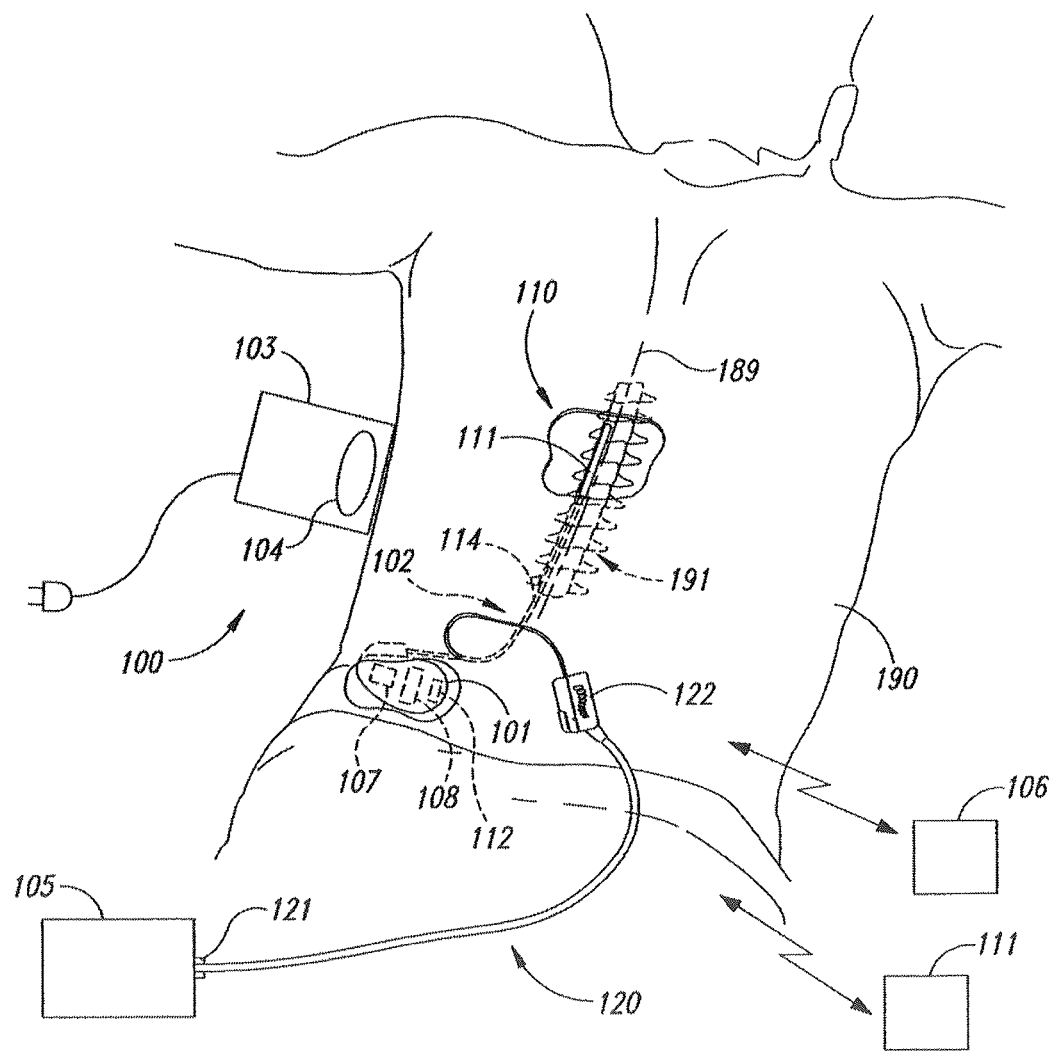
FIG. 1 is a partially schematic illustration of an implantable spinal cord modulation system positioned at the spine to deliver therapeutic signals in accordance with an embodiment of the present disclosure.

FIG. 1 schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 110. In a representative example, the signal delivery element 110 includes a lead or lead body 111 that carries features for delivering therapy to the patient 190 after implantation. The pulse generator 101 can be connected directly to the lead body 111, or it can be coupled to the lead body 111 via a communication link 102 (e.g., an extension). Accordingly, the lead 111 can include a terminal section that is releasably connected to an extension at a break 114

(shown schematically in FIG. 1). This allows a single type of terminal section to be used with patients of different body types (e.g., different heights). As used herein, the terms lead and lead body include any of a number of suitable substrates and/or support members that carry devices for providing therapy signals to the patient 190. For example, the lead body 111 can include one or more electrodes or electrical contacts that direct electrical signals into the patient's tissue, such as to provide for patient relief. In other embodiments, the signal delivery element 110 can include devices other than a lead body (e.g., a paddle) that also direct electrical signals and/or other types of signals to the patient 190.

The pulse generator 101 can transmit signals to the signal delivery element 110 that up-regulate (e.g., stimulate or excite) and/or down-regulate (e.g., block or suppress) target nerves. As used herein, and unless otherwise noted, the terms "modulate" and "modulation" refer generally to signals that have either type of effect on the target nerves. The pulse generator 101 can include a machine-readable (e.g., computer-readable) medium containing instructions for generating and transmitting suitable therapy signals. The pulse generator 101 and/or other elements of the system 100 can include one or more processors 107, memories 108 and/or input/output devices. Accordingly, the process of providing modulation signals (e.g., electrical signals) and executing other associated functions can be performed by computer-executable instructions contained on computer-readable media, e.g., at the processor(s) 107 and/or memory(s) 108. The pulse generator 101 can include multiple portions, elements, and/or subsystems (e.g., for directing signals in accordance with multiple signal delivery parameters), housed in a single housing, as shown in FIG. 1, or in multiple housings.

The pulse generator 101 can also receive and respond to an input signal received from one or more sources. The input signals can direct or influence the manner in which the therapy instructions are selected, executed, updated and/or otherwise performed. The input signal can be received from one or more sensors 112 (one is shown schematically in FIG. 1 for purposes of illustration) that are carried by the pulse generator 101 and/or distributed outside the pulse generator 101 (e.g., at other patient locations) while still communicating with the pulse generator 101. The sensors 112 can provide inputs that depend on or reflect patient state (e.g., patient position, patient posture and/or patient activity level), and/or inputs that are patient-independent (e.g., time). In other embodiments, inputs can be provided by the patient and/or the practitioner, as described in further detail later. Still further details are included in co-pending U.S. application Ser. No. 12/703,683, filed on Feb. 10, 2010 and incorporated herein by reference.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In some cases, an external programmer 105 (e.g., a trial modulator) can be coupled to the signal delivery element 110 during an initial implant procedure, prior to implanting the pulse generator 101. For example, a practitioner (e.g., a physician and/or a company representative) can use the external programmer 105 to vary the signal delivery parameters provided to the signal delivery element 110 in real time, and select optimal or particularly efficacious parameters. These parameters can include the position of the signal delivery element 110, as well as the characteristics of the electrical signals provided to the signal delivery element 110. In a typical process, the practitioner uses a cable assembly 120 to temporarily connect the external programmer 105 to the signal delivery device 110. The cable assembly 120 can accordingly include a first connector 121 that is releasably connected to the external programmer 105, and a second connector 122 that is releasably connected to the signal delivery element 110. Accordingly, the signal delivery element 110 can include a connection element that allows it to be connected to a signal generator either directly (if it is long enough) or indirectly (if it is not). The practitioner can test the efficacy of the signal delivery element 110 in an initial position. The practitioner can then disconnect the cable assembly 120, reposition the signal delivery element 110, and reapply the electrical modulation. This process can be performed iteratively until the practitioner obtains the desired position for the signal delivery device 110. Optionally, the practitioner may move the partially implanted signal delivery element 110 without disconnecting the cable assembly 120. Further details of suitable cable assembly methods and associated techniques are described in co-pending U.S. application Ser. No. 12/562, 892, filed on Sep. 18, 2009, and incorporated herein by reference.

During this process, the practitioner can also vary the position of the signal delivery element 110. After the position of the signal delivery element 110 and appropriate signal delivery parameters are established using the external programmer 105, the patient 190 can receive therapy via signals generated by the external programmer 105, generally for a limited period of time. In a representative application, the patient 190 receives such therapy for one week. During this time, the patient wears the cable assembly 120 and the external programmer 105 outside the body. Assuming the trial therapy is effective or shows the promise of being effective, the practitioner then replaces the external programmer 105 with the implanted pulse generator 101, and programs the pulse generator 101 with parameters selected based on the experience gained during the trial period. Optionally, the practitioner can also replace the signal delivery element 110. Once the implantable pulse generator 101 has been positioned within the patient 190, the signal delivery parameters provided by the pulse generator 101 can still be updated remotely via a wireless physician's programmer (e.g., a physician's remote) 111 and/or a wireless patient programmer 106 (e.g., a patient remote). Generally, the patient 190 has control over fewer parameters than does the practitioner. For example, the capability of the patient programmer 106 may be limited to starting and/or stopping the pulse generator 101, and/or adjusting signal amplitude.

In any of these foregoing embodiments, the parameters in accordance with which the pulse generator 101 provides signals can be modulated during portions of the therapy regimen. For example, the frequency, amplitude, pulse width and/or signal delivery location can be modulated in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation.

Figure 2:
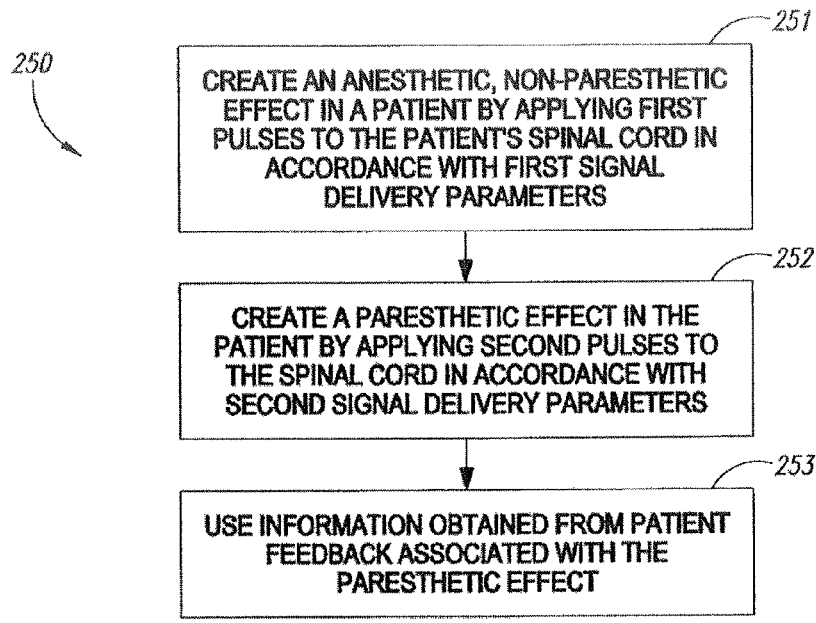
FIG. 2 is a flow diagram illustrating a method for treating a patient in accordance with a particular embodiment of the disclosure.

FIG. 2 is a schematic flow diagram illustrating a process 250 for treating a patient in accordance with particular embodiments of the disclosure. The process 250 can include creating both a therapeutic effect and a sensation in a patient by delivering first pulses (e.g., first electrical pulses) having a first set of signal delivery parameters, and second pulses (e.g., second electrical pulses) having a second set of signal delivery parameters. A first value of at least one parameter of the first set is different than a second value of a corresponding second parameter of the second set, and the first pulses, second pulses, or both are delivered to the patient's spinal cord. In particular embodiments, the effects on the patient may be separately attributable to each of the first and second pulses, but in other embodiments, the effects need not be attributed in such a manner. In one embodiment, the process 250 can include creating an anesthetic, non-paresthetic effect in the patient by applying first pulses to the patient's spinal cord in accordance with first signal delivery parameters (process portion 251). In general, the anesthetic, non-paresthetic effect is one that addresses the patient's pain by blocking or otherwise eliminating the sensation of pain, without creating a sensation for the patient. In particular embodiments, the anesthetic, non-paresthetic effect of the first pulses can have one or both of the following characteristics. One characteristic is that the anesthetic, non-paresthetic effect is undetected by the patient. Another characteristic is that the anesthetic, non-paresthetic effect produces a reduction or elimination of pain.

In process portion 252, a paresthetic effect is created in the patient by applying second pulses to the spinal cord in accordance with second signal delivery parameters. In general terms, an aspect of at least one of the second signal delivery parameters is different than an aspect of the corresponding first signal delivery parameter, so as to produce a paresthetic effect rather than an anesthetic, non-paresthetic effect. In particular embodiments, the paresthetic effect creates a tingling and/or other patient-detectable sensation. In process portion 253, information obtained from the patient's feedback to the paresthetic effect is used. For example, the patient and/or practitioner may use this information to understand that the system is in an "on" state rather than an "off" state, and/or to determine whether the lead is properly or improperly placed, and/or to obtain an indication of the amplitude or signal strength provided by the system. In other embodiments, the process can include obtaining different information and/or taking different actions. Further details of representative methods employing variations of some or all of the foregoing steps are described below with reference to FIGS. 3A-3F.

Figure 3A:
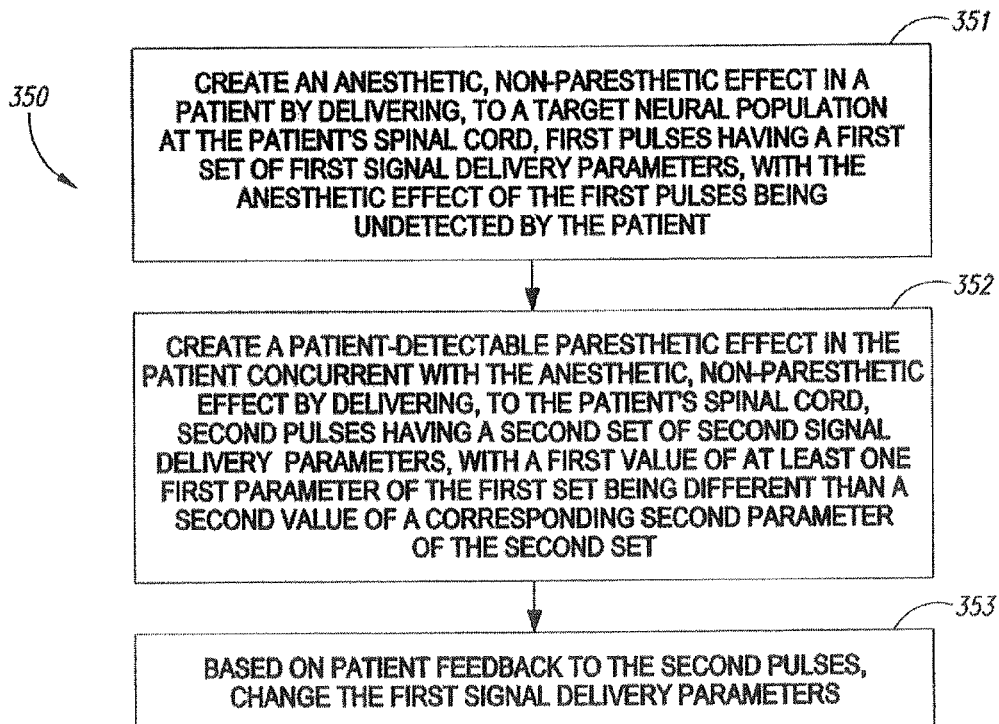
FIGS. 3A-3F are flow diagrams illustrating further methods for treating a patient in accordance with further embodiments of the disclosure.

In some cases, the pain experienced by the patient (and addressed with the methods and systems of the present disclosure) may not be experienced by the patient on a continual basis. For example, in some instances, the patient may experience pain while standing or walking, but not while lying down. In such instances, it can be difficult to accurately conduct the pre-implant procedure described above with reference to FIG. 1. During such a procedure, the patient is typically lying down in a prone position while the practitioner adjusts the signal delivery parameters associated with signals provided by the signal delivery element (e.g., waveform parameters, active electrodes, and/or the position of the signal delivery element). FIG. 3A is a schematic flow diagram illustrating a process 350 that can address the foregoing case. Process 350 can include creating an anesthetic, non-paresthetic effect in a patient by delivering, to a target neural population at the patient's spinal cord, first pulses having a first set of first signal delivery parameters, with the anesthetic effect of the first pulses being undetected by the patient. This is an example of the first characteristic described above with reference to FIG. 2. Because the anesthetic effect of the first pulses is undetected by the patient, process 350 can further include creating a patient-detectable paresthetic effect in the patient, concurrent with the anesthetic, non-paresthetic effect (process portion 352). This process can be accomplished by delivering, to the patient's spinal cord, second pulses having a second set of signal delivery parameters. A first value of at least one first parameter of the first set of signal delivery parameters is different than a second value of a corresponding second parameter of the second set, e.g., to produce the paresthetic effect. In this process, the corresponding parameters of the first and second sets are analogous. For example, if the frequency of the second pulses is different than the frequency of the first pulses to produce a paresthetic effect, the two frequencies can be considered corresponding parameters. Based on patient feedback to the second pulses, the first signal delivery parameters are changed (process portion 353), generally by the practitioner.

As noted above, some patients may experience pain while standing or walking, but not while lying down. Because the patient is typically lying down while the practitioner adjusts the signal delivery parameters, it may not be immediately evident that the parameters are creating the desired effect in the patient. Accordingly, the practitioner can position the signal delivery device at a site expected to produce the desired anesthetic, non-paresthetic effect in the patient, and can accompany the signals intended to produce that effect with signals that deliberately produce a patient-detectable paresthetic effect. When the patient begins to report a paresthetic effect, the practitioner can have an enhanced degree of confidence that the signal delivery parameters that are common to both the first pulses (which produce the anesthetic effect) and the second pulses (which produce the paresthetic effect) are properly selected. These signal delivery parameters can include the location at which the signal is delivered, the strength (e.g., amplitude) of the signal, and/or other parameters. If, based on patient feedback to the second pulses, the parameter values can be improved, the practitioner can change the first signal delivery parameters, e.g., by moving the lead, applying signals to different contacts on the lead, changing signal strength and/or making other adjustments. In a particular example, this arrangement can reduce the likelihood that the practitioner will inadvertently increase the amplitude of the anesthesia-producing first pulses to a level that will produce discomfort and/or muscle activation when the patient changes position. In other embodiments, other signal delivery parameters may be adjusted, as described further below with reference to FIGS. 3B-3F. In any of these embodiments, the second signal delivery parameters can also be changed, e.g., in parallel with changes to the first signal delivery parameters, so that the practitioner continues to receive feedback from the patient based on the paresthetic effect created by the second pulses.

Figure 3B:
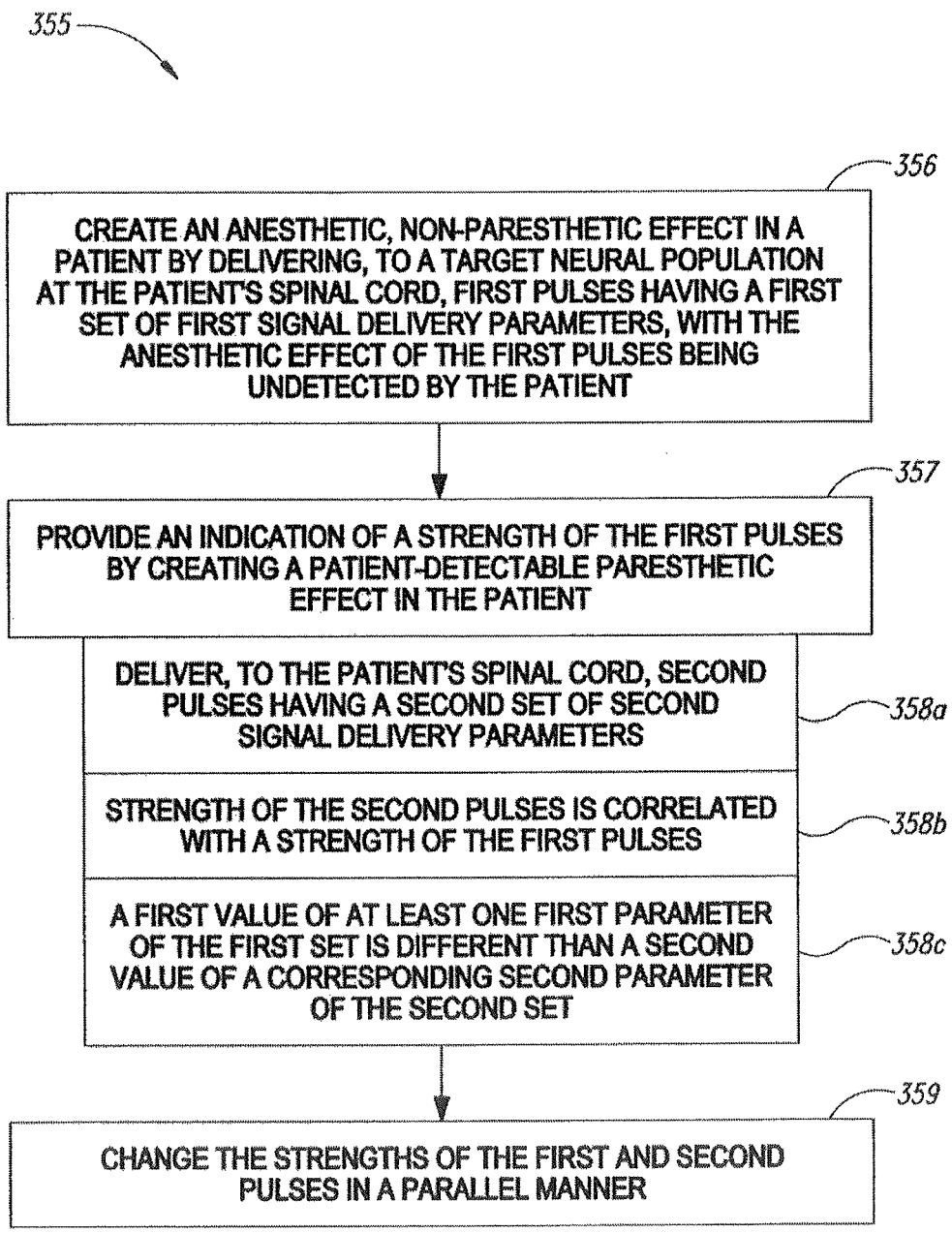

FIG. 3B illustrates another representative process 355 for treating a patient, and includes creating an anesthetic, non-paresthetic effect in the patient (process portion 356), generally similar to process portion 351 described above. The anesthetic, non-paresthetic effect is typically manifested as a perceived reduction or elimination of pain, and so represents an example of the second characteristic described above with reference to FIG. 2. In process portion 357, the process 355 includes providing an indication of a strength of the first pulses by creating a patient-detectable paresthetic effect in the patient. This can in turn include delivering to the patient's spinal cord second pulses having a second set of signal delivery parameters (process portion 358a), with the strength of the second pulses being correlated with a strength of the first pulses (process portion 358b) and with a first value of at least one parameter of the first set being different than a second value of a corresponding second parameter of the second set (process portion 358c). For example, the frequency of the first pulses may be different than the frequency of the second pulses. In process portion 359, the strengths of the first and second pulses are changed in a parallel manner. For example, as the strength of the first pulses is increased, the strength of the second pulses can also be increased. Accordingly, when the patient reports a sensation of paresthesia resulting from the second pulses, the practitioner can effectively obtain an indication of the strength of the first pulses, even though the patient may not be able to report a direct effect of the first pulses. In one aspect of this embodiment, the strengths of the first and second pulses may be identical, and may be changed in identical manners. In other embodiments, this may not be the case. For example, in a particular embodiment, the practitioner may be aware of a typical offset between the strength of a pulse that is suitable for creating an anesthetic effect and the strength of a pulse that is sufficient to create a paresthetic effect. In such instances, the practitioner may build this offset into the manner in which the two sets of pulses are changed to preserve a desired correlation between the onset of a patient-detectable effect created by the second pulses and an expected anesthetic effect created by the first pulses. The amplitude or intensity of the second pulses can be significantly less than that associated with standard SCS systems. This can be the case for at least the reason that in at least some embodiments, the second pulses are not necessarily intended to mask pain (as they are in standard SCS treatments), but rather are intended to create a patient-detectable sensation. When this is the case, delivering the second pulses can use less energy than delivering standard SCS pulses. In addition to or in lieu of this potential benefit, the second pulses can allow the practitioner more flexibility in setting an appropriate intensity level because a wider range of intensity levels (e.g., extending to lower values than are associated with standard SCS) are expected to produce the desired patient sensation.

Figure 3C:
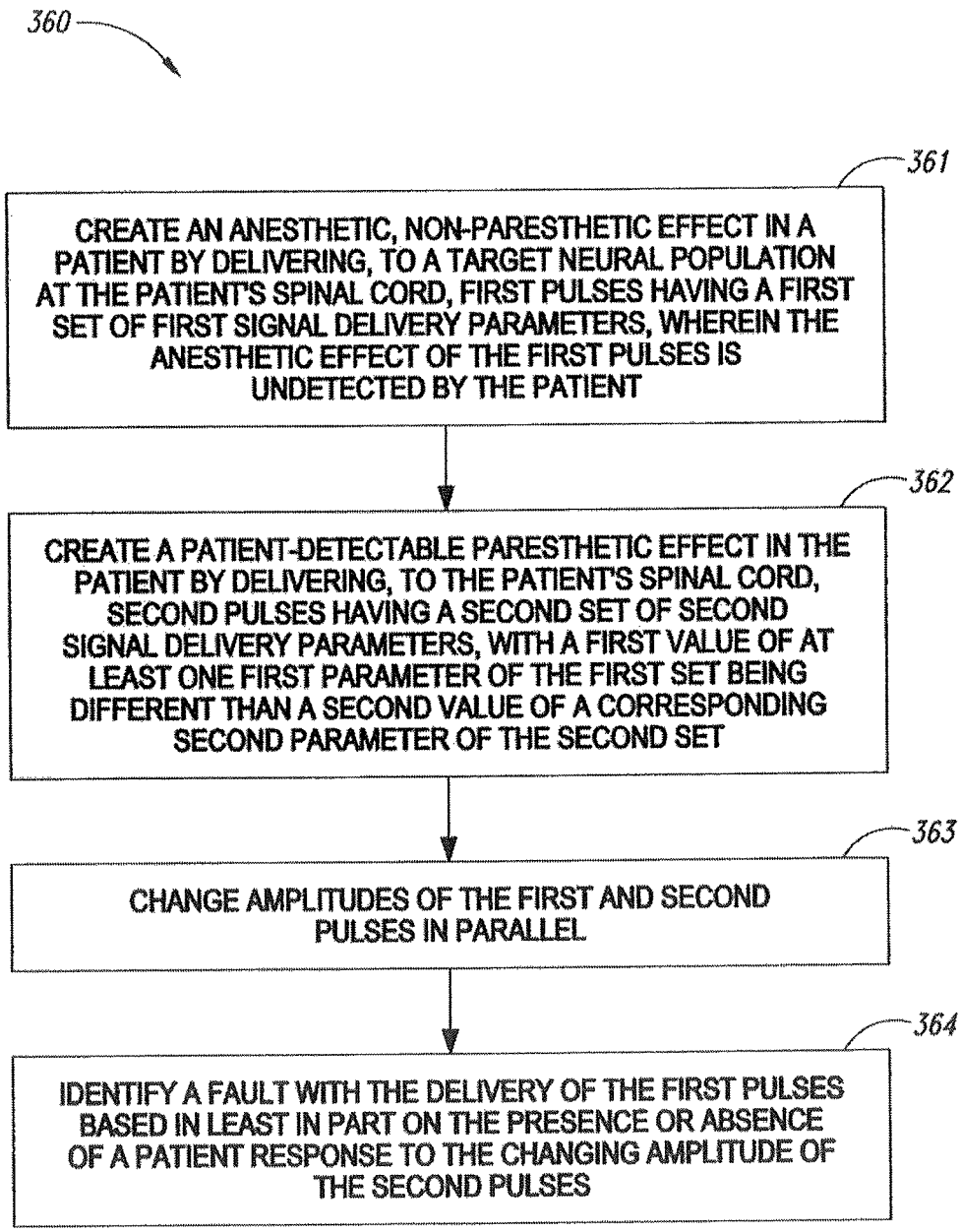

In addition to or in lieu of providing feedback that may be used to adjust signal delivery parameters associated with the first pulses (e.g., the anesthesia-producing pulses), aspects of the foregoing process may be used to identify faults (e.g., defects, abnormalities and/or unexpected states) associated with the system at an early stage. For example, FIG. 3C illustrates a process 360 that includes creating an anesthetic, non-paresthetic effect in the patient (process portion 361) that is undetected by the patient, and that is accompanied by creating a patient-detectable paresthetic effect (process portion 362) generally similar to process portion 352 described above. In process portion 363, the amplitudes of the first and second pulses are changed in parallel. In one representative process, the amplitudes are increased and, in other processes, the amplitudes can be decreased.

Process portion 364 includes identifying a fault with the delivery of the first pulses based at least in part on the presence or absence of a patient response to the changing amplitude of the second pulses. For example, while the patient may be unable to detect whether or not the first pulses are being delivered, the practitioner can increase the amplitude of both the first and second pulses to a point at which the practitioner would expect the patient to report a paresthetic effect created by the second pulses. If the patient fails to report such an effect, the practitioner may be alerted to a fault in the signal delivery system that applies to both delivery of the first pulses and the second pulses. Accordingly, the practitioner can rectify the fault and continue the process of establishing suitable signal delivery parameters for the first pulses, and optionally, the second pulses as well. The fault may be that the system is not on, that there is an electrical discontinuity between the signal generator and the lead contacts, that an element of the signal generator or lead has failed, and/or that the system has another abnormality or unexpected characteristic. In other embodiments, the fault can be identified by the presence of a patient response, rather than the absence of a patient response. For example, if the patient reports a sensation when no sensation is expected (e.g., if the patient reports muscle cramping, sensation and/or stimulation), this may indicate a system fault. In other cases, this may indicate a misplaced lead, or a patient with a lower than expected activation threshold.

Figure 3D:
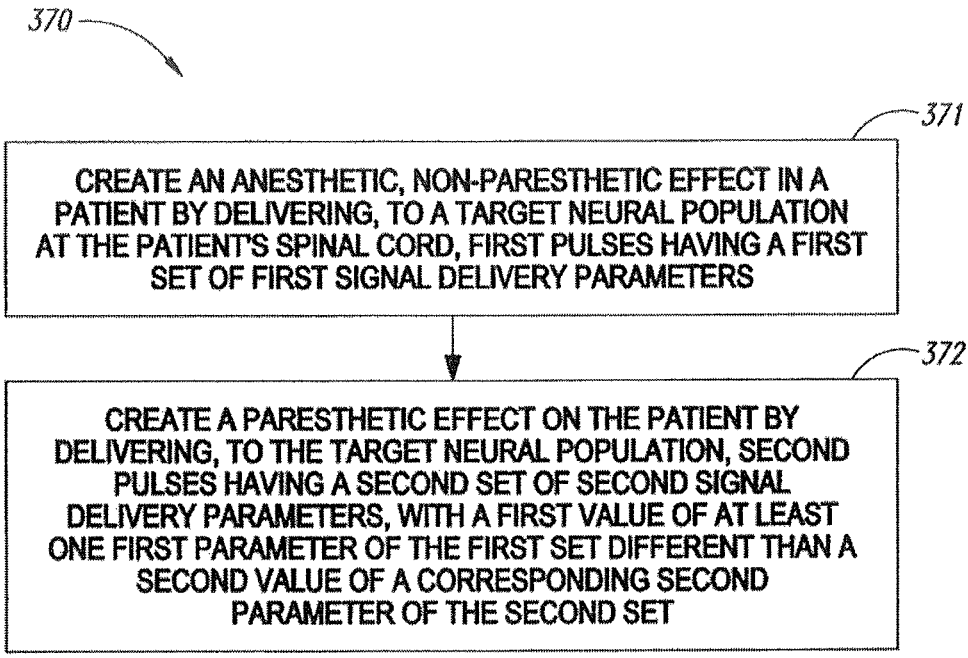

FIG. 3D illustrates a process 370 that includes directing both the first and second pulses to the same target neural population of the patient. Accordingly, process 370 includes creating an anesthetic, non-paresthetic effect in a patient by delivering to a target neural population at the patient's spinal cord, first pulses having a first set of first signal delivery parameters (process portion 371). The process 370 further includes creating a paresthetic effect in the patient by delivering, to the same target neural population, second pulses having characteristics generally similar to those discussed above with reference to process portion 352 (e.g., at least one parameter value differing from a corresponding parameter value of the first pulses). In this embodiment, the first and second pulses are delivered to the same target neural population, for example, when it is expected that other target neural populations may not have a known correlation between patient responses to the second pulses, and patient effects created by the first pulses. In cases where such a correlation is known, the second signals can be applied to a different neural population than the first pulses. For example, as is discussed further with reference to FIGS. 5A and 5B, if one neural population is susceptible to paresthesia but not anesthesia, the practitioner may wish to apply the second pulses to a different neural population than the first pulses.

Figure 3E:
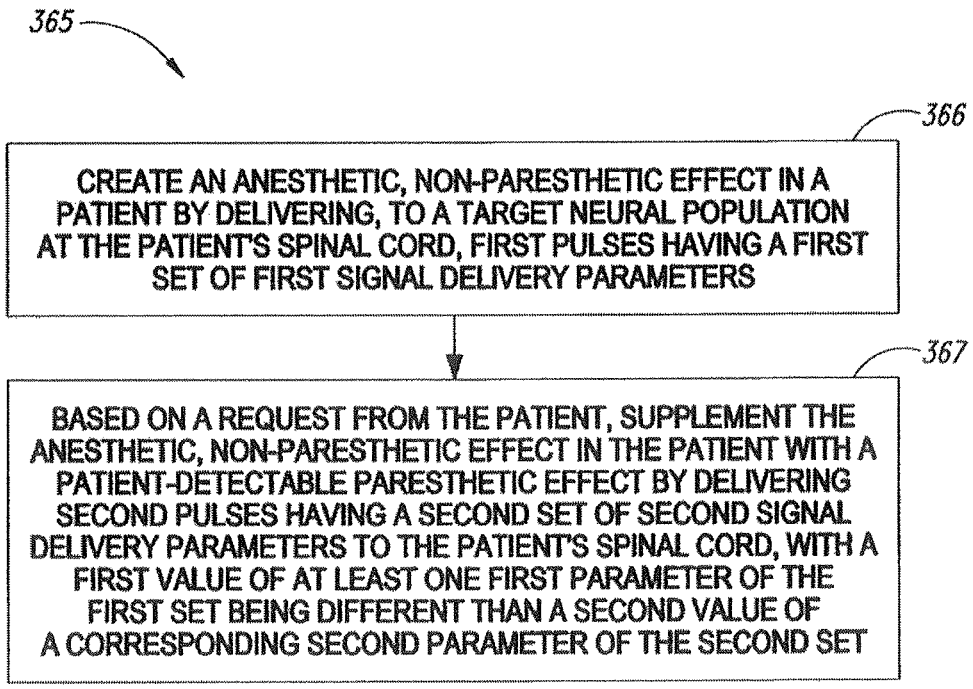

FIG. 3E is a flow diagram illustrating a process 365 in which a paresthetic effect is provided to the patient in response to a patient request. Process 365 includes creating an anesthetic, non-paresthetic effect in the patient by delivering, to a target neural population at the patient's spinal cord, first pulses having a first set of first signal delivery parameters (process portion 366). Process portion 367 includes supplementing the anesthetic, non-paresthetic effect in the patient with a patient-detectable, paresthetic effect, based on a request from the patient. This process can in turn include delivering to the patient's spinal cord, second pulses having a second set of signal delivery parameters, with a first value of at least one first parameter of the first set being different than a second value of a corresponding second parameter of the second set. In a particular embodiment, the patient may request the second pulses to emulate an effect the patient is already familiar with, as described below with reference to FIG. 3F.

Figure 3F:
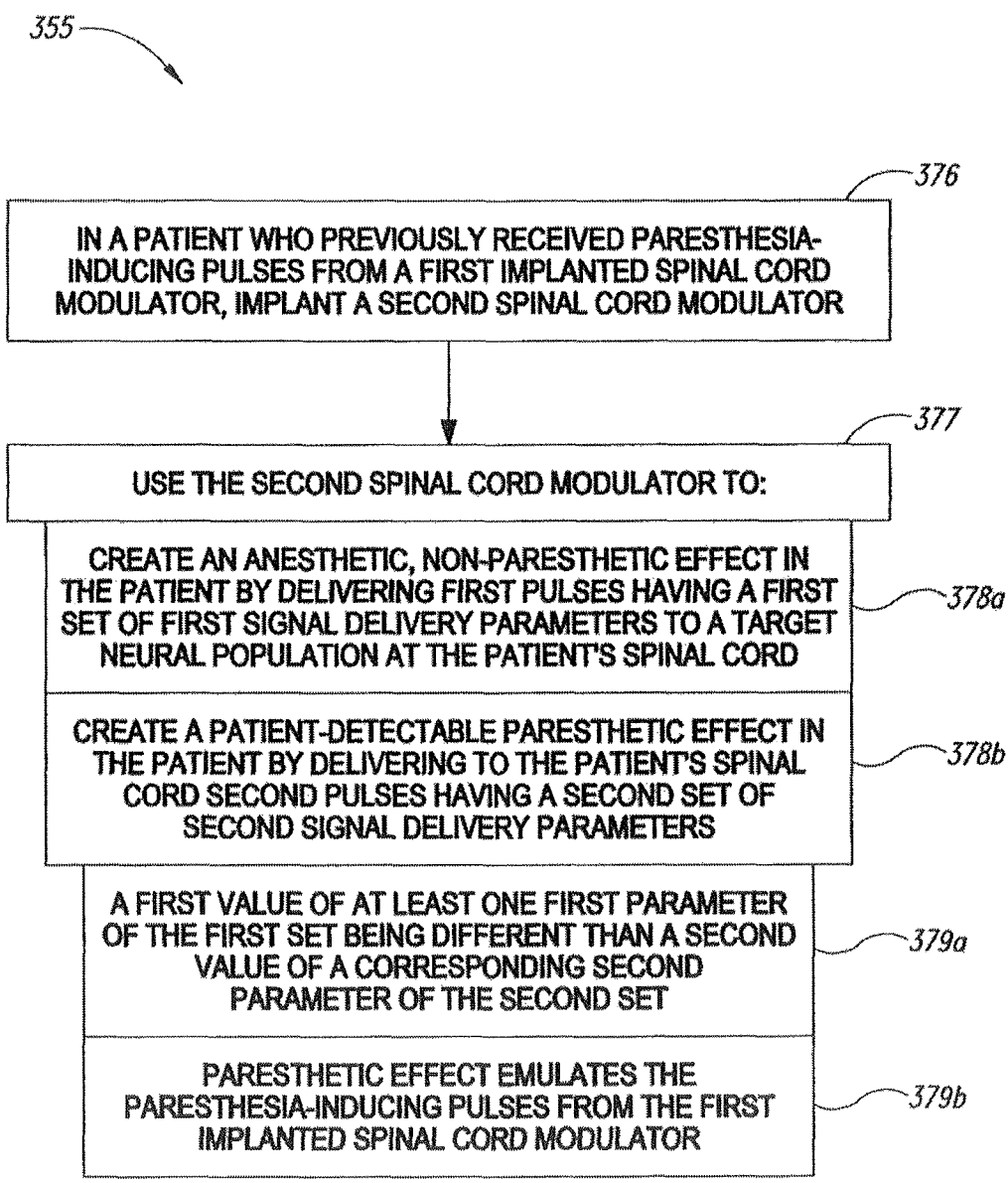

FIG. 3F is a schematic block diagram of a process 375 for treating a patient that, in general terms, includes emulating the paresthesia-inducing effects of a conventional SCS device with a device that provides both anesthesia and paresthesia. Accordingly, the process 375 can include selecting a patient who previously received paresthesia-inducing pulses from a first implanted spinal cord modulator, and implanting a second spinal cord modulator in that patient (process portion 376). In process portion 377, the second spinal cord modulator is used to create an anesthetic, non-paresthetic effect in the patient (process portion 378a), and also a patient-detectable paresthetic effect (process portion 378b), using different signal delivery parameters (process portion 379a). The signal delivery parameters can be selected to emulate the paresthesia-inducing pulses from the first implanted spinal cord modulator (process portion 379b). This arrangement can be used for patients who prefer to retain the paresthetic effect obtained with a conventional SCS device, in addition to obtaining the benefit of an anesthetic effect. The patient may want the paresthetic effect for any of a variety of reasons, including but not limited to the sense of familiarity it may provide, and/or the pleasurable effect of the sensation.

In at least some instances, it may be desirable to the physician or other practitioner to control the amplitude or strength of the anesthesia-producing first pulses, and the patient control the amplitude or strength of the paresthesia-producing second pulses. Accordingly, the system 100 (FIG. 1) delivering the pulses can allow the patient access to the amplitude control of the second pulses, and restrict access to the amplitude control of the first pulses to the practitioner. In this manner, the practitioner can be assured that the anesthetic effect is provided automatically at a selected level, and the patient can control at least some aspects of the sensation-producing second pulses. This is a representative example of the more general case in which the amplitude (and/or other parameters) of the first and second pulses are varied independently of each other. For example, the practitioner may want to vary the frequency of the first pulses while keeping the frequency of the second pulses constant. In other embodiments, the practitioner may want to have the first and second pulses applied with different duty cycles, different pulse widths, different interpulse intervals, and/or other parameters, and so may wish to have independent control over the values of these parameters as they apply to the first pulses, independent of the values of the these parameters as they apply to the second pulses.

Figure 4:
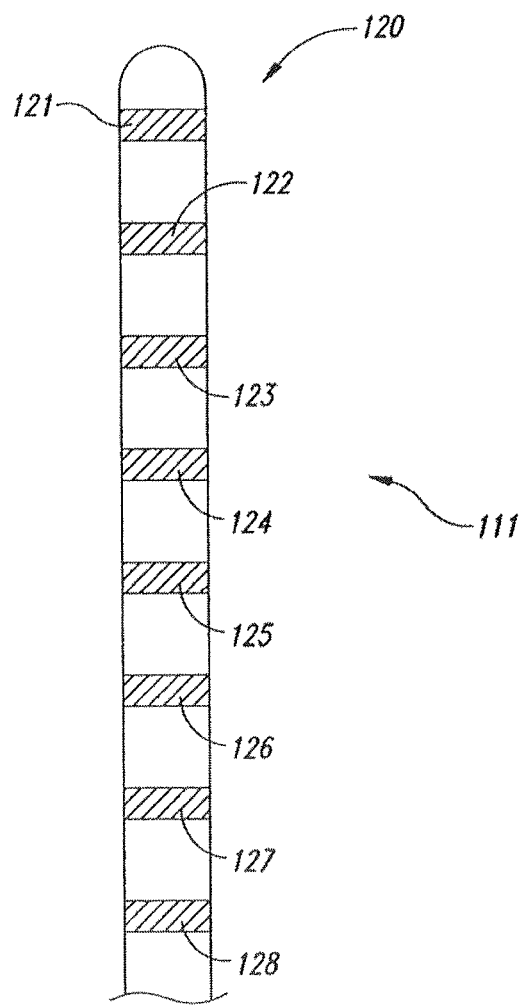
FIG. 4 is a schematic illustration of a representative lead body suitable for providing modulation to a patient in accordance with several embodiments of the disclosure.

FIG. 4 is a partially schematic illustration of a lead body 111 that may be used to apply modulation to a patient in accordance with any of the foregoing embodiments. In general, the lead body 111 includes a multitude of electrodes or contacts 120. When the lead body 111 has a circular cross-sectional shape, as shown in FIG. 4, the contacts 120 can have a generally ring-type shape and can be spaced apart axially along the length of the lead body 111. In a particular embodiment, the lead body 111 can include eight contacts 120, identified individually as first, second, third . . . eighth contacts 121, 122, 123 . . . 128. In general, one or more of the contacts 120 are used to provide signals, and another one or more of the contacts 120 provide a signal return path. Accordingly, the lead body 111 can be used to deliver monopolar modulation (e.g., if the return contact is spaced apart significantly from the delivery contact), or bipolar modulation (e.g., if the return contact is positioned close to the delivery contact and in particular, at the same target neural population as the delivery contact).

Figure 5A:
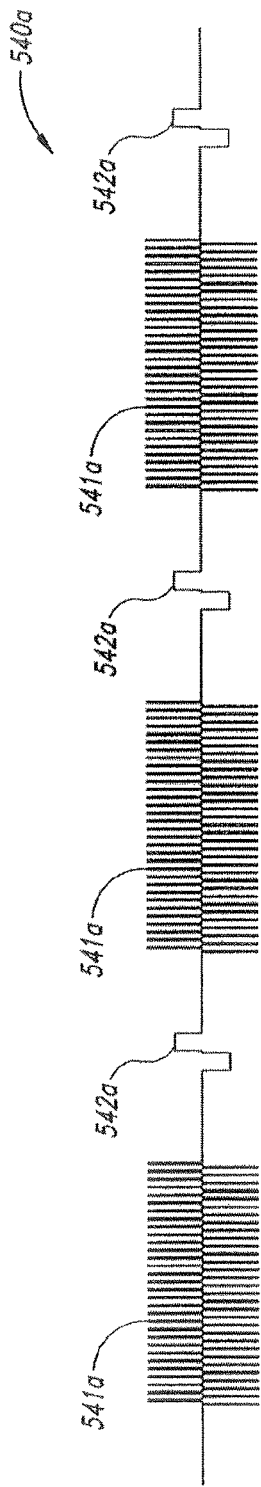
FIGS. 5A-5D illustrate representative wave forms associated with signals applied to patients in accordance with particular embodiments of the disclosure.

FIG. 5A illustrates a representative electrical signal wave form 540a having first pulses 541a and second pulses 542a. In a particular aspect of this embodiment, the first pulses 541a are provided at a higher frequency than are the second pulses 542a. In another embodiment, this relationship can be reversed. A single second pulse 542a can be positioned between sequential bursts of the first pulses 541a (as shown in FIG. 5A), or multiple second pulses 542a can be provided between sequential bursts of the first pulses 541a. In either of these embodiments, the first and second pulses 541a, 542a can be provided to the same contact(s) e.g., so that both sets of pulses are directed to the same target neural population. In such instances, the first and second pulses 541a, 542a generally do not overlap temporally with each other. Accordingly, the practitioner can maintain a suitable level of control over the electric fields produced by each set of pulses. Although the first and second pulses do not overlap, they can be interleaved with each other in such a manner that the effects of each set of pulses (e.g., anesthetic and paresthetic effects) can temporarily overlap. Put another way, the patient can concurrently receive an anesthetic effect and a paresthetic effect from the interleaved pulses. As discussed above, the first and second pulses can be applied to different neural populations in other embodiments.

The first pulses 541a can be provided at a duty cycle that is less than 100%. For example, as shown in FIG. 5A, the first pulses 541a can be provided at a duty cycle of about 60%, meaning that the first pulses 541a are active during 60% of the time interval between sequential second pulses 542a. The first pulses 541a can be provided continuously during each burst (e.g., each first pulse in a burst can be immediately followed by another first burst), or an interpulse interval can be positioned between neighboring first pulses 541a. In a representative embodiment, the interpulse interval between first pulses 541a is 15 microseconds, and in other embodiments, the interpulse interval can have other values, including zero. In the embodiment shown in FIG. 5A, the interpulse interval between neighboring second pulses 542a is filled or partially filled with the first pulses 541a. The first pulses 541a can also include an interphase interval between anodic and cathodic portions of the pulse. The interphase interval can also be 15 microseconds in a representative embodiment, and can have other zero or non-zero values in other embodiments.

In general, the pulse width of the second pulses 542a can be greater than that of the first pulses 541a (as shown in FIG. 5A). In other embodiments, the second pulses 542a can have pulse widths equal to or less than the pulse widths of the first pulses 541a. The amplitude (e.g., current amplitude or voltage amplitude) of the second pulses 542a can be less than the amplitude of the first pulses 541a (as shown in FIG. 5A), or equal to the amplitude of the first pulses 541a, or greater than the amplitude of the first pulses 541a (as described below with reference to FIG. 5B), depending upon whether or not it is beneficial to maintain an offset between the respective amplitudes, as discussed above with reference to FIG. 3B. In particular examples, the first pulses 541a can be delivered at a frequency of from about 1.5 kHz to about 100 kHz, or from about 1.5 kHz to about 50 kHz. In more particular embodiments, the first pulses 541a can be provided at frequencies of from about 3 kHz to about 20 kHz, or from about 3 kHz to about 15 kHz, or from about 5 kHz to about 15 kHz, or from about 3 kHz to about 10 kHz. The amplitude of the first pulses 541a can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. In still further embodiments, the amplitude can be from about 2.0 mA to about 3.5 mA, or from about 1 mA to about 5 mA, about 6 mA, or about 8 mA. The pulse width (e.g., for just the cathodic phase of the pulses) can vary from about 10 microseconds to about 333 microseconds. In further particular embodiments, the pulse width of the first pulses 541*a* can range from about 25 microseconds to about 166 microseconds, or from about 33 microseconds to about 100 microseconds, or from about 50 microseconds to about 166 microseconds. The frequency of the second pulses 542*a* can be in the range of from about 2 Hz to about 1.2 kHz, and in a more particular embodiment, about 60 Hz. The amplitude of the second pulses 542*a* can be from about 1 mA to about 20 mA, and in a particular embodiment, from about 2 mA to about 10 mA. The pulse width of the second pulses 542*a* can range from about 10 microseconds to about 1,000 microseconds. In a further particular embodiment, the pulse width of the second pulses can be from about 100 microseconds to about 1,000 microseconds, and in a still further particular embodiment, can be about 250 microseconds. In at least some embodiments, it is expected that the foregoing amplitudes will be suprathreshold. It is also expected that, in at least some embodiments, the neural response to the foregoing signals will be asynchronous. For example, the frequency of the first pulses 541*a* can be selected to be higher (e.g., between twice and ten times higher) than the refractory period of the target neurons at the patient's spinal cord, which in at least some embodiments is expected to produce an asynchronous response. Further details of representative systems and methods for producing asynchronous neural responses are included in pending U.S. patent application Ser. No. 12/362,244 filed on Jan. 29, 2009 and incorporated herein by reference.

Figure 5B:
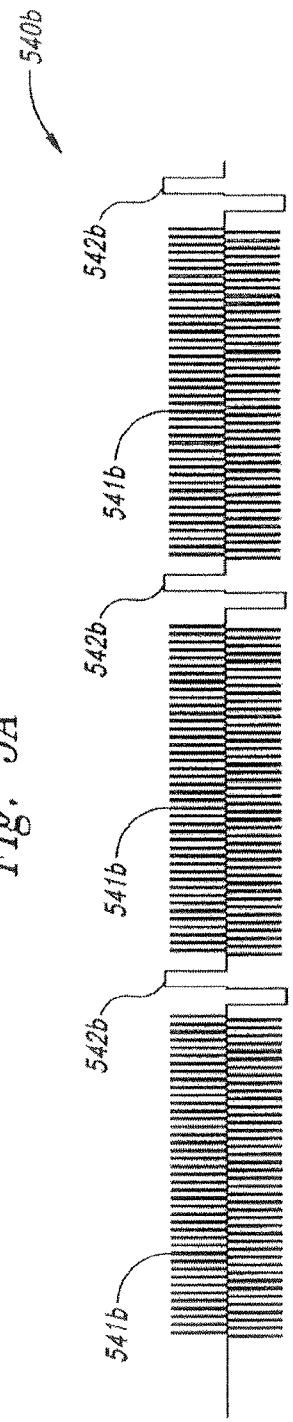

FIG. 5B illustrates another electrical signal 540*b* having first pulses 541*b* and second pulses 542*b*. In this particular embodiment, the first pulses 541*b* are provided at a higher duty cycle (e.g., about 85%) compared with that shown in FIG. 5A. The second pulses 542*b* are also provided at an amplitude slightly higher than that of the first pulses 541*a*.

The pulses shown in FIGS. 5A and 5B can be provided to different patients, or to the same patient at different times, or the pulses can be provided to the same patient at the same time, but via different leads. For example, the patient may be implanted with two leads generally similar to the lead shown in FIG. 4. The first signal 540*a* is then applied to the first and second contacts of one lead, and the second signal applied to the first and second contacts of the other lead. In other embodiments, the signals can be applied in any of a wide variety of manners, e.g., to two 8-contact leads, to one 8-contact lead and two 4-contact leads, to four 4-contact leads, or to other lead arrangements. In any of these embodiments, the second pulses can be applied to the same target neural population as are the first pulses, e.g., when it is expected that the target neural population will have both a paresthetic response and an anesthetic response. In other embodiments, the second pulses can be applied to a different neural population than are the first pulses. For example, if the target neural population to which the first pulses are applied is expected to have an anesthetic response, but not a paresthetic response, the second pulses can be applied to a different neural population. In such a case, the paresthetic response at the second neural population may still be used to influence the manner in which the first pulses are applied to the first target neural population. Further details of representative leads and associated systems and methods are included in co-pending U.S. patent application Ser. No. 12/765,747, filed concurrently herewith, titled "Selective High Frequency Spinal Cord Stimulation for Inhibiting Pain with Reduced Side Effects, and Associated Systems and Methods", and incorporated herein by reference.

Figure 5C:
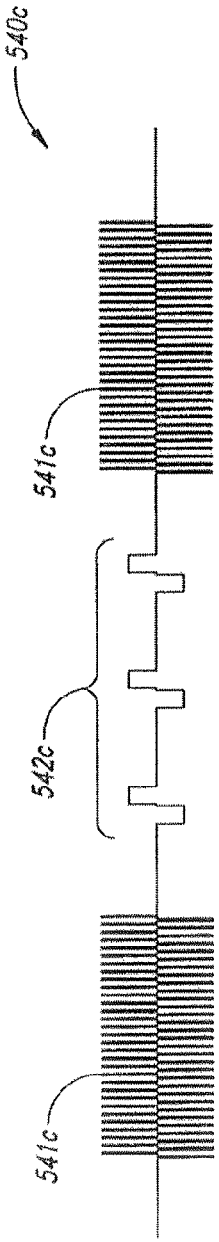

FIG. 5C illustrates still another signal 540*c* having spaced-apart bursts of first pulses 541*c*. Bursts of second pulses 542*c* are interleaved with the bursts of first pulses 541*c*. For example, a single burst of second pulses 542*c* may be positioned between neighboring bursts of first pulses 541*c*. This arrangement can be appropriate in cases where multiple, uninterrupted second pulses 542*c* are suitable for creating a paresthetic effect, and the resulting separation between bursts of the first pulses 541*c* does not detract significantly from the anesthetic effect created by the first pulses 541*c*.

Figure 5D:
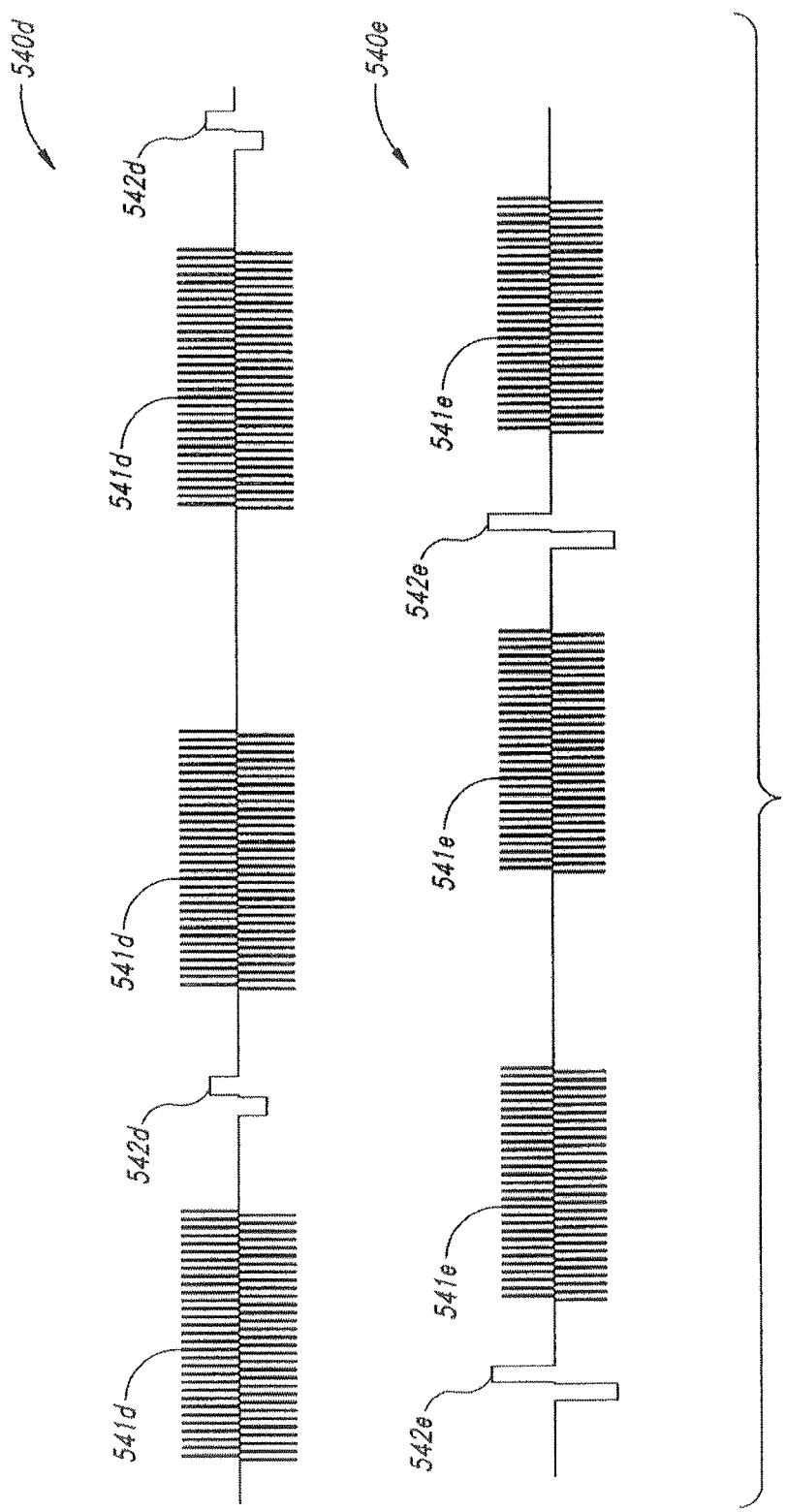

In one aspect of the embodiment shown in FIGS. 5A and 5B, the first and second pulses are the only pulses provided to the corresponding signal delivery element, and are provided to, for example, the first and second contacts 121, 122 of the lead body 110 shown in FIG. 4. In other embodiments, these signals may be applied to other contacts or combinations of contacts. For example, FIG. 5D illustrates an embodiment in which a first signal 540*d* applies corresponding first and second pulses 541*d*, 542*d* to a selected pair of contacts (e.g., the first and second contacts 121, 122 shown in FIG. 4) and a second signal 540*e* applies first and second pulses 541*e*, 542*e* to another pair of contacts (e.g., the seventh and eighth contacts 127, 128 shown in FIG. 4). The high frequency first pulses 541*d*, 541*e* are provided simultaneously at each pair of contacts, while the low second frequency pulses 542*d*, 542*e* are staggered in time and location. This arrangement may be used when the practitioner wishes to provide a broader field with the first pulses 541*d*, 541*e*. In other embodiments, the first and second pulses may be provided to other contacts, and/or in accordance with other timing patterns, based generally on a patient-specific basis.

In any of the foregoing embodiments, the signal delivery parameters selected for any of the first pulses 541*a-e* (referred to collectively as first pulses 541) and the second pulses 542*a-e* (referred to collectively as second pulses 542) can be selected to produce an anesthetic, non-paresthetic effect, and a paresthetic effect, respectively. As discussed above, in at least some embodiments, the first pulses 541 will be provided at a higher frequency than the second pulses 542. For example, the first pulses 541 can be provided at a frequency of from about 1.5 kHz to about 50 kHz, while the second pulses 542 can be provided in a range of from about 2 Hz to about 1.2 kHz. In other embodiments, the pulses can have different relationships. For example, the second pulses 542 can be within a 3 kHz to 10 kHz range, but at a frequency less than the first pulses 541.

Figure 6:
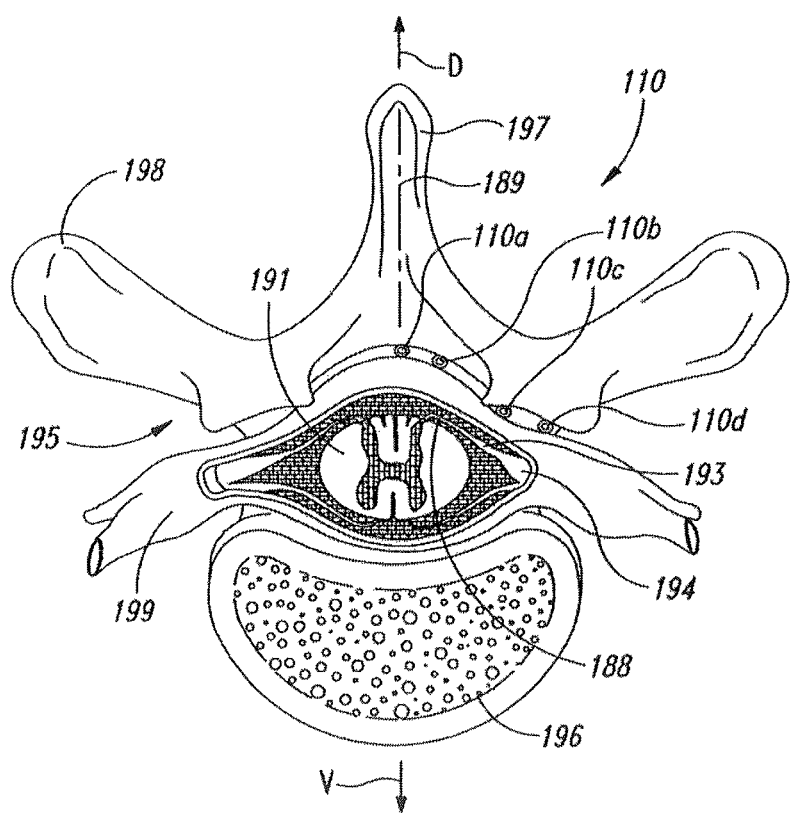
FIG. 6 is a partially schematic, cross-sectional illustration of a patient's spine, illustrating representative locations for implanted lead bodies in accordance with embodiments of the disclosure.

FIG. 6 is a cross-sectional illustration of the spinal cord 191 and an adjacent vertebra 195 (based generally on information from Crossman and Neary, "Neuroanatomy," 1995 (published by Churchill Livingstone)), along with selected representative locations for representative lead bodies 110 (shown as lead bodies 110*a*-110*d*) in accordance with several embodiments of the disclosure. The spinal cord 191 is situated between a ventrally located ventral body 196 and the dorsally located transverse process 198 and spinous process 197. Arrows V and D identify the ventral and dorsal directions, respectively. In particular embodiments, the vertebra 195 can be at T9, T10, T11 and/or T12 (e.g., for axial low back pain and/or leg pain) and in other embodiments, the lead bodies can be placed at other locations. The lead body can be positioned to provide the same or different pulses to different vertebral levels (e.g., T9 and T10). The spinal cord 191 itself is located within the dura mater 199, which also surrounds portions of the nerves exiting the spinal cord 191, including the dorsal roots 193 and dorsal root ganglia 194.

The lead body is generally positioned to preferentially modulate tactile fibers (e.g., to produce the paresthetic effect described above) and to avoid modulating fibers associated with nociceptive pain transmission. In a particular embodiment, a lead body 110a can be positioned centrally in a lateral direction (e.g., aligned with the spinal cord midline 189) to provide signals directly to the spinal cord 191. In other embodiments, the lead body can be located laterally from the midline 189. For example, the lead body can be positioned just off the spinal cord midline 189 (as indicated by lead body 110b), and/or proximate to the dorsal root 193 or dorsal root entry zone 188 (e.g., 1-4 millimeters from the spinal cord midline 189, as indicated generally by lead body 110c), and/or proximate to the dorsal root ganglion 194 (as indicated by lead body 110d). Other suitable locations for the lead body 110 include the "gutter," also located laterally from the midline 189. In still further embodiments, the lead bodies may have other locations proximate to the spinal cord 191 and/or proximate to other target neural populations, e.g., laterally from the midline 189 and medially from the dorsal root ganglion 194. In any of the foregoing embodiments, electrical pulses may be applied to the lead body 110 to provide both a paresthetic and an anesthetic effect, as described above. As discussed above, the patient can be implanted with a single lead body (e.g., one of the lead bodies 110a-110d) or multiple lead bodies (e.g., combinations of the lead bodies 110a-110d).

From the foregoing, it will be appreciated that specific embodiments of the invention have been described herein for purposes of illustration, but that various modifications may be made without deviating from the invention. For example, the signal delivery parameters may have values other than those specifically described above, but which are also selected to produce anesthetic or paresthetic effects in the manner described above. Particular embodiments were described above in the context of signals applied to the patient's spinal cord, but in other embodiments, signals (e.g., signals creating an anesthetic, non-paresthetic effect, and/or signals creating a paresthetic effect) can be applied to other neural populations, including, but limited to, peripheral nerves. For example, such methods can include applying first pulses to the patient's spinal cord to create an anesthetic, non-paresthetic effect, and applying second pulses to a peripheral nerve to create a paresthetic effect. Systems suitable for carrying out embodiments of the foregoing techniques are included in co-pending U.S. application Ser. No. 12/765,790, filed concurrently herewith, titled "Devices for Controlling High Frequency Spinal Cord Stimulation for Inhibiting Pain, and Associated Systems and Methods", and incorporated herein by reference.

Certain aspects of the invention described in the context of particular embodiments may be combined or eliminated in other embodiments. For example, the wave forms described above with reference to FIGS. 5A-5D may be combined in further embodiments. In addition, while advantages associated with certain embodiments have been described and the context of those embodiments, other embodiments may also exhibit such advantages. Not all embodiments need necessarily exhibit such advantages to fall within the scope of the present disclosure. Accordingly, the disclosure and associated technology can encompass other embodiments not expressly shown or described herein.

We claim:

1. A patient treatment system, comprising:
    an implantable pulse generator coupleable to an implantable signal delivery device and having a controller programmed with instructions for:
        directing a first, non-paresthesia generating electrical signal to the implantable signal delivery device to create an anesthetic effect in a patient, the first electrical signal having a first set of first signal delivery parameters, including a frequency in a frequency range from 1.5 kHz to 100 kHz, and a pulse width in a pulse width range of 10 microseconds to 333 microseconds; and
        directing a second electrical signal to the signal delivery device, the second electrical signal having a second set of second signal delivery parameters, including a frequency in a frequency range from 2 Hz to 1.2 kHz.

2. The system of claim 1, further comprising the implantable signal delivery device, wherein the implantable signal delivery device has a plurality of electrodes configured to be implanted within the patient's epidural space, proximate to one or more target neural populations in the patient's spinal cord, and wherein the controller is programmed with instructions for:
    delivering to the signal delivery device bursts of the first electrical pulses having a frequency in a first frequency range of from 1.5 kHz to 50 kHz, to create an anesthetic, non-paresthetic effect in the patient; and
    delivering to the signal delivery device the second electrical pulses to create a paresthetic effect in the patient, wherein the second electrical pulses include a single second pulse during an interval between sequential bursts of the first electrical pulses.

3. The system of claim 2 wherein the controller includes instructions for directing the first pulses to a first electrode of the signal delivery device and directing the second pulses to a second electrode of the signal delivery device, wherein the second electrode is different from the first electrode.

4. The system of claim 2 wherein the controller is programmed with instructions for directing the first and second pulses sequentially to the same electrode of the signal delivery device.

5. The system of claim 2 wherein the first and second pulses have different pulse widths.

6. The system of claim 2 wherein the first pulses have a first pulse width and wherein the second pulses have a second pulse width, and wherein the second pulse width is greater than the first pulse width.

7. The system of claim 1 wherein the first set of first signal delivery parameters includes a frequency of from 3 kHz to 10 kHz, and the second set of second signal delivery parameters includes a frequency of from 20 Hz to 1.2 kHz.

8. The system of claim 1 wherein the first set of first signal delivery parameters includes a pulse amplitude of from 0.5 mA to 4 mA.

9. The system of claim 1 wherein the first set of first signal delivery parameters includes pulse widths between 33 microseconds and 100 microseconds, inclusive.

10. The system of claim 1 wherein the second set of second signal delivery parameters includes a pulse amplitude of from 2 mA to 10 mA.

11. The system of claim 1 wherein the controller is programmed with instructions for directing the first pulses in accordance with a duty cycle.

12. The system of claim 1 wherein the controller further includes instructions for receiving first updates to the first signal delivery parameters and second, independent updates to the second signal delivery parameters.

13. The system of claim 1 wherein the first set of first signal delivery parameters includes a frequency of from 3 kHz to 20 kHz.

14. The system of claim 1 wherein the first set of first signal delivery parameters includes a frequency of from 3 kHz to 15 kHz.

15. The system of claim 1 wherein the first set of first signal delivery parameters includes a frequency of from 5 kHz to 15 kHz.

16. The system of claim 1 wherein the first set of first signal delivery parameters includes a pulse amplitude of from 0.1 mA to 20 mA.

17. The system of claim 1 wherein the first set of first signal delivery parameters includes a pulse width between 25 microseconds and 166 microseconds, inclusive.

18. The system of claim 1 wherein the second set of second signal delivery parameters includes a pulse width from 10 microseconds to 1,000 microseconds, inclusive.

19. The system of claim 1 wherein the controller includes instructions for interleaving one or more second pulses between sequential bursts of the first pulses.

20. The system of claim 1 wherein the controller includes instructions for directing the first pulses to a first electrode of the signal delivery device and directing the second pulses to a second electrode of the signal delivery device different than the first electrode.

21. The system of claim 1 wherein the controller is programmed with instructions for directing the first and second pulses sequentially to a common electrode of the signal delivery device.

22. The system of claim 1 wherein the controller is programmed with instructions for directing the first and second pulses to a common electrode of the signal delivery device, with a single second pulse directed during an interval between sequential bursts of the first pulses, without the first pulses overlapping temporally with the second pulses, and with the first pulses having a first pulse width and the second pulses having a second pulse width greater than the first pulse width.

23. The system of claim 1 wherein the second pulses include a single second pulse delivered during an interval between sequential bursts of the first pulses.

24. The system of claim 1 wherein the controller is programmed with instructions for:
increasing an amplitude of the first pulses;
increasing an amplitude of the second pulses as the amplitude of the first pulses is increased; and
based on patient feedback to the second pulses, changing the first signal delivery parameters.

25. The system of claim 1 wherein the controller is programmed with instructions for changing the amplitudes of the first and second pulses in a parallel manner.

26. The system of claim 25 wherein the amplitudes of the first and second pulses are offset, and wherein changing the amplitudes of the first and second pulses includes changing the amplitudes of the first and second pulses by different amounts.

27. The system of claim 1 wherein the controller is programmed with instructions for identifying a fault with the delivery of the first pulses based at least in part on the presence or absence of patient response to changing an amplitude of the second pulses.

28. The system of claim 27 wherein identifying a fault is based at least in part on an absence of a patient response.

29. A patient treatment system, comprising:
an implantable pulse generator coupleable to an implantable signal delivery device and having a controller programmed with instructions for:
directing a first, non-paresthesia generating electrical signal to the implantable signal delivery device to create an anesthetic effect in a patient, the first electrical signal having a first set of first signal delivery parameters, including a frequency in a frequency range from 1.5 kHz to 100 kHz, a pulse amplitude of from 0.5 mA to 10 mA, and a pulse width of from 10 microseconds to 333 microseconds; and
directing a second electrical signal to the signal delivery device, the second electrical signal having a second set of second signal delivery parameters, including a frequency in a frequency range from 2 Hz to 1.2 kHz.

* * * * *